US011628305B2

(12) United States Patent
Nielsen et al.

(10) Patent No.: US 11,628,305 B2
(45) Date of Patent: Apr. 18, 2023

(54) RECHARGE OF IMPLANTED MEDICAL DEVICES

(71) Applicant: Medtronic, Inc., Minneapolis, MN (US)

(72) Inventors: Christian S. Nielsen, River Falls, WI (US); Rajesh V. Iyer, Eden Prairie, MN (US); Gordon O. Munns, Stacy, MN (US); Craig L. Schmidt, Eagan, MN (US); Paul B. Young, New Richmond, WI (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 17/497,653

(22) Filed: Oct. 8, 2021

(65) Prior Publication Data
US 2022/0029465 A1   Jan. 27, 2022

Related U.S. Application Data

(62) Division of application No. 15/893,044, filed on Feb. 9, 2018, now Pat. No. 11,152,819.

(51) Int. Cl.
*A61N 1/372* (2006.01)
*H01F 38/14* (2006.01)
(Continued)

(52) U.S. Cl.
CPC ........ *A61N 1/37229* (2013.01); *A61B 5/0031* (2013.01); *A61B 5/6861* (2013.01);
(Continued)

(58) Field of Classification Search
CPC  A61N 1/37229; A61N 1/3787; A61B 5/0031; A61B 5/6861; A61B 2560/0219;
(Continued)

(56) References Cited

U.S. PATENT DOCUMENTS 5,117,824 A   6/1992  Keimel et al.
6,047,214 A   4/2000  Mueller
(Continued)

FOREIGN PATENT DOCUMENTS

EP       2451526 B2    6/2013
WO   2000066221 A1   11/2000
(Continued)

OTHER PUBLICATIONS

Carta, et al., "A wireless power supply system for robotic capsular endoscopes," Sensors and Actuators A, 2010, pp. 177-183.
(Continued)

*Primary Examiner* — M Baye Diao
(74) *Attorney, Agent, or Firm* — Shumaker & Sieffert, P.A.

(57) ABSTRACT

Systems, devices and methods allow inductive recharging of a power source located within or coupled to an implantable medical device while the device is implanted in a patient. The recharging system/device in some examples includes a first electrical coil and a second electrical coil configured to generate opposing magnetic fields forming a resultant magnetic field within a recharging envelope located between the coils. A third coil of the implantable medical device may be positioned within the recharging envelope so that the resultant magnetic field is imposed on the third coil, causing electrical energy to be induced in the third coil, the induced electrical energy used to recharge a power source of an implantable medical device coupled to the third coil, and/or to power operation of the implantable medical device.

10 Claims, 19 Drawing Sheets

(51) Int. Cl.
| | | |
|---|---|---|
| | *H02J 50/10* | (2016.01) |
| | *H02J 50/90* | (2016.01) |
| | *A61B 5/00* | (2006.01) |
| | *A61N 1/378* | (2006.01) |
| | *H02J 50/80* | (2016.01) |
| | *H02J 7/02* | (2016.01) |
| | *H02J 5/00* | (2016.01) |

(52) U.S. Cl.
CPC .......... *A61N 1/3787* (2013.01); *H01F 38/14* (2013.01); *H02J 5/00* (2013.01); *H02J 7/02* (2013.01); *H02J 50/10* (2016.02); *H02J 50/80* (2016.02); *H02J 50/90* (2016.02); *A61B 2560/0219* (2013.01)

(58) Field of Classification Search
CPC ..... H01F 38/14; H02J 5/00; H02J 7/02; H02J 50/10; H02J 50/80; H02J 50/90
USPC ........................................................ 128/898
See application file for complete search history.

(56) References Cited

U.S. PATENT DOCUMENTS

| | | | |
|---|---|---|---|
| 7,211,986 | B1 | 5/2007 | Flowerdew et al. |
| 7,225,032 | B2 | 5/2007 | Schmeling et al. |
| 7,286,881 | B2 | 10/2007 | Schommer et al. |
| 8,204,602 | B2 | 6/2012 | Kallmyer |
| 8,244,367 | B2 | 8/2012 | Wahlstrand et al. |
| 8,278,871 | B2 | 10/2012 | Kallmyer |
| 8,473,066 | B2 | 6/2013 | Aghassian et al. |
| 8,548,590 | B2 * | 10/2013 | Aghassian ........... A61N 1/3787 607/33 |
| 8,554,322 | B2 | 10/2013 | Olson et al. |
| 8,676,318 | B2 | 3/2014 | Carbunaru et al. |
| 8,676,337 | B2 | 3/2014 | Kallmyer |
| 8,751,001 | B2 | 6/2014 | Grevious et al. |
| 8,864,676 | B2 | 10/2014 | Beasley et al. |
| 8,901,775 | B2 | 12/2014 | Armstrong et al. |
| 9,216,297 | B2 | 12/2015 | Kast et al. |
| 9,339,659 | B2 | 5/2016 | Carbunaru et al. |
| 9,700,730 | B2 | 7/2017 | Carbunaru et al. |
| 9,962,085 | B2 * | 5/2018 | Griffith ................ H02J 50/40 |
| 10,695,572 | B2 * | 6/2020 | Maile ................ A61N 1/37229 |
| 10,707,692 | B2 * | 7/2020 | Schmidt ................ A61B 5/00 |
| 11,129,996 | B2 * | 9/2021 | Aghassian ............. H02J 50/80 |
| 11,152,819 | B2 | 10/2021 | Nielsen et al. |
| 2006/0061325 | A1 | 3/2006 | Tang |
| 2008/0027513 | A1 * | 1/2008 | Carbunaru ......... A61N 1/37223 607/2 |
| 2009/0069869 | A1 | 3/2009 | Stouffer et al. |
| 2009/0112291 | A1 | 4/2009 | Wahlstrand |
| 2009/0270951 | A1 | 10/2009 | Kallmyer |
| 2010/0225174 | A1 | 9/2010 | Jiang |
| 2011/0004278 | A1 | 1/2011 | Aghassian et al. |
| 2011/0210621 | A1 | 9/2011 | Iwaisako |
| 2011/0248673 | A1 | 10/2011 | Aerts et al. |
| 2012/0119699 | A1 | 5/2012 | Carbunaru |
| 2013/0009594 | A1 | 1/2013 | Osswald |
| 2013/0293025 | A1 | 11/2013 | Xu et al. |
| 2014/0276928 | A1 | 9/2014 | Vanderpool et al. |
| 2015/0180267 | A1 * | 6/2015 | Romanelli ............ H02J 7/0044 320/108 |
| 2015/0204928 | A1 | 7/2015 | Hoover |
| 2015/0244178 | A1 | 8/2015 | Tang |
| 2016/0175600 | A1 | 6/2016 | Amir et al. |
| 2016/0336813 | A1 | 11/2016 | Yeh et al. |
| 2016/0339256 | A1 | 11/2016 | Poon et al. |
| 2017/0040826 | A1 | 2/2017 | Arendarik |
| 2017/0043077 | A1 | 2/2017 | Tuseth |
| 2017/0170688 | A1 | 6/2017 | Maniktala |
| 2017/0201118 | A1 | 7/2017 | Nejatali et al. |
| 2017/0281955 | A1 | 10/2017 | Maile et al. |
| 2018/0212451 | A1 | 7/2018 | Schmidt et al. |
| 2019/0247669 | A1 | 8/2019 | Nielsen et al. |
| 2020/0328615 | A1 | 10/2020 | Schmidt et al. |

FOREIGN PATENT DOCUMENTS

| | | | |
|---|---|---|---|
| WO | 2007064609 | A1 | 6/2007 |
| WO | 2009131723 | A1 | 10/2009 |
| WO | 2013190471 | A1 | 12/2013 |
| WO | 2017218353 | A1 | 12/2017 |

OTHER PUBLICATIONS

Mao, et al., "An Efficient Wireless Power Transmission System for the Capsule Endoscoy Application," 2011, IEEE, pp. 221-224.

Zhiwei, et al., "Efficiency optimization of wireless power transmission systems for active capsule endoscopes," Physiological Measurement, 32, 2011, pp. 1561-1573.

Basar, et al., "Performance Evaluation of Power Transmission Coils for Powering Endoscopic Wireless Capsules," 2015, IEEE, pp. 2263-2266.

Bingquan, et al., "Portable wireless power transmission system of a video capsule endoscopy: design and realization," International Conference on Biomedical Engineering and Biotechnology, 2012, pp. 409-412.

Jia, et al., "The optimization of wireless power transmission: design and realization," The International Journal of Medical Robotics and Computer Assisted Surgery, Int. J. Med Robotics Comput Assist Surg, Apr. 2012; 8: pp. 337-347.

Padron, et al., "Simulation and Construction of a Maxwell Coil," Florida Atlantic University, 2015, accessed on Jan. 26, 2017, 1 pp.

Lenaerts, et al., "Inductive powering of a freely moving system," Sensors and Actuators, 2005, available online Mar. 2, 2005, pp. 522-530.

Ho, et al., "Wireless Power Transfer to Deep-Tissue Microimplants," PNAS, Jun. 3, 2014, vol. 111, No. 20, pp. 7974-7979.

Maile, PhD, et al., "Wireless Power Transfer for Deeply Implanted Medical Devices (IMD)," Boston Scientific, presented Dec. 5-7, 2016 at Biological & Chemical Sensors Summit, San Diego, CA, 20 slides.

Yates, "Wireless power delivery for ventricular assist devices," Imperial College, London, Dec. 7, 2017, presented Dec. 5-7, 2017 at Biological & Chemical Sensors Summit, San Diego, CA, 40 slides.

Von Novak, "Power Systems for Medical Implants," Qualcomm Technologies, Inc., presented Dec. 5-7, 2016 at Biological & Chemical Sensors Summit, San Diego, CA, 24 slides.

Wilken-Resman, et al., "Power Transfer Prediction Tool for Medical Implants," Qualcomm Technologies, presented Dec. 5-7, 2016 at Biological & Chemical Sensors Summit, San Diego, CA, 15 slides.

Prosecution History from U.S. Appl. No. 15/416,655, dated May 9, 2019 through Dec. 10, 2019, 46 pp.

Prosecution History from U.S. Appl. No. 15/893,044, dated Dec. 10, 2020 through Jun. 11, 2021, 22 pp.

Examination Report from counterpart European Application No. 19703805.2, dated Jun. 9, 2021, 5 pp.

Response to Extended Search Report dated Jun. 9, 2021, from counterpart European Application No. 19703805.2, filed Dec. 7, 2021, 14 pp.

Office Action from U.S. Appl. No. 16/915,218, dated Jun. 17, 2022, 8 pp.

(PCT/US2019/012982) PCT Notification of Transmittal of the International Search Report and the Written Opinion of the International Searching Authority, dated Apr. 1, 2019, 13 pages.

Notice of Allowance from U.S. Appl. No. 16/915,218 dated Oct. 5, 2022, 7 pp.

Response to Office Action dated Jun. 17, 2022 from U.S. Appl. No. 16/915,218, filed Sep. 16, 2022, 11 pp.

* cited by examiner

RECHARGE OF IMPLANTED MEDICAL DEVICES

This application is a divisional application of U.S. application Ser. No. 15/893,044 which was filed on Feb. 9, 2018, the entire content of which is incorporated herein by reference.

TECHNICAL FIELD

The disclosure relates to methods and systems to recharge a power source located within a medical device that has been implanted in a patient.

BACKGROUND

Various implantable medical devices have been clinically implanted or proposed for therapeutically treating or monitoring one or more physiological and/or neurological conditions of a patient. Such devices may be adapted to monitor or treat conditions or functions relating to heart, muscle, nerve, brain, stomach, endocrine organs or other organs and their related functions. Advances in design and manufacture of miniaturized electronic and sensing devices have enabled development of implantable devices capable of therapeutic as well as diagnostic functions, including pacemakers, cardioverters, defibrillators, biochemical sensors, implantable loop recorders, and pressure sensors, among others. Such devices may be associated with leads that position electrodes or sensors at a desired location, or may be leadless with electrodes integrated into the device housing. These devices may have the ability to wirelessly transmit data either to another device implanted in the patient, or to another instrument located externally of the patient, or both.

Although implantation of some devices requires a surgical procedure (e.g., pacemakers, defibrillators, etc.), other devices may be small enough to be delivered and placed at an intended implant location in a relatively noninvasive manner, such as by a percutaneous delivery catheter, or transvenously. By way of illustrative example, implantable miniature sensors have been proposed and used in blood vessels to measure directly the diastolic, systolic and mean blood pressures, as well as body temperature and cardiac output of a patient. As one example, patients with chronic cardiovascular conditions, particularly patients suffering from chronic heart failure, may benefit from the use of implantable sensors adapted to monitor blood pressures. As another example, subcutaneously implantable monitors have been proposed and used to monitor heart rate and rhythm, as well as other physiological parameters, such as patient posture and activity level. Such direct in vivo measurement of physiological parameters may provide significant information to clinicians to facilitate diagnostic and therapeutic decisions. In addition, miniaturized pacemakers that may be implanted directly within a patient's heart with or without the need for external leads, have been proposed, built, and adapted to provide both pacing and other electrical therapy to the patient.

SUMMARY

The disclosure describes implantable medical devices, systems, and associated techniques, structures, and assemblies configured to provide recharging of power sources within medical devices that have been implanted within a patient. The implanted medical devices including these power sources to be recharged are often small devices that have been implanted relatively deeply within the patient, for example implanted internally within the heart of a patient. An example of such a device is the Medtronic® Micra® self-contained pacemaker that is designed to be implanted internally, for example within a chamber of the heart of a patient, and in various examples requires no external leads coupled to the device in order to provide pacing and electrical stimulation therapy to the heart.

Due to the need to miniaturize these devices so that they may be implanted in the desired locations, such as within the heart, or to minimize any obstruction, e.g., to blood flow, created by the device once implanted, such devices are often provided with a uni-directional or planar receive antenna to conserve space within the device and reduce battery usage. These antennae are routinely used for telemetry and communications to and from the device.

The application of the antenna for inductive recharging of the devices faces the same constraints, e.g., size and directionality constraints, as faced when using the antenna for telemetry and communication functions. In addition, the exact orientation of the implantable medical device (and thus the antenna with the implantable medical device) following the implantation of the device may not be known, and/or the implantable medical device may not be easily re-positioned to allow for optimization of operations (e.g., communication efficiency in the case of telemetry and recharging power transfer efficiency in the case of inductively coupled recharging), thus adding to the challenge of determining the proper or at least the most efficient orientation of the devices used to recharge the power source or sources included within the implanted device. These factors, e.g., the combination of deeply implanted devices having limited receive antenna orientations that provide good coupling for inductively coupled recharge are addressed by the systems, devices, and methods described in this disclosure.

Additionally, and importantly, the devices, systems, and methods may include a single pair of coils, which may be physically arranged as a Helmholtz coil, but configured to generate opposing electromagnetic fields between the coils such that a positional angle θ (theta) of rotation of the antenna of the implanted device around a longitudinal axis extending between the pair of recharging coils is eliminated as a factor in determining the efficiency of the inductively coupled power. In addition, controlling the relative strengths of the magnetic field generated by each of the recharging coils may be manipulated to "steer" the direction of the resultant magnetic field being imposed on the antenna of the implanted device, thru further increasing the coupling efficiency between the resultant magnetic field and the receive antenna of the implanted device. Use of the devices, system and techniques described herein may reduce the need for a more complex alignment procedure, and/or eliminate the need for multiple sets of charging coils to be use simultaneously, when recharging the power source of a medical device that is implanted in a patient. This ability to provide a high level of efficiency for the inductive coupling between a single pair of recharging coils of a recharging system inducing electrical energy in a uni-directional or planar type antenna of an implanted device may be important advantage in the performance aspects of the devices, systems, and methods disclosed herein.

Examples described in this disclosure may be directed to a method for recharging a power source located in an implantable medical device implanted in a patient, the method comprising energizing, by recharging circuitry, a first electrical coil to generate a first magnetic field having a first magnetic field direction, and energizing, by the recharging circuitry, a second electrical coil to generate a second magnetic field having a second magnetic field direction opposing the first magnetic field direction relative to a longitudinal axis extending between the first electrical coil and the second electrical coil, wherein an interaction between the first magnetic field and the second magnetic field generates a resultant magnetic field within a recharging envelope located in an area between the first electrical coil and the second electrical coil when the first electrical coil and the second electrical coil are electrically energized. The method further includes inducing, by the resultant magnetic field, an electrical current in a third coil within the implantable medical device by imposing the resultant magnetic field onto the third coil when the third coil is located within the recharging envelope and the first electrical coil and the second electrical coil are electrically energized, wherein the resultant magnetic field generated within the recharging envelope comprises a resultant magnetic field direction that renders irrelevant a positional angle θ (theta) of rotation of the third coil around the longitudinal axis extending between the first electrical coil and the second electrical coil with respect to a coupling efficiency of the level of the electrical current being induced in the third coil by the resultant magnetic field, The method also includes charging, by the electrical current induced in the third coil, the power source in the implantable medical device.

Examples described in this disclosure may be directed to a recharging system for recharging a power source located in an implantable medical device implanted in a patient, the recharging system comprising recharging circuitry configured to provide electrical power from one or more electrical power outputs; and a pair of electrical coils coupled to the recharging circuitry, the pair of electrical coils comprising a first electrical coil and a second electrical coil having a longitudinal axis extending between the first electrical coil and the second electrical coil, the pair of electrical coils configured to be electrically energized by the electrical power from the one or more electrical power outputs, and to generate opposing magnetic fields comprising a resultant magnetic field generated within a recharging envelope located in an area between the pair of coils when the pair of coils is electrically energized. The resultant magnetic field is configured to generate an inductively coupled electrical current in a third coil located within the implantable medical device when the third coil is located within the recharging envelope and the first electrical coil and the second electrical coil are electrically energized, the inductively coupled electrical current configured to recharge a power source of the implantable medical device, and the resultant magnetic field renders irrelevant a positional angle θ (theta) of rotation of the third coil around the longitudinal axis extending between the first electrical coil and the second electrical coil with respect to a coupling efficiency of the level of the electrical current being induced in the third coil by the resultant magnetic field.

Examples described in this disclosure may be directed to a recharging system for recharging a power source located in an implantable medical device implanted in a patient, the recharging system comprising a pair of electrical coils coupled to the recharging circuitry, the pair of electrical coils comprising a first electrical coil and a second electrical coil having a common longitudinal axis and separated by a separation distance along the longitudinal axis, wherein each of the first electrical coil and the second electrical coil comprising a circular-shaped winding of an electrical conductor forming a toroid that encircles a portion of the longitudinal axis, the pair of electrical coils configured to be electrically energized to generate opposing magnetic fields comprising a resultant magnetic field generated within a recharging envelope located in an area between the pair of coils when the pair of coils is electrically energized, and wherein the resultant magnetic field is configured to generate an inductively coupled electrical current in a third coil located within the implantable medical device when the third coil is located within the recharging envelope and the first electrical coil and the second electrical coil are electrically energized, the inductively coupled electrical current configured to recharge a power source of the implantable medical device, and wherein the resultant magnetic field renders irrelevant a positional angle θ (theta) of rotation of the third coil around the longitudinal axis extending between the first electrical coil and the second electrical coil with respect to a coupling efficiency of the level of the electrical current being induced in the third coil by the resultant magnetic field. The system also comprises recharging circuitry electrically coupled to the pair coils, the recharging circuitry comprising a signal generator configured to generate an electrical signal comprising a time-varying waveform, a first power amplifier coupled to the signal generator and the first electrical coil, the first power amplifier configured to receive the electrical signal and to generate a first level of electrical energy for energizing the first electrical coil, a second power amplifier coupled to the signal generator and the second electrical coil, the second power amplifier configured to receive the electrical signal and to generate a second level of electrical energy for energizing the second electrical coil, and position control circuitry configured to control, by one or more actuators devices that are mechanically coupled to the pair of coils, the positioning of the pair of coils relative the third coil when the third coil is located in the area between the pair of coils, the position control circuitry configured to control the one or more mechanical actuators to at least position the pair of coils so that the third coil is located within the recharging envelope.

This summary is intended to provide an overview of the subject matter described in this disclosure. It is not intended to provide an exclusive or exhaustive explanation of the apparatus and methods described in detail within the accompanying drawings and description below. The details of one or more aspects of the disclosure are set forth in the accompanying drawings and the description below.

BRIEF DESCRIPTION OF THE FIGURES

The details of one or more examples of this disclosure are set forth in the accompanying drawings and the description below. Other features, objects, and advantages of this disclosure will be apparent from the description and drawings, and from the claims.

Figure 1:
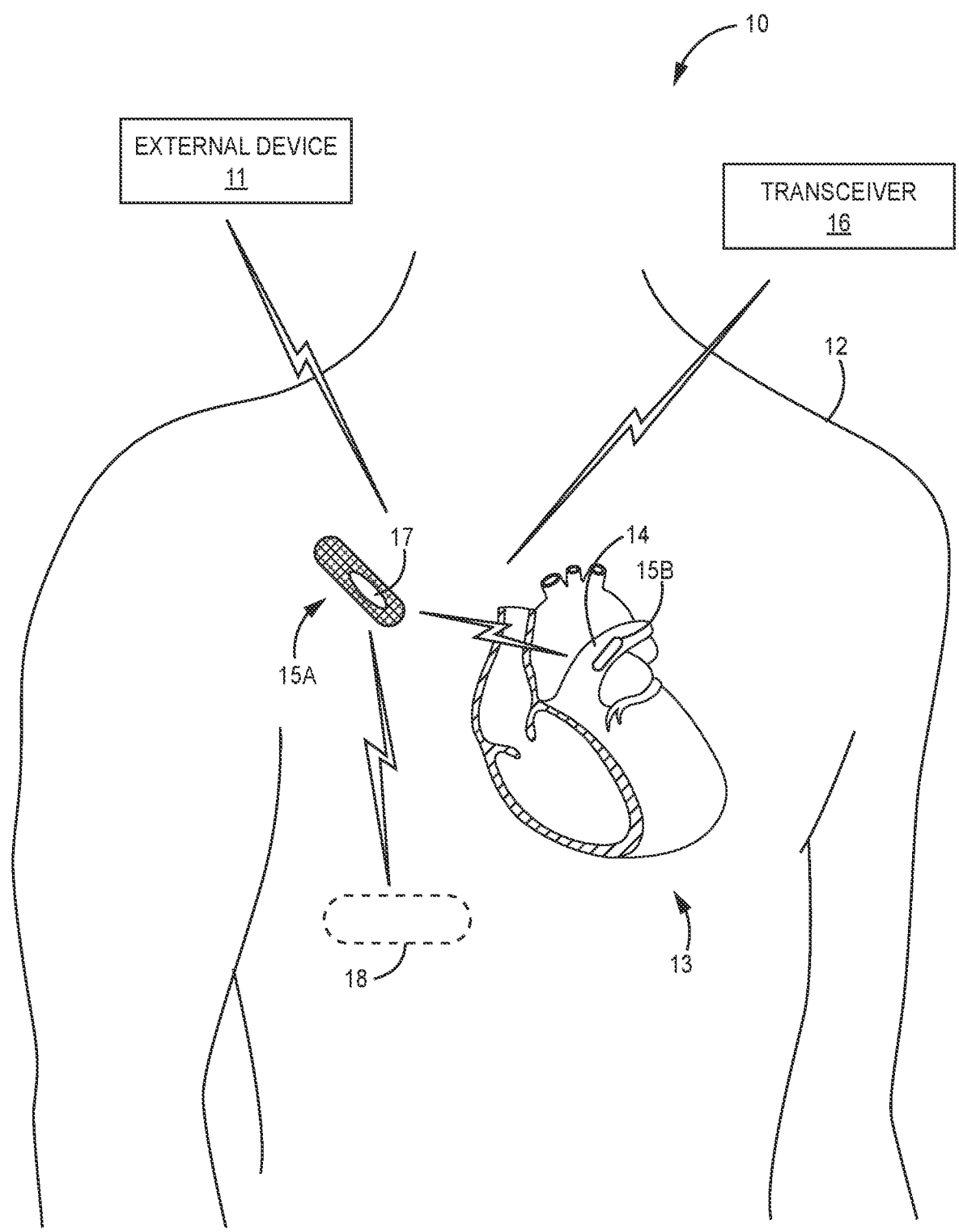
FIG. 1 is a conceptual drawing illustrating an example medical device system in conjunction with a patient according to various examples described in this disclosure.

In the figures, use of a same reference number or a same reference number with a letter extension may be used to indicate a same or corresponding device or element when used in a same drawing or in different drawings. In addition, unless otherwise indicated, devices and/or other objects such as a patient, an implantable medical device, or an electrical device such as an electrical coil, are not necessarily illustrated to scale relative to each other and/or relative to an actual example of the item being illustrated. In particular, various drawings provided with this disclosure illustrate a "patient" represented by a human-shaped outline, and are not to be considered drawn to scale relative to an actual human patient or with respect to other objects illustrated in the same figure unless otherwise specifically indicated in the figure for example by dimensional indicators, or for example as otherwise described in the text of the disclosure.

DETAILED DESCRIPTION

Fast recharge of small, deeply implanted medical devices, such as the Medtronic® Micra® Pacemaker, via transdermal, magnetic induction presents many challenges. These include providing an adequate magnetic field intensity at a given frequency at the implant location such that rapid recharge can be accomplished without exceeding electric field and magnetic field exposure safety limits for the patient, while accounting for an uncontrolled orientation of the implanted device, and while accounting for the true spatial location of the device in addition to the device/antenna orientation. In various examples of implanted medical devices, a primary (non-rechargeable) battery has a finite energy reservoir which limits its mission life based on its size and energy density (for a given energy usage rate). This limits the useful duration of the implanted device. A rechargeable battery conceptually offers a semi-infinite reservoir of energy in which the size of the battery and charged energy density determines the recharge frequency rather than the mission life (under the assumption of negligible battery capacity fade). A result of a semi-infinite energy source is the opportunity to allow the device to provide additional features and functions that may otherwise be limited or unavailable given a finite energy source constraint. Another result of this semi-infinite energy source is the potential reduction or elimination of a need to perform a surgically invasive device replacement procedure required due to exhausting the capacity of the primary (i.e., non-rechargeable) battery. The devices, systems, and techniques described in this disclosure address many of the challenges associated with recharging these power sources within the implanted medical devices.

The systems, devices and method described in this disclosure provide for fast recharge of a battery or other rechargeable power sources in a small, deeply implanted medical device, such as the Micra® leadless pacemaker. In some examples, the techniques of this disclosure use a single pair of coils, in some examples physically arranged as a Helmholtz coil, but where the pair of coils is configured to provide opposing magnetic fields in a volume located between the pair of coils when coils are electrically energized. The resultant magnetic field generated by the interaction of the opposing magnetic fields may provide an envelope, referred to as the "estimated optimal recharging envelop," or simply the "recharging envelope." The recharging envelope comprises a portion of the resultant magnetic field in which a positional angle θ (theta) of rotation of a third coil (e.g., the receiving coil of an implanted medical device) relative to the longitudinal axis extending between the recharging coils is rendered irrelevant with respect to the level of inductive coupling efficiency being achieved for the coupled electrical energy (e.g., electrical current) induced in the receive antenna by the resultant magnetic field.

In some examples, the resultant magnetic field generated within the recharging envelope has a direction that extends at angles that are perpendicular to a longitudinal axis common to both of the electrical coils of the single pair of coils. When the receive antenna of the implanted medical device is located within the resultant magnetic field provided within the estimated optimal recharging envelop, positional angle θ (theta) of rotation of the receive antenna relative to the longitudinal axis extending between the recharging coils is rendered irrelevant with respect to the level of inductive coupling (e.g., the coupling efficiency) that is achieved between the resultant magnetic field and the level of current being induced into the receive antenna as long as the position of the receive antenna is also maintained within the recharging envelope.

In some examples, the position of the single pair of electrical coils may be adjusted, for example by tilting the coils, to change the direction of the longitudinal axis relative to the orientation of the receiving coil while maintaining the position of the electrical coils relative to each other. By adjusting the position to the pair of coils in this way, the perpendicular orientation of the resultant magnetic field may be reoriented to align with, or at least to better align with, an axis of orientation of the receive antenna. This improved alignment may increase the level of coupling efficiency, and thus the level of induced current being generated in the receive antenna by the resultant magnetic field. The initial positioning of the pair of coils relative to the location of the receive antenna, and/or the adjustments to the positioning of the coils to control the reorientation of the direction of the resultant magnetic field, may be made based on a feedback signal. The feedback signal may be communicated from the implanted medical device, and may include information that indicates a level of coupling efficiency being achieved between the receive antenna and the resultant magnetic field.

In some examples, the resultant magnetic field generated within the estimated optimal recharging envelope extends at angles that are non-perpendicular to a longitudinal axis common to both of the electrical coils of the single pair of coils. In such examples, the level of electrical energy provided to one of the pair of coils is not equal to the level of electrical energy being provided to the second coil of the pair of coils. As a result of this unequal level of electrical energization, the direction of the resultant magnetic field may be "bent" or "steered" in a direction having the non-perpendicular angles relative to the longitudinal axis common to both coils. The degree of bending, and thus the angles formed between the longitudinal axis and the direction of the resultant magnetic field can be controlled, e.g., can be steered, by controlling the relative levels of electrical energy provide to each of the coils, respectively, of the pair of coils. When the receive antenna of the implanted medical device is located within the resultant magnetic field provided within the estimated optimal recharging envelop, steering of the resultant magnetic field being generated by the opposing magnetic fields generated by each of the recharging coils may be used to align the resultant magnetic field with an angle of orientation φ (phi) between the normal axis of the third coil and the longitudinal axis. This alignment may increase the level of the inductive coupling efficiency being achieved between the resultant magnetic field and the receive antenna.

The initial positioning of the pair of coils relative to the location of the receive antenna, and/or the adjustments to the relative levels of electrical energy provided to the coils to control the reorientation of the direction of the resultant magnetic field, may be made based on a feedback signal. The feedback signal may for example be communicated from the implanted medical device, and may include information that indicates a level of coupling efficiency being achieved between the receive antenna and the resultant magnetic field. Thus, it is possible to establish a resultant magnetic field at the implanted device that is independent of both implant depth and implant location, and a positioning of the receive antenna in an estimated optimal recharging envelop generated the energization of the recharging coils that renders a positional angle θ (theta) of rotation of the third coil around a longitudinal axis extending between the pair of recharging coils irrelevant with respect to a coupling efficiency of the level of the electrical current being induced in the third coil by the resultant magnetic field.

The systems, devices, and methods described herein provide a magnetic field that may be used to efficiently induce electrical energy (e.g., an electrical current) into a receive antenna included within an implanted medical device with a minimum need for complex alignment between the transmit antennas and the receive antenna. The induced electrical energy may be used to recharge a power source of the implanted medical device using the externally provided magnetic field, and/or to power electronic circuitry included within or coupled to the implanted medical device, including devices that may be considered deeply implanted within the patient, (e.g., devices implanted more than two to three centimeters below the skin or outer surface of the patient).

The ability to quickly recharge (for example within a one-hour recharging period of time) the power source of an implanted medical device, for example on a monthly or yearly cycle, without the need to explant the device, allows the benefits described above. These benefits may include use of a smaller power source within the implantable medical device itself to help miniaturize the implantable medical device, and/or enabling higher power functionality for the implanted medical device. In some examples, the techniques described herein may provide an overall longer mission lifespan for the device using a smaller sized power source.

The systems, devices and methods described in some examples in this disclosure provide a solution to the orientation challenge of recharging power sources within deeply implanted medical devices by using a single pair of electrical coils configured to generate opposing magnetic fields. This provides a solution similar to the use of a three-axis receiving coil in the implanted device, but it allows a much simpler and more space-efficient design of the implanted device since a single axis (uni-directional) receiving coil can now be used in the implanted device. The systems, devices and methods described in this disclosure provide the ability to match the direction of a resultant magnetic field provided by the single pair of recharging coils to any single axis receiving coil/antenna of an implanted medical device, for example by tilting or steering the generated resultant magnetic field to provide maximum coupling between the resultant magnetic field and the receiving coil/antenna of the implanted medical device.

Throughout this disclosure, the use of the term "area" may be used in reference to a particular extent of space, which may include a three-dimensional space, and is not necessarily intended to be limited to a two-dimensional surface unless specifically described as being limited to a geometric "area" or another entity, such as a line, that is specifically described as a one-dimensional or as a two-dimensional entity. Examples of the use of the term "area" may refer to the three-dimensional space comprising an "area" located between a pair of electrical coils, and/or may be used in referring to volumetric space comprising an "area" included within a recharging envelope, as further described below.

FIG. 1 is a conceptual drawing illustrating an example of a medical device system 10 in conjunction with a patient 12 according to various examples described in this disclosure. The systems, devices, and techniques described in this disclosure provide for charging of power sources of the internal, and in some instances deeply implanted devices, including implantable medical devices (IMDs) such as IMD 15A, IMD 15B, and/or sensors 18 of medical device system 10, as further described below. For purposes of this description, knowledge of cardiovascular anatomy is presumed, and details are omitted except to the extent necessary or desirable to explain the context of the techniques of this disclosure. The systems, devices, and techniques describe herein may provide efficient coupling for recharging the power sources internal to IMD 15A, IMD 15B, and/or sensors 18. The advantages apply even when these devices are deeply implanted and/or include planar antennas or other configurations of antennas that are orientation specific with respect to coupling efficiencies between the antenna of the device being inductively recharged and the direction of the magnetic field(s) imposed on the device for the purpose of inducing electrical power into the antenna.

In the illustrated example, medical device system 10 includes IMD 15A, also referred to as implantable monitoring device 15A or an implantable hub device, or implantable loop recorder. Medical device system 10 also includes implantable pressure sensing device 15B, also referred to as IMD 15B. IMD 15B may be implanted within pulmonary artery 14 of heart 13. In some examples, pulmonary artery 14 of heart 13 may comprise a left pulmonary artery, whereas in other examples, pulmonary artery 14 may comprise a right pulmonary artery. For the sake of clarity, a fixation assembly for IMD 15B is not depicted in FIG. 1. Medical device system 10 is an example of several components of a medical device system 10 configured to implement techniques described herein for monitoring physiological parameters of patient 12, such as activity counts, heart rates, respiration rates, systemic blood pressures, body temperature(s), and body postures, and to allow for recharging of a power source, such as a battery, located within any of the one or more implanted medical devices 15A, 15B included in system 10. The medical device system 10 typically includes provisions for interrogating these devices through a wireless or other communication protocol using an external "instrument" that includes an external-to-the-patient antenna and software/firmware interface to collect data.

In the illustrated example, IMD 15A is an insertable cardiac monitor (ICM) capable of sensing and recording cardiac electrogram (EGM) signals, (also referred to as an ECG or EKG electrocardiogram when external electrodes are placed on the skin), from a position outside of the heart 13 via electrodes. In some examples, IMD 15A includes or is coupled to one or more additional sensors, such as accelerometers, that generate one or more signals that vary based on patient motion and/or posture, blood flow, or respiration. IMD 15A may monitor a physiological parameter indicative of patient state, such as posture, heart rate, activity level, and/or respiration rate. IMD 15A may be implanted outside of the thorax of patient 12, e.g., subcutaneously or submuscularly, such as the pectoral location illustrated in FIG. 1. In some examples, IMD 15A may take the form of a Reveal LINQ® ICM, available from Medtronic plc, of Dublin, Ireland.

In various examples, to keep the size dimensions, in particular a thickness dimension, for IMD 15A as small as possible, a planar antenna 17 (receiving/transmitting antenna), for example an antenna comprising a conductive trace printed on a planar surface such as a substrate, may be provided within IMD 15A. The advantage of a planar design, as compared to for example a three-dimensional antenna, is that the uni-directional or planar format of the antenna may take up less space within the device, and may be more easily packaged into the device when size and space are of concern, for example with respect to IMD 15A. One disadvantage associated with the planar antenna may be that coupling efficiencies with respect to receiving power transmitted from outside patient 12 to the antenna 17 may be orientation specific. For example, the orientation of the electromagnetic and magnetic fields being imposed on IMD 15A relative to the antenna 17 has an effect on the efficiency of the transfer of power from the electromagnetic and magnetic fields imposed on ID 15A by inducing corresponding electromagnetic energy in antenna 17. The orientation of IMD 15A may not be precisely known, or may shift at some point in time after implantation into patient 12, including due to motion of the patient or patient's heart. A change in orientation of IMD 15A may cause issues, including variations in the power transfer efficiencies during recharging of a power source and/or a battery located within IMD 15A.

As illustrated in FIG. 1, ID 15B may be implanted, as one example, within a pulmonary artery 14 of patient 12, and may include pressure sensing circuitry configured to measure the cardiovascular pressure within the pulmonary artery 14 of patient 12. In some examples, IMD 15B may be a part of sensor assembly. In some examples, IMD 15B may include wireless communication circuitry, such as tissue conduction communication (TCC) circuitry or an antenna, configured to receive signals, e.g., trigger signals from IMD 15A. The pressure sensing circuitry of IMD 15B may be configured to measure the cardiovascular pressure of patient 12 in response to receiving the trigger signal. IMD 15B may be configured to transmit the measured pressure values to IMD 15A by wireless communication. For example, IMD 15B may transmit measurements and data acquired by IMD 15B related to pulmonary artery pressure and other information generated by IMD 15B to IMD 15A. In some examples, IMD 15B may transmit data and other information to an external device, such as external device 11. External device 11 may also be referred to as an "instrument," which may include any of the devices described throughout the disclosure as devices located externally to the patient and configured to communicate with an implanted medical device, and in some examples may be included as part of a recharging system configured to recharge the battery or other power source provided within IMD 15A and/or IMD 15B.

Because IMD 15B may be implanted within the pulmonary artery 14 of patient 12, there is an interest in miniaturizing IMD 15B to the extent possible while maintaining the desired functionality of the device. As such, in a similar manner as described above with respect to IMD 15A, there may be a need to limit the arrangement and space allocated for the antenna provided within IMD 15B to perform the communication functions, for example as described above, for IMD 15B. Such an antenna may, in some examples, additionally or alternatively may be used by IMD 15B to receive the energy inductively used to recharge the power source provided within IMD 15B based on electromagnetic and magnetic fields imposed on IMD 15B. The limitation of size and space for IMD 15B may require use of an antenna, such as a planar antenna, that is subject to coupling inefficiencies based on the distance from the source, for example a coil or pair of coils located externally to patient 12 (not shown in FIG. 1), which is/are configured to provide the inductive charge, and also with respect to the orientation of the antenna in IMD 15B relative to the orientation of the fields being provided by the external coil(s).

The systems, devices, and methods described in this disclosure provide for charging of these internal, and in some instances deeply implanted devices, such as IMD 15A and IMD 15B, even when these devices include planar antennas or other configurations of antennas that are orientation specific with respect to coupling efficiencies between the antenna and the orientation of an arrangement of coil(s) being used to provide the electromagnetic and magnetic fields being imposed on the device for the purpose of inductively recharging a power source, such as a battery, located within the device being inductively charged.

In various examples, IMD 15A and IMD 15B are configured to wirelessly communicate with external device 11.

External device 11 may be a computing device, e.g., used in a home, ambulatory, clinic, or hospital setting, to wirelessly communicate with IMD 15A and/or IMD 15B. External device 11 may be coupled to a remote patient monitoring system, such as Carelink®, available from Medtronic plc, of Dublin, Ireland. External device 11 may be, as examples, a programmer, external monitor, or consumer device, e.g., smart phone. External device 11 may be used to program commands or operating parameters into IMD 15A and/or IMD 15B for controlling the functioning of these devices. External device 11 may be used to interrogate IMD 15A and/or IMD 15B to retrieve data, including device operational data as well as physiological or neurological data accumulated in memory in either of these devices. The interrogation may be automatic, e.g., according to a schedule, or in response to a remote or local user command. One or more of these external devices may also be referred to as an "instrument" or as a group of instruments.

In various examples, communications provided from IMD 15A and/or IMD 15B may include data and/or other information related to the inductive charging of these devices. For example, when an electromagnetic or magnetic field is imposed on IMD 15A and 15B for the purpose of inductively charging these devices, information related to the coupling efficiency of inductive coupling to the device, and/or for example the state of charge (e.g., percent of charge relative to a full charge), may be transmitted from one or both of IMD 15A and/or IMD 15B to external device 11 as part of the recharging process. Other information, such as time to full charge, rate of recharge, and temperature of the device may also be provided as information that is transmitted from the device(s) being recharged. In some examples, this information may be used to adjust parameters, such as the field strength of the fields used to induce the energy in the antenna(s) for recharging of IMD 15A and/or IMD 15B, or for example to provide information used to re-orient the coils and/or reconfigure the electrical parameters being used to energize the coils that are providing the fields used for the induced recharging energy provided to these devices.

In addition, information may be provided by IMD 15A and/or IMD 15B that is indicative of the level of the recharging of one or both of IMD 15A and/or IMD 15B that has been achieved or completed, which may then be used to determine when to further regulate, stop, or otherwise terminate the recharging process. For example, during the recharging process IMD 15A and/or IMD 15B may transmit data or other information indicating that the device, respectively, is fully recharged. The indication may then be used by the external devices providing the fields (not show in FIG. 1) to stop the charging process, which may include removing the fields used to recharge IMD 15A and/or IMD 15B from being imposed on these devices. In addition, monitoring the temperature of the device may be important, as overheating of an implanted device as a result of the recharging process may damage the device, or present a safety issue for the patient. Adjustments to the intensities of the fields being imposed on the device, and/or termination of the recharging process altogether may be made based on the monitored temperature of the device being recharged as a part of the recharging process. Examples of communication techniques used by IMD 15A and/or 15B and external device 11 are not limited to any particular communication technique or communication protocol, and in some examples include tissue conductance communication (TCC) or RF telemetry, which may be an RF link established via Bluetooth®, WiFi, or medical implant communication service (MICS).

In various examples, one or more additional sensor circuits may be located outside of or separately located relative to the IMD 15A. These one or more additional sensor circuits are illustratively represented by sensor circuits 18. Sensor circuits 18 may include a single sensor circuit configured to sense a particular physiological or neurological parameter associated with patient 12, or may comprise a plurality of sensor circuits, which may be located at various and/or different positions relative to patient 12 and/or relative to each other, and are configured to sense one or more physiological parameters associated with patient 12.

For example, sensor circuits 18 may include a sensor operable to sense a body temperature of patient 12 in a location of the sensor circuits 18, or at the location of the patient where a temperature sensor coupled by a lead to sensor circuits 18 is located. In another example, sensor circuits 18 may include a sensor configured to sense motion, such as steps taken by patient 12, and/or a position or a change of posture of patient 12. In various examples, sensor circuits 18 may include a sensor that is configured to detect breaths taken by patient 12. In various examples, sensor circuits 18 may include a sensor configured to detect heartbeats of patient 12. In various examples, sensor circuits 18 may include a sensor that is configured to measure systemic blood pressure of patient 12.

In some examples, one or more of the sensors comprising sensor circuits 18 may be implanted within patient 12, that is, implanted below at least the skin level of the patient. In some examples, one or more of the sensors of sensor circuits 18 may be located externally to patient 12, for example as part of a cuff or as a wearable device, such as a device imbedded in clothing that is worn by patient 12. In various examples, sensor circuits 18 may be configured to sense one or more physiological parameters associated with patient 12, and to transmit data corresponding to the sensed physiological parameter or parameters to ID 15A, as represented by the lightning bolt coupling sensor circuits 18 to IMD 15A. Transmission of data from sensor circuits 18 to IMD 15A in various examples may be performed via wireless transmission, as would be understood by those of skill in the art. In various examples, transmission of data from one or more of the sensors comprising sensor circuits 18 to IMD 15A may be performed by a wired connection between the sensor circuits 18 and IMD 15A. When one or more of sensors 18 are implanted devices that are implanted within patient 12, the systems, devices, and recharging techniques as described throughout this disclosure may be used to also recharge a power source, such as a battery, located within the implanted sensor(s) and configured to provide power to the sensor.

In various examples, IMD 15A and/or IMD 15B may communicate wirelessly to an external device (e.g., an instrument or instruments) other than or in addition to external device 11, such as transceiver 16 shown in FIG. 1. In various examples, external device 11 is a programming device, such as a handheld programmer, or for example a computing device used to program and/or interrogate IMD 15A and/or IMD 15B. In various examples, external transceiver 16 as shown in FIG. 1 is an access point, such as access point 105 illustrated and described with respect to FIG. 7, that provides a wireless communication link between IMD 15A and/or IMD 15B and network 107, also illustrated and described with respect to FIG. 7. In various examples, transceiver 16 acts as communication circuitry 324 of recharging system 300 shown in FIG. 13, wherein communication circuitry 324 is configured to communicate with IMD 15A, and/or IMD 15B, during the recharging process of these devices, as further described below. Examples of communication techniques used by any of the devices described above with respect to FIG. 1 and transceiver 16 may include radiofrequency (RF) telemetry, which may be an RF link established via Bluetooth®, WiFi, or medical implant communication service (MICS).

Figure 2:
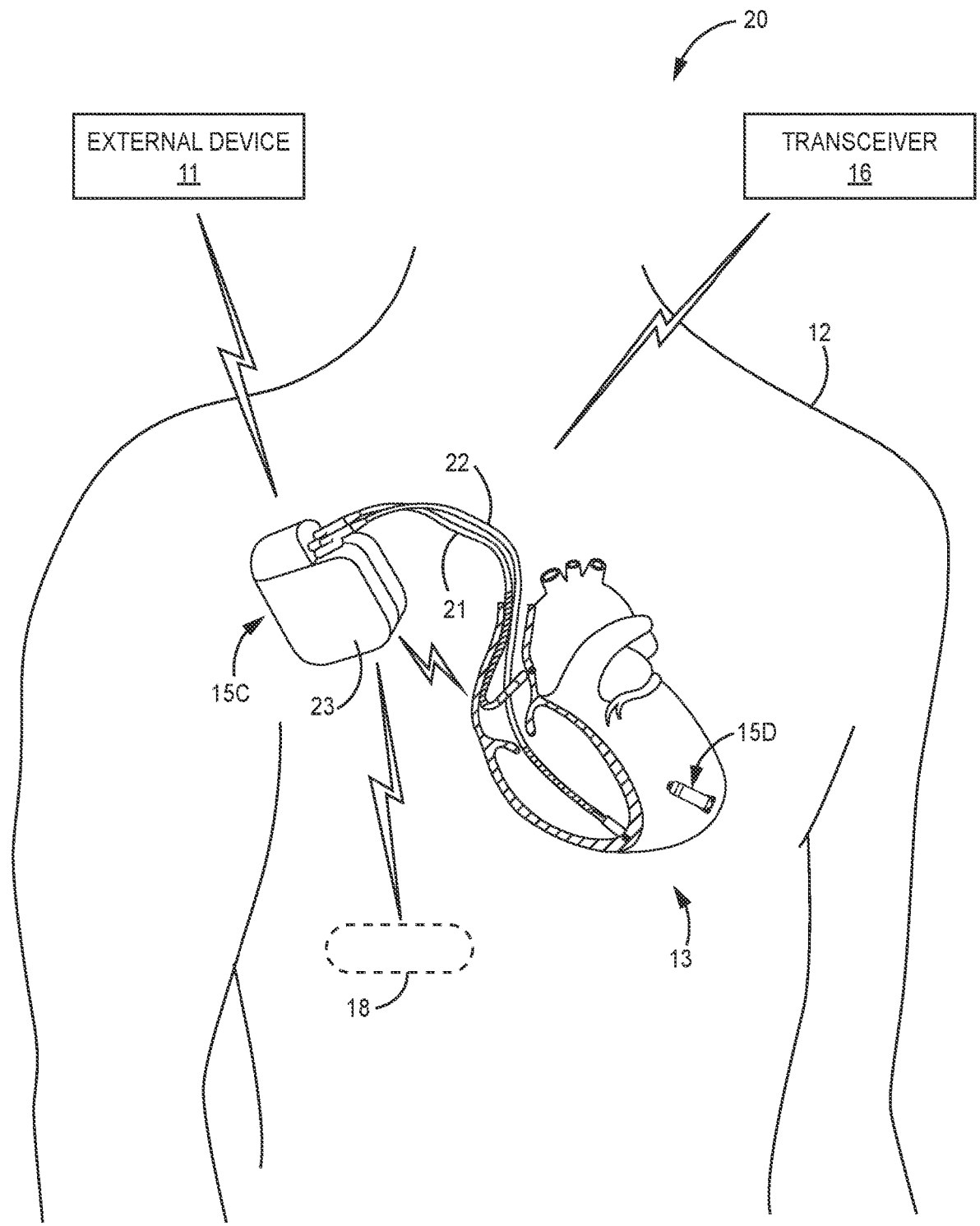
FIG. 2 is a conceptual drawing illustrating another example medical device system in conjunction with a patient according to various examples described in this disclosure.

FIG. 2 is a conceptual drawing illustrating another example medical device system 20 in conjunction with a patient 12 according to various examples described in this disclosure. The systems, devices, and techniques described in this disclosure provide for charging of these internal, and in some instances deeply implanted devices, such as IMD 15C, IMD 15D, and/or sensors 18, as illustrated and described with respect to FIG. 2. For purposes of this description, knowledge of cardiovascular anatomy is presumed, and details are omitted except to the extent necessary or desirable to explain the context of the techniques of this disclosure. The systems, devices, and techniques describe herein may provide efficient coupling for recharging power sources internal to IMD 15C, IMD 15D, and/or sensors 18. The advantages apply even when these devices are deeply implanted and/or include planar antennas or other configurations of antennas that are orientation specific with respect to coupling efficiencies between the antenna of the device being inductively recharged. In various examples, IMD 15C and/or IMD 15D may represent a defibrillator, a cardiac resynchronization pacer/defibrillator, or a pacemaker.

In the illustrated example, medical device system 20 includes an IMD 15C coupled to a ventricular lead 22 and an atrial lead 21. In various examples, IMD 15C is an implantable cardioverter-defibrillator (ICD) capable of delivering pacing, cardioversion and defibrillation therapy to the heart 13 of a patient 12. Ventricular lead 22 and atrial lead 21 are electrically coupled to IMD 15C, and extend into the heart 13 of patient 12. Ventricular lead 22 includes electrodes (not labeled in FIG. 2) positioned on the lead in the patient's right ventricle (RV) for sensing ventricular EGM signals and pacing in the RV. Atrial lead 21 includes electrodes (not labeled in FIG. 2) positioned on the lead in the right atrium (RA) of patient 12 for sensing atrial EGM signals and pacing in the RA. Ventricular lead 22 and/or atrial lead 21 may also include coil electrodes used to deliver cardioversion and defibrillation shocks. The term "anti-tachyarrhythmia shock" may be used herein to refer to both cardioversion shocks and defibrillation shocks. IMD 15C may use both ventricular lead 22 and atrial lead 21 to acquire cardiac electrogram (EGM) signals from patient 12 and to deliver therapy in response to the acquired data. Medical device system 20 is shown as having a dual chamber IMD configuration, but other examples may include one or more additional leads, such as a coronary sinus lead extending into the right atrium, through the coronary sinus and into a cardiac vein to position electrodes along the left ventricle (LV) for sensing LV EGM signals and delivering pacing pulses to the LV. In other examples, a medical device system may be a single chamber system, or otherwise not include atrial lead 21.

Processing circuitry, sensing circuitry, and other circuitry configured for performing the techniques described herein with respect to IMD 15C may be housed within a sealed housing 23. Housing 23 (or a portion thereof) may be conductive so as to serve as an electrode for pacing or sensing, or as an active electrode during defibrillation. As such, housing 23 is also referred to herein as "housing electrode" 23. Housing 23 may include one or more electrodes with a high-capacitance portion and a low-capacitance portion. The high-capacitance portion and the low-capacitance portion may be formed using two different materials.

IMD 15C may transmit EGM signal data and cardiac rhythm episode data, as well as data regarding delivery of therapy by IMD 15C, to an external device 11. In various examples, external device 11 is substantially similar to external device 11 as illustrated and described with respect to FIG. 1, and may provide any or all of the features and perform any or all of the functions illustrated and described throughout this disclosure with respect to external device 11, and any equivalents thereof. For example, external device 11 as illustrated in FIG. 2 may be a computing device, e.g., used in a home, ambulatory, clinic, or hospital setting, to communicate with IMD 15C via wireless telemetry. External device 11 may be coupled to a remote patient monitoring system, such as Carelink®, available from Medtronic plc, of Dublin, Ireland. External device 11 may be, as examples, a programmer, external monitor, or consumer device, e.g., smart phone.

External device 11 may be used to program commands or operating parameters into IMD 15C for controlling its functioning, e.g., when configured as a programmer for IMD 15C. External device 11 may be used to interrogate IMD 15C to retrieve data, including device operational data as well as physiological data accumulated in IMD 15C memory. The interrogation may be automatic, e.g., per a schedule, or in response to a remote or local user command. Examples of communication techniques used by IMD 15C and external device 11 may include TCC and RF telemetry, which may be an RF link established via Bluetooth®, WiFi, or MICS.

In addition, system 20 may include transceiver 16 wirelessly coupled to communicate with IMD 15C. In some examples, transceiver 16 is transceiver 16 as illustrated and described above with respect to FIG. 1, and may provide some or all of the features and perform any or all of the functions illustrated and described with respect to transceiver 16 and/or external device 11, and any equivalents thereof, with respect to system 20.

In various examples, one or more additional sensor circuits may be located outside of or separately located relative to the IMD 15C. These one or more additional sensor circuits are illustratively represented by sensor circuits 18. Sensor circuits 18 may include a single sensor circuit configured to sense a particular physiological parameter associated with patient 12, or may comprise a plurality of sensor circuits, which may be located at various and/or different positions relative to patient 12 and/or relative to each other, and may be configured to sense one or more physiological parameters associated with patient 12. In various examples, sensor circuits 18 may include one or more of the sensors 18 as illustrated and described above with respect to FIG. 1, and may provide any of the features and perform any of the functions described throughout this disclosure with respect to sensors 18, but with respect to IMD 15C and system 20.

As illustrated in FIG. 2 the medical device system 20 includes an intracardiac pacing device IMD 15D. In the illustrated example, IMD 15D is implanted in the left-ventricle of patient 12, e.g., internal to the heart 13 of patient 12. In some examples, one or more IMDs like IMD 15D (not shown in FIG. 2) may additionally or alternatively be implanted within other chambers of heart 13, or attached to the heart epicardially. IMD 15D may be configured to sense electrical activity of heart 13 and deliver pacing therapy, e.g., bradycardia pacing therapy, cardiac resynchronization therapy (CRT), anti-tachycardia pacing (ATP) therapy, and/or post-shock pacing, to heart 13. IMD 15D may be attached to an interior wall of heart 13 via one or more fixation elements (not shown in FIG. 2), that penetrate the cardiac tissue. These fixation elements may secure IMD 15D to the cardiac tissue and retain an electrode (e.g., a cathode or an anode) on the housing of IMD 15D in contact with the cardiac tissue. In addition to delivering pacing pulses, IMD 15D may be capable of sensing electrical signals using the electrodes carried on the housing of IMD 15D. These electrical signals may be electrical signals generated by cardiac muscle and indicative of depolarizations and repolarizations of heart 13 at various times during the cardiac cycle.

In some examples, IMP 15C and IMD 15D may both be configured to deliver pacing therapy. In such examples, IMD 15C and IMD 15D may delivery pacing therapy to the right and left ventricles of heart 13, respectively, to provide CRT pacing. Additionally, IMD 15C and IMP 15D may both be configured to detect tachyarrhythmias, and deliver anti-tachyarrhythmia therapy. IMP 15C and IMD 15D may be configured to coordinate their cardiac rhythm detection and treatment activities. In some examples, IMP 15C and IMP 15D may engage in wireless communication with each other to facilitate such coordinated activity. The wireless communication may be via TCC, and may be one-way communication in which one device is configured to transmit communication messages and the other device is configured to receive those messages, or two-way communication in which each device is configured to transmit and receive communication messages.

For the remainder of the disclosure, a general reference to a medical device system may refer collectively to include any examples of medical device systems 10 and 20, a general reference to IMD 15 may refer collectively to include any examples of IMD 15A, IMD 15B, IMD 15C and IMD 15D, a general reference to sensor circuits may refer collectively to include any examples of sensor circuits 18, a general reference to external device may refer collectively to include any examples of external devices 11, and a general reference to a transceiver may refer collectively to any examples of transceiver 16.

Figure 3:
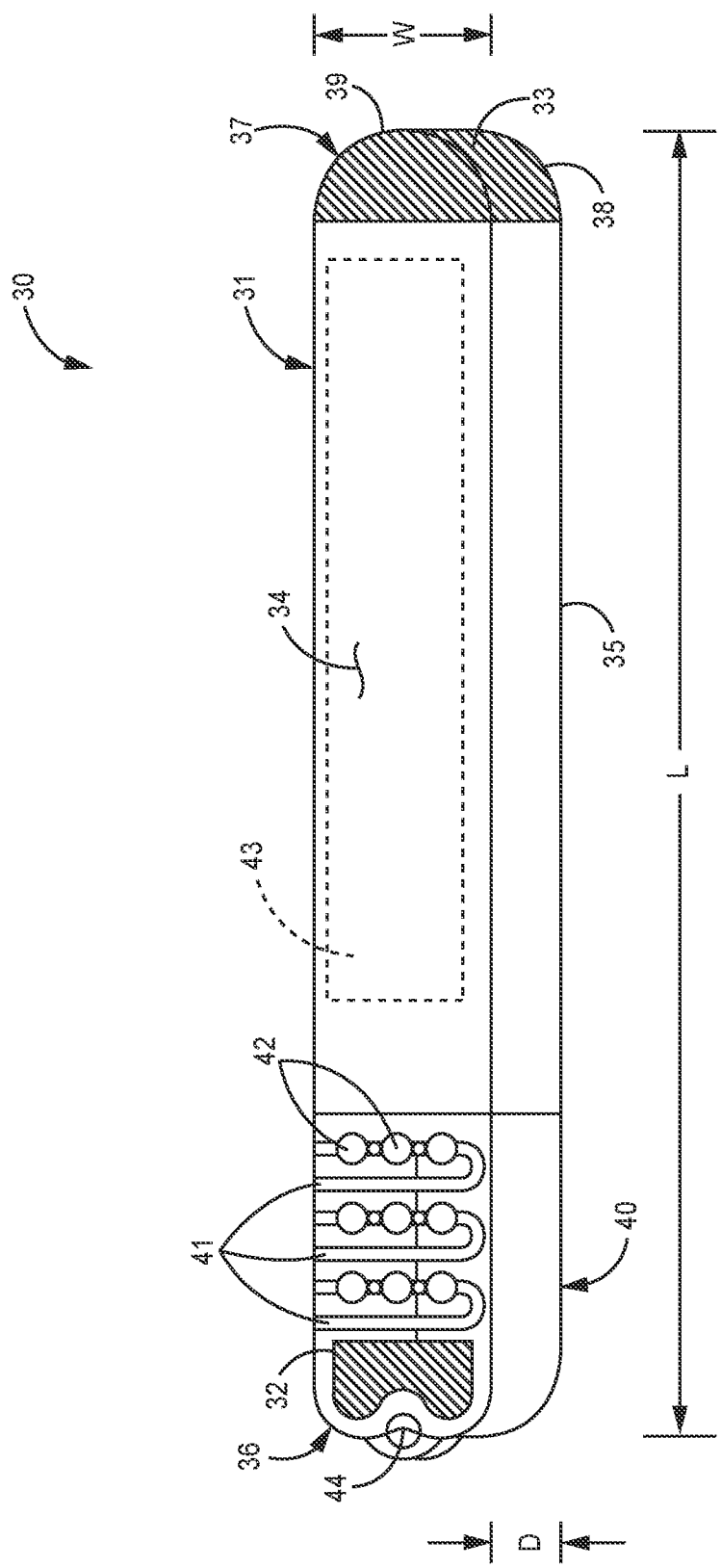
FIG. 3 is a conceptual drawing illustrating an example configuration of an implantable medical device according to various examples described in this disclosure.

FIG. 3 is a conceptual drawing illustrating an example configuration of an implantable medical device (IMD 30) according to various examples described in this disclosure. IMD 30 in some examples is IMD 15A as illustrated and described with respect to FIG. 1. IMD 30 may be an example of an implantable medical device that may be inductively recharged using the systems, devices, and techniques described in this disclosure. In the example shown in FIG. 3, IMD 30 may be an implantable loop recorder diagnostic device, such as the Medtronic Reveal LINQ® Insertable Cardiac Monitor developed by Medtronic, plc, of Dublin, Ireland. IMD 30 may be embodied as a monitoring device having housing 31, proximal electrode 32 and distal electrode 33.

Housing 31 may further comprise first major surface 34, second major surface 35, proximal end 36, and distal end 37. Housing 31 encloses electronic circuitry located inside the IMD 30, and protects the circuitry contained therein from body fluids when IMD 30 is implanted in a patient. Electrical feedthroughs may provide electrical connection of electrodes 32 and 33 or, in some examples, electrode 33 may comprise an uninsulated portion of an electrically conductive housing 31. A power source 43, such as battery is provided within IMD 30, which provides power to the electronic circuitry of IMD 30, and may at some point need to be recharged after IMD 30 has been implanted in a patient without the need to remove and re-implant IMD 30. The inductive recharging devices, systems, and methods described in this disclosure are configurable to provide inductive recharging of the power source 43 while IMD 30 remains implanted in a patient.

In the example shown in FIG. 3, IMD 30 may be defined by a length L, a width W, and thickness or depth D and in some examples in the form of an elongated rectangular prism wherein the length L is much larger than the width W, which in turn is larger than the depth D. In one example, the geometry of the IMD 30—in particular a width W greater than the depth D—is selected to allow IMD 30 to be inserted under the skin of the patient using a minimally invasive procedure and to remain in the desired orientation during insertion. For example, the device shown in FIG. 3 includes radial asymmetries (notably, the rectangular/prismatic shape) along the longitudinal axis that maintains the device in the proper orientation following insertion. In one example, the spacing between proximal electrode 32 and distal electrode 33 may range from thirty millimeters (mm) to fifty-five mm, thirty-five mm to fifty-five mm, and from forty mm to fifty-five mm, and may be any range or individual spacing from twenty-five mm to sixty mm.

In addition, IMD 30 may have a length L that ranges from thirty mm to about seventy mm. In other examples, the length L may range from forty mm to sixty mm, forty-five mm to sixty mm, and may be any length or range of lengths between about thirty mm and about seventy mm. In addition, the width W of major surface 34 may range from three mm to ten mm, and may be any single or range of widths between three mm and ten mm. The thickness of depth D of IMD 30 may range from two mm to nine mm. In other examples, the depth D of IMD 30 may range from two mm to five mm and may be any single or range of depths from two mm to nine mm.

In addition, IMD 30 according to an example of the present disclosure has a geometry and size designed for ease of implant and patient comfort. Examples of IMD 30 described in this disclosure may have a volume of three cubic centimeters (cm) or less, one-and-a-half cubic cm or less, or any volume between three and one-and-a-half cubic centimeters. In addition, in the example shown in FIG. 3, proximal end 36 and distal end 37 are rounded to reduce discomfort and irritation to surrounding tissue once inserted under the skin of the patient. IMD 30, including instrument, introducer, and method for inserting IMD 30 are described, for example, in U.S. Patent Application Publication No. 2014/0276928, incorporated herein by reference in its entirety.

In the example shown in FIG. 3, once inserted within the patient, the first major surface 34 faces outward, toward the skin of the patient while the second major surface 35 is located opposite the first major surface 34. Consequently, the first and second major surfaces may face in directions along a sagittal axis of patient 12 (see FIG. 1), and this orientation may be consistently achieved upon implantation due to the dimensions of IMD 30. Additionally, an accelerometer, or axis of an accelerometer, may be oriented along the sagittal axis.

Proximal electrode 32 and distal electrode 33 are used to sense cardiac signals, e.g. ECG signals, intra-thoracically or extra-thoracically, which may be sub-muscularly or subcutaneously. ECG signals may be stored in a memory of the IMD 30, and ECG data may be transmitted via integrated antenna 41 (receive antenna) to another medical device, which may be another implantable device or an external device, such as external device 11 illustrated in FIG. 1. Referring again to FIG. 3, in some examples electrodes 32 and 33 may additionally or alternatively be used for sensing any bio-potential signal of interest, which may be, for example an electrogram (EGM), electroencephalogram (EEG) signal, electromyography (EMG) signal, or a nerve signal, from any implanted location. In some examples, IMD 30 may be implanted cranially in a location within the head areas of a patient, and proximal electrode 32 and distal electrode 33 are used to sense neurological signals.

In the example shown in FIG. 3, proximal electrode 32 is in close proximity to the proximal end 36, and distal electrode 33 is in close proximity to distal end 37. In this example, distal electrode 33 is not limited to a flattened, outward facing surface, but may extend from first major surface 34 around rounded edges 38 and/or end surface 39 and onto the second major surface 35 so that the electrode 33 has a three-dimensional curved configuration. In the example shown in FIG. 3, proximal electrode 32 is located on first major surface 34 and is substantially flat, outward facing. However, in other examples proximal electrode 32 may utilize the three-dimensional curved configuration of distal electrode 33, providing a three-dimensional proximal electrode (not shown in this example). Similarly, in other examples distal electrode 33 may utilize a substantially flat, outward facing electrode located on first major surface 34 similar to that shown with respect to proximal electrode 32. The various electrode configurations allow for configurations in which proximal electrode 32 and distal electrode 33 are located on both first major surface 34 and second major surface 35.

In other configurations, such as that shown in FIG. 3, only one of proximal electrode 32 and distal electrode 33 is located on both major surfaces 34 and 35, and in still other configurations both proximal electrode 32 and distal electrode 33 are located on one of the first major surface 34 or the second major surface 35 (i.e., proximal electrode 32 located on first major surface 34 while distal electrode 33 is located on second major surface 35). In another example, IMD 30 may include electrodes on both major surface 34 and 35 at or near the proximal and distal ends of the device, such that a total of four electrodes are included on IMD 30. Electrodes 32 and 33 may be formed of a plurality of different types of biocompatible conductive material, e.g. stainless steel, titanium, platinum, iridium, or alloys thereof, and may utilize one or more coatings such as titanium nitride or fractal titanium nitride.

In the example shown in FIG. 3, proximal end 36 includes a header assembly 40 that includes one or more of proximal electrode 32, integrated antenna 41, anti-migration projections 42, and/or suture hole 44. Integrated antenna 41 is located on the same major surface (i.e., first major surface 34) as proximal electrode 32 and is also included as part of header assembly 40.

Antenna 41 may be coupled to recharging circuitry (not shown in FIG. 3), wherein antenna 41 is configured to enable inductive power transfer of energy inductively generated in the antenna 41 by electromagnetic fields imposed on the antenna for the purpose of recharging, by the recharging circuitry, the power source 43 provided within IMD 30. Antenna 41 may also be configured to communication circuitry and/or processing circuitry included as part of the electronic circuitry included within IMD 30, wherein the electronic circuitry is configured to generate and output data transmitted by antenna 41 to one or more devices external to IMD 30 that corresponds to a level of coupling efficiency occurring between the recharging system and IMD 30 during a recharging session being performed to recharge battery 43.

In the example shown in FIG. 3, anti-migration projections 42 are located adjacent to integrated antenna 41 and protrude away from first major surface 34 to prevent longitudinal movement of the device. In the example shown in FIG. 3 anti-migration projections 42 include a plurality (e.g., nine) of small bumps or protrusions extending away from first major surface 34. As discussed above, in other examples anti-migration projections 42 may be located on the opposite major surface as proximal electrode 32 and/or integrated antenna 41. In addition, in the example shown in FIG. 3 header assembly 40 includes suture hole 44, which provides another means of securing IMD 30 to the patient to prevent movement following insertion. In the example shown, suture hole 44 is located adjacent to proximal electrode 32. In one example, header assembly 40 is a molded header assembly made from a polymeric or plastic material, which may be integrated or separable from the main portion of IMD 30.

Figure 4A:
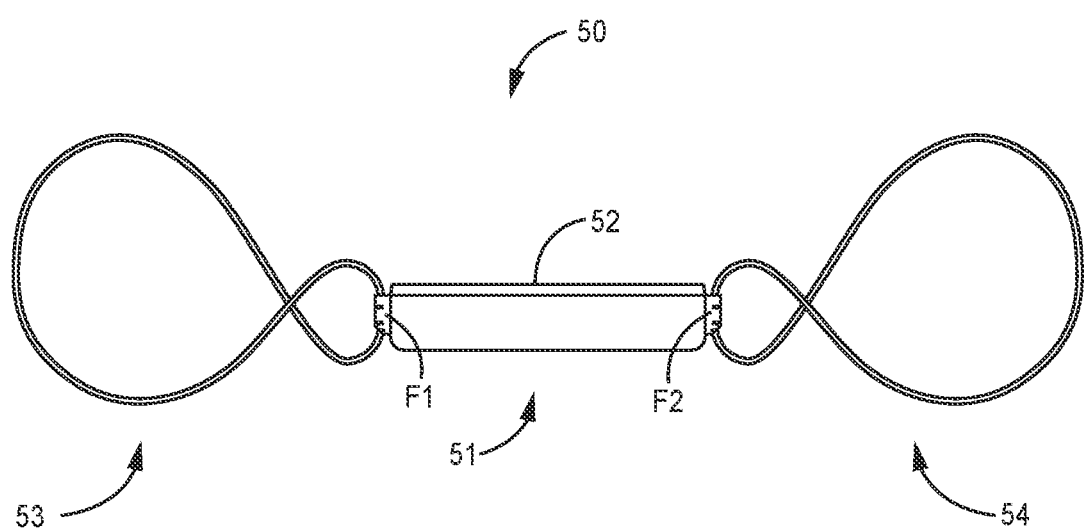
FIGS. 4A and 4B illustrate various views of a pressure sensing device in accordance with examples as described in this disclosure.
Figure 4B:
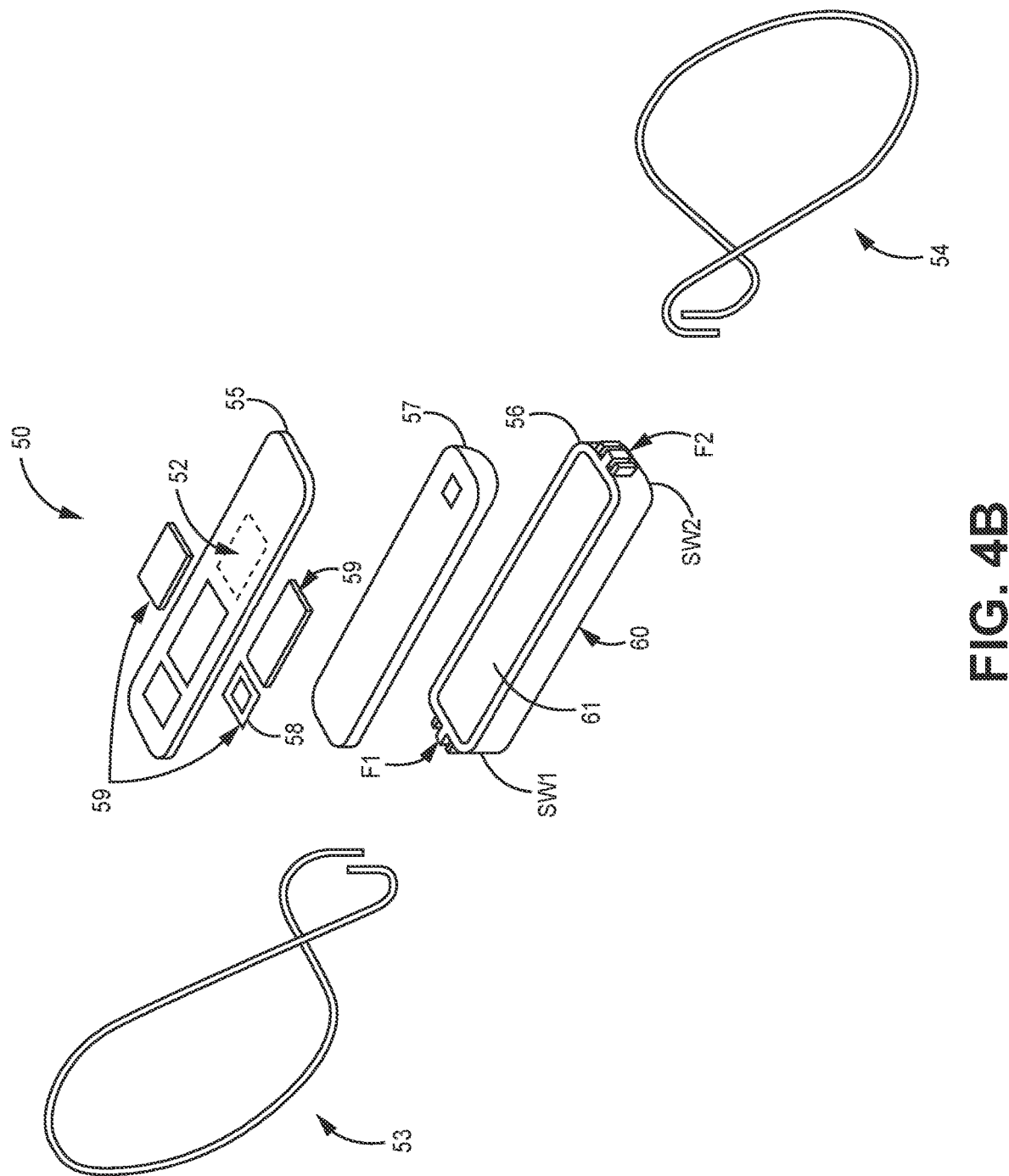

FIGS. 4A and 4B illustrate various views of a pressure sensing device 50 in accordance with examples as described in this disclosure. Device 50 in some examples is IMD 15B as illustrated and described with respect to FIG. 1. Device 50 may be an example of an implantable medical device that may be inductively recharged using the systems, devices, and methods described in this disclosure. As illustrated in FIGS. 4A and 4B, device 50 includes a capsule 60. Capsule 60 may include an elongate body that defines an interior cavity 61. The interior cavity 61 of the capsule 60 is sized and shaped to contain the battery 57, and electronics and sensor components 59 of the sensor circuit 51, and an antenna 58 coupled to a communication circuit of the electronic components. In some examples, antenna 58 is a planar antenna designed to save space within device 50, but may also be orientation specific with respect to coupling to electromagnetic and magnetic fields imposed on pressure sensing device 50 for the purpose of inductively recharging battery 57.

The capsule 60 is preferably designed with shapes that are easily accepted by the patient's body while minimizing patient discomfort. For example, the body of capsule 60 may be formed in a cylindrical shape with cylindrical sidewalls. In various examples, this cylindrical shape of the sidewalls is used to enable a cylindrical recharge/receive coil for inductive power transfer to recharge the power source provided within pressure sensing device 50. Other non-cylindrical configurations may be employed, however, in which case the corners and edges may be designed with generous radii to present a capsule having smoothly contoured surfaces. In the depicted example, the body of capsule 60 is formed as a generally rectangular structure, which means that the outline of the shape of capsule 60 resembles a rectangle with the edges and corners that are contoured.

In some examples, capsule 60 is formed having two sections 55, 56, one of which (e.g., section 55) can contain the sensor element 52, such as a pressure sensing diaphragm, of sensor circuit 51, while the other section (e.g., section 56) can contain the battery 57, and electronics and sensor components 59 of the sensor circuit 51. In some examples, capsule 60 is formed from one or more biocompatible materials that can be hermetically sealed when the sections 55, 56 are joined. A number of such biocompatible materials may be employed, as will be understood by those familiar with the art, including metals and biocompatible plastics. For example, the sections 55, 56 may be formed from unalloyed titanium with an American Society for Testing and Materials (ASTM) grade 1 to grade 4 or an alloyed titanium (grade 5) that includes aluminum and vanadium. or grade 23 ELI (extra low interstitial) or grade 9.

For examples in which the sections are metal, the metal material of the capsule 60 may optionally be selected to be compatible with the fixation assembly 53, 54, material so as to permit the fixation assembly 53, 54 to be securely-coupled to the capsule 60. In other examples, the capsule 60 along with the fixation assembly 53, 54 may be integrally formed from one or more of the same or distinct materials. In some examples, the capsule 60, as well as some portions of the fixation member 53, 54, may be encapsulated in a biologically inert dielectric barrier material such as a film of silicone or poly(p-xylylene) polymer sold under the trade name PARYLENE.

As shown in FIG. 4B, capsule 60 may include fasteners F1, F2, located on first side wall SW1 and second side wall SW2, respectively, that define channels for reception of a segment of the fixation assemblies 53 and 54. respectively. The received segment may include a portion along a length of the fixation assemblies 53, 54, or a free end of the fixation assemblies 53, 54. The fasteners F1, F2, are coupled to an exterior of the capsule 60, or in some examples, formed integrally with the capsule 60. For example, as shown in the example of FIG. 4B, the fasteners F1, F2, are provided at an exterior of the capsule 60 at the lateral sidewalls SW1, SW2, respectively.

In some examples, the fasteners are formed as pairs of tabs that are arranged to define one or more channel(s) for receiving one or more segment(s) of the fixation assemblies 53, 54. Each fastener can include a pair of tabs that are aligned longitudinally as described, for example, in U.S. Pat. No. 8,864,676 to Beasley et al. which is incorporated herein by reference in its entirety. The fasteners may be coupled to the capsule 60 through welding, for example. The fasteners may be formed integrally with the capsule 60, preferably on opposing ends of the capsule. However, the description of the fasteners F1, F2, is not intended to be limiting, and rather, it is provided to explain the context of the disclosure. In some examples of FIGS. 4A-4B, the fasteners F1, F2, are formed as tubular structures that define channels that are sized to receive a segment of each of the fixation assemblies 53, 54. In accordance with some examples, the fasteners F1, F2, may be formed as discrete components, such as tubes, for example, that can be coupled to the capsule 60 through coupling techniques such as welding or bonding agent such as glue or crimping. The fasteners may be formed integrally with the capsule 60. The fixation assemblies 53, 54, are coupled to the fasteners F1, F2, by any suitable coupling technique such as welding, crimping, bonding agent such as glue, frictional fit, etc.

The channels of fasteners F1, F2, may optionally be defined to receive a segment of the fixation assemblies 53, 54, in a snug fit arrangement to prevent relative movement between the capsule 60 and the fixation assembly. By way of dimensional example, the thickness of a cross section of fixation assemblies 53, 54, may be on the order of 0.006 inch for a round shape or 0.005 inch by 0.010 inch for a rectangular shape. In comparison, the diameter (or width) of the channel of each of the fasteners may be on the order of 0.010 inch to 0.025 inch. The free ends of each of the fixation assemblies 53, 54, may be oriented in opposing directions. For example, a first of the free ends may be oriented downward in relation to the lateral sidewall SW1, SW2, while the other end may be oriented upward in relation to the lateral sidewalls SW1, SW2. Among other things, such an orientation can provide a degree of load cancellation that minimizes load transfer to the sensor element 52.

Figure 5:
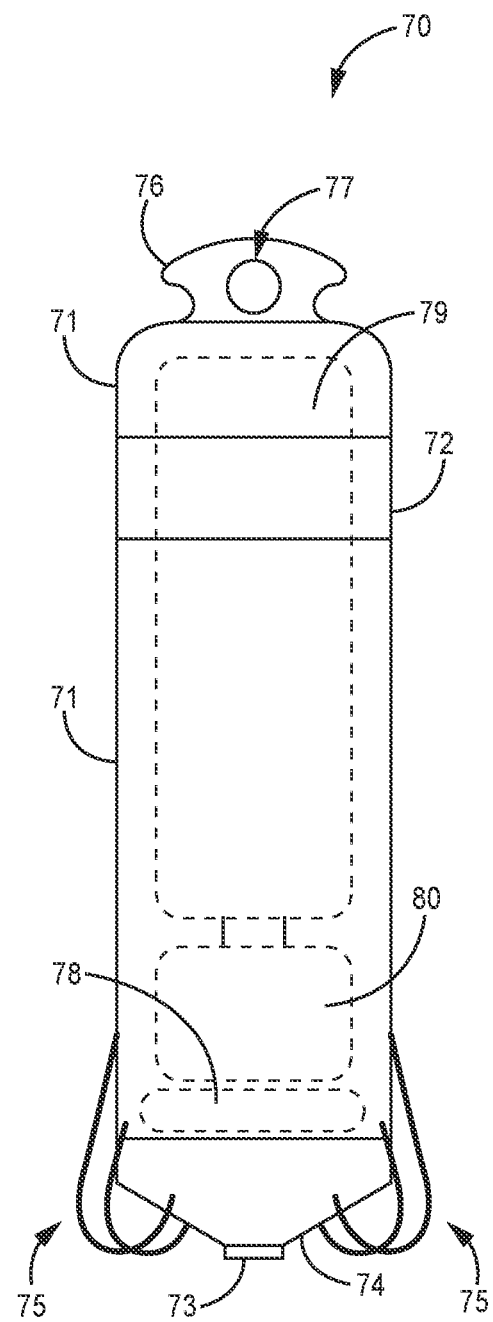
FIG. 5 is an illustrative diagram of an intracardiac pacing device in accordance with examples as described in this disclosure.

FIG. 5 is an illustrative diagram of an intracardiac pacing device 70 in accordance with examples as described in this disclosure. Device 70 in some examples is IMD 15D as illustrated and described with respect to FIG. 2. Device 70 may be configured to be implanted in the left ventricle of the heart of a patient, as depicted in FIG. 2, or within or on other chambers or locations of the heart. Referring again to FIG. 5, device 70 may be an example of an implantable medical device that may be inductively recharged using the systems, devices, and methods described in this disclosure. In some examples, device 70 is a Medtronic® Micra® Transcatheter Pacing System developed by Medtronic, plc, of Dublin, Ireland. As shown in FIG. 5, device 70 includes electronic circuitry 78 including communication circuitry coupled to an antenna 80, and a power source 79, for example a battery, that is coupled to the electronic circuitry and configured to provide power to the electronic circuitry. Communication circuitry of device 70 may be configured to provide wireless communication between device 70 and other devices, such as external device 11 and/or transceiver 16.

In addition, antenna 80 of device 70 may be configured to receive electrical energy imposed the device as electromagnetic fields, and to recharge battery 79 using energy inductively coupled to antenna 80 from these fields (also known as wireless power transfer). In order to save space and keep device 70 as small as possible, antenna 80 may be a planar antenna, such as an antenna formed as a conductive trace on a substrate, or a three-dimensional antenna. In various examples, antenna 80 may be orientation sensitive with respect to the orientation of antenna 80 relative to the orientation of the fields imposed on device 70 for the purpose of inductive power transfer, e.g., for recharging of battery 79 or for powering the circuitry within device 70.

Device 70 as illustrated in FIG. 5 includes case 71, cap 74, electrode 72, electrode 73, fixation mechanisms 75, flange 76, and opening 77. Together, case 71 and cap 74 may be considered the housing of device 70. In this manner, case 71 and cap 74 may enclose and protect the various electrical components, e.g., circuitry, within device 70. Case 71 may enclose substantially all of the electrical components, and cap 74 may seal case 71 and create the hermetically sealed housing of device 70. Although device 70 is generally described as including one or more electrodes, device 70 may typically include at least two electrodes (e.g., electrodes 72 and 73) to deliver an electrical signal (e.g., therapy such as cardiac pacing) and/or provide at least one sensing vector.

Electrodes 72 and 73 are carried on the housing created by case 71 and cap 74, respectively. In this manner, electrodes 72 and 73 may be considered leadless electrodes. In the example of device 70 shown in FIG. 5, electrode 73 is disposed on the exterior surface of cap 74. Electrode 73 may be a circular electrode positioned to contact cardiac tissue upon implantation. Electrode 72 may be a ring or cylindrical electrode disposed on the exterior surface of case 71. Both case 71 and cap 74 may be formed from electrically insulating material.

Electrode 73 may be used as a cathode and electrode 72 may be used as an anode, or vice versa, for delivering cardiac pacing such as bradycardia pacing, CRT, ATP, or post-shock pacing. However, electrodes 72 and 73 may be used in any stimulation configuration. In addition, electrodes 72 and 73 may be used to detect intrinsic electrical signals from cardiac muscle tissue. Tip electrode 73 may be configured to contact cardiac tissue such as an interior wall of the left ventricle of the heart of a patient.

Fixation mechanisms 75 may attach device 70 to cardiac tissue. Fixation mechanisms 75 may be active fixation tines, screws, clamps, adhesive members, or any other mechanisms for attaching a device to tissue. As shown in the example of FIG. 5, fixation mechanisms 75 may be constructed of a memory material, such as a shape memory alloy (e.g., nickel titanium), that retains a preformed shape. During implantation, fixation mechanisms 75 may be flexed forward to pierce tissue and allowed to flex back towards case 71. In this manner, fixation mechanisms 75 may be embedded within the target tissue.

Flange 76 may be provided on one end of case 71 to enable tethering or extraction of device 70. For example, a suture or other device may be inserted around flange 76 and/or through opening 77 and attached to tissue. In this manner, flange 76 may provide a secondary attachment structure to tether or retain device 70 within the heart if fixation mechanisms 75 fail. Flange 76 and/or opening 77 may also be used to extract device 70 once the device needs to be explanted (or removed) from the patient if such action is deemed necessary.

Figure 6:
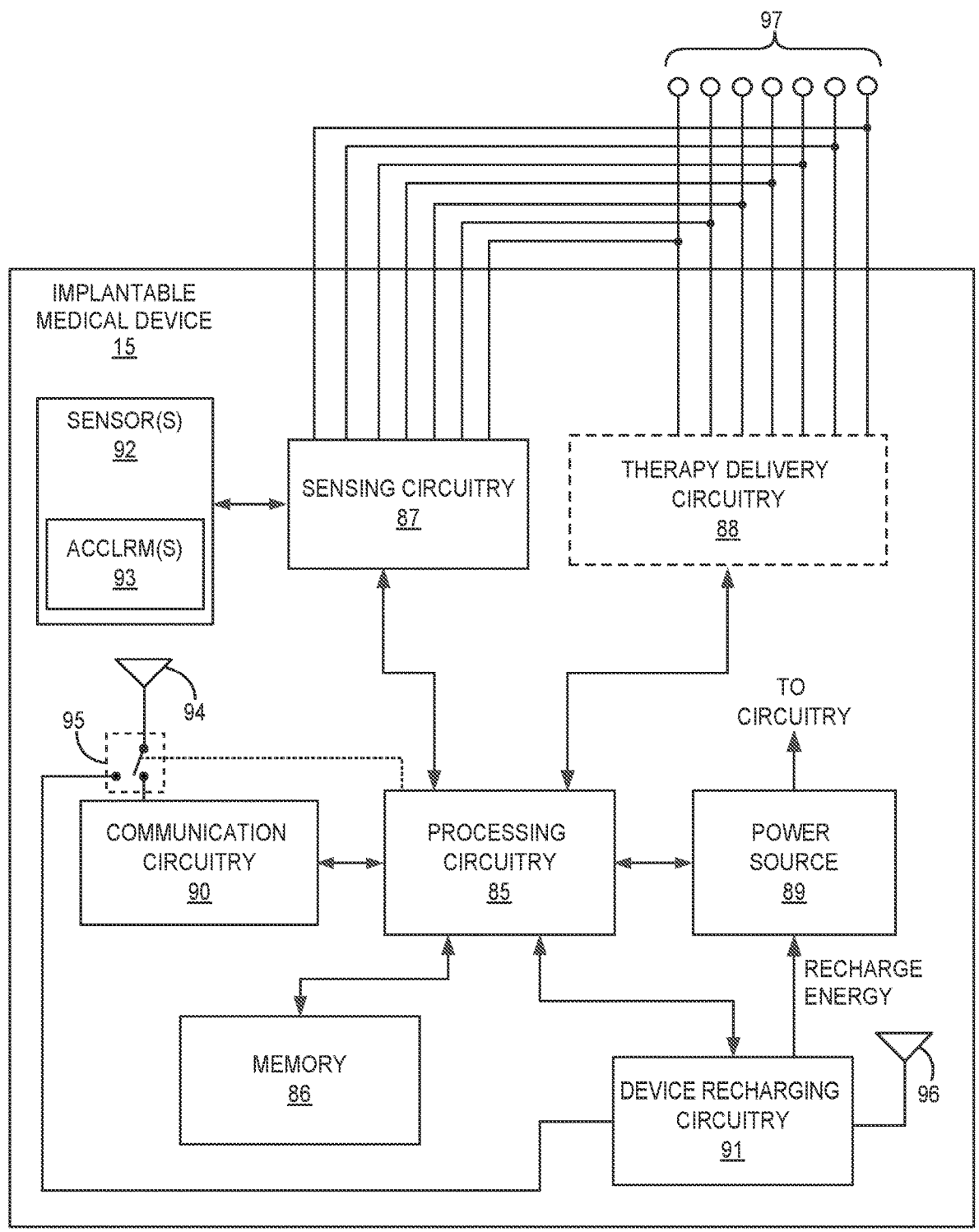
FIG. 6 is a functional block diagram illustrating an example configuration of an implantable medical device according to various examples described in this disclosure.

FIG. 6 is a functional block diagram illustrating an example configuration of an implantable medical device (IMD 15) according to various examples described in this disclosure. IMD 15 may correspond to any of IMD 15A (or IMD 30) and IMD 15B (or IMD 50) described and illustrated with respect to FIGS. 1, 3, and 4A-4B, and/or IMD 15C and ID 15D (or IMD 70) described and illustrated with respect to FIGS. 2 and 5, or another IMD, any of which may be configured to be rechargeable using the devices, systems, and methods as described in this disclosure. IMD 15 includes a power source 89 that may be coupled to the electronic circuitry provided in IMD 15, and may be configured to provide electrical power to these circuits. IMD 15 may be inductively rechargeable by providing electromagnetic energy to the IMD 15, wherein energy from these imposed fields may induce an electrical energy into antenna 94 coupled to communication circuitry 90 and to device recharging circuitry 91, or into an antenna 96 that may be provided in addition to antenna 94 and that when provided, is coupled directly to recharging circuitry 91. Device recharging circuitry 91 is coupled to power source 89, and is configured to receive electrical energy induced in antenna 94 (or in antenna 96 when provided) by one or more electromagnetic fields imposed on the antenna, and to regulate the energy to provide a level of electrical power that is provided to power source 89 for the purpose of recharging power source 89 and/or powering the other circuitry included as part of IMD 15.

Device recharging circuitry 91 may perform various energy conditioning functions to the energy inductively generated in antenna 94 (or antenna 96 when provided), for example by providing rectification, voltage level regulation, current level regulation, and/or other signal processing functions in order to generate the "recharging energy" provided to power source 89. However, antenna 94 (and/or antenna 96 when provided) may be orientation specific with respect to the coupling efficiency of the inductive charging of power source 89 based on the orientation of the antenna relative to the orientation of the coil or coils providing the electromagnetic fields imposed upon the antenna. Thus, IMD 15 may be configured to couple electromagnetic energy captured by an antenna (including, but not necessarily the telemetry antenna 94 or antenna 96), and direct the captured energy into a suitable rectifying circuit that delivers the electrical energy to an energy storage device such as a rechargeable battery. A switch 95, which may be a transistor switch, may be included in IMD 15 that is controlled to select whether the telemetry or the power recharge system is active, and whether antenna 94 is coupled to the communication circuitry 90 or the device recharging circuitry 91. In other examples, the second antenna 96 is coupled to device recharging circuitry 91, and is configured to receive the inductively coupled energy provided to antenna 96, and to provide the inductively coupled energy to device recharging circuit 91 to recharge power source 89.

In the illustrated example, IMD 15 includes processing circuitry 85 and an associated memory 86, sensing circuitry 87, therapy delivery circuitry 88, one or more sensors 92, and the communication circuitry 90 coupled to antenna 94 as describe above. However, IMD 15 need not include all of these components, or may include additional components. For example, IMD 15 may not include therapy delivery circuitry 88 in some examples. Memory 86 includes computer-readable instructions that, when executed by processing circuitry 85, causes IMD 15 and processing circuitry 85 to perform various functions attributed to IMD 15 and processing circuitry 85 as described herein, e.g., preparing information for transmission from IMD 15 regarding a level of charge present in a power source, such as a battery management system information (BMS), configured to provide information including a state of charge, and/or temperature information related to power source 89, e.g., a battery, located in IMD 15. The instructions may also cause IMD 15 and processing circuitry to determine a level of inductive coupling, e.g., energy level being generated in an antenna located in IMD 15 as a result of an electromagnetic field or fields being imposed on ID 15, and generate information related to this inductively received energy for transmission by the communication antenna or separate antenna and associated power conditioning circuitry of IMD 15.

Memory 86 may include any volatile, non-volatile, magnetic, optical, or electrical media, such as a random-access memory (RAM), read-only memory (ROM), non-volatile RAM (NVRAM), electrically-erasable programmable ROM (EEPROM), flash memory, or any other digital or analog media. Memory 86 may store threshold(s) for time of day, posture, heart rate, activity level, respiration rate, and other parameters. Memory 86 may also store data indicating cardiovascular pressure measurements.

Processing circuitry 85 may include fixed function circuitry and/or programmable processing circuitry. Processing circuitry 85 may include any one or more of a microprocessor, a controller, a digital signal processor (DSP), an application specific integrated circuit (ASIC), a field-programmable gate array (FPGA), or equivalent discrete or analog logic circuitry. In some examples, processing circuitry 85 may include multiple components, such as any combination of one or more microprocessors, one or more controllers, one or more DSPs, one or more ASICs, or one or more FPGAs, as well as other discrete or integrated logic circuitry. The functions attributed to processing circuitry 85 herein may be embodied as software, firmware, hardware or any combination thereof.

As illustrated, sensing circuitry 87 and therapy delivery circuitry 88 are coupled to electrodes 97. Electrodes 97 as illustrated in FIG. 6 may correspond to, for example, electrodes located on leads 21 and 22 of IMD 15C (FIG. 2), proximal electrode 32 and distal electrode 33 of IMD 15A (FIGS. 1 and 3), or electrodes 72 and 73 of IMD 15D (FIG. 1 and FIG. 5). Sensing circuitry 87 may monitor signals from a selected two or more of electrodes 97 in order to monitor electrical activity of heart, impedance, or some other electrical phenomenon. Sensing of a cardiac electrical signal may be done to determine heart rates or heart rate variability, or to detect arrhythmias (e.g., tachyarrhythmias or bradycardia) or other electrical signals. In some examples, sensing circuitry 87 may include one or more filters and amplifiers for filtering and amplifying a signal received from electrodes 97.

In some examples, sensing circuitry 87 may sense or detect physiological parameters, such as heart rate, blood pressure, respiration, and other physiological parameters associated with a patient. The resulting cardiac electrical signal may be passed to cardiac event detection circuitry that detects a cardiac event when the cardiac electrical signal crosses a sensing threshold. The cardiac event detection circuitry may include a rectifier, filter and/or amplifier, a sense amplifier, comparator, and/or analog-to-digital converter. Sensing circuitry 87 may output an indication to processing circuitry 85 in response to sensing of a cardiac event (e.g., detected P-waves or R-waves).

In this manner, processing circuitry 85 may receive detected cardiac event signals corresponding to the occurrence of detected R-waves and P-waves in the respective chambers of heart. Indications of detected R-waves and P-waves may be used for detecting ventricular and/or atrial tachyarrhythmia episodes, e.g., ventricular or atrial fibrillation episodes. Some detection channels may be configured to detect cardiac events, such as P-waves or R-waves, and provide indications of the occurrences of such events to processing circuitry 85, e.g., as described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety.

Sensing circuitry 87 may also include a switch module to select which of the available electrodes 97 (or electrode polarities) are used to sense the heart activity. In examples with several electrodes 97, processing circuitry 85 may select the electrodes that function as sense electrodes, i.e., select the sensing configuration, via the switch module within sensing circuitry 87. Sensing circuitry 87 may also pass one or more digitized EGM signals to processing circuitry 85 for analysis, e.g., for use in cardiac rhythm discrimination.

In the example of FIG. 6, IMD 15 includes one or more sensors 92 coupled to sensing circuitry 87. Although illustrated in FIG. 6 as included within IMD 15, one or more of sensors 92 may be external to IMD 15, e.g., coupled to IMD 15 via one or more leads, or configured to wirelessly communicate with IMD 15. In some examples, sensors 92 transduce a signal indicative of a patient parameter, which may be amplified, filtered, or otherwise processed by sensing circuitry 87. In such examples, processing circuitry 85 determines values of patient parameters based on the signals. In some examples, sensors 92 determine the patient parameter values, and communicate them, e.g., via a wired or wireless connection, to processing circuitry 85.

In some examples, sensors 92 include one or more accelerometers 93, e.g., one or more three-axis accelerometers. Signals generated by the one or more accelerometers 93 may be indicative of, as examples, gross body movement (e.g., activity) of the patient, patient posture, heart sounds or other vibrations or movement associated with the beating of the heart, or coughing, rales, or other respiration abnormalities. Accelerometers 93 may produce and transmit signals to processing circuitry 85 for a determination as to the posture of the patient. In various examples, signals from the accelerometers 93 are processed to determine an activity, such as when the patient is taking a step or steps, or for example when the patient is running, used to provide an activity count associated with patient initiated physical activity of the patient. In some examples, sensors 92 may include sensors configured to transduce signals indicative of blood flow, oxygen saturation of blood, or patient temperature, and processing circuitry 85 may determine patient parameters values based on these signals. In various examples, sensors 92 may include one or a combination of sensors 18 as previously described.

In some examples, processing circuitry 85 determines one or more patient parameter values based on pressure signals. Patient parameter values determined based on pressure may include, as examples, systolic or diastolic pressure values, such as pulmonary artery diastolic pressure values. In some examples, a separate device such as sensor circuits 18 (FIGS. 1 and 2), include one or more sensors and sensing circuitry configured to generate a pressure signal, and processing circuitry 85 determines patient parameter values related to blood pressure based on information received from IMD 15.

Therapy delivery circuitry 88, when provided as part of IMD 15, may be configured to generate and deliver electrical therapy to the heart. Therapy delivery circuitry 88 may include one or more pulse generators, capacitors, and/or other components capable of generating and/or storing energy to deliver as pacing therapy, defibrillation therapy, cardioversion therapy, other therapy or a combination of therapies. In some instances, therapy delivery circuitry 88 may include a first set of components configured to provide pacing therapy and a second set of components configured to provide anti-tachyarrhythmia shock therapy. In other instances, therapy delivery circuitry 88 may utilize the same set of components to provide both pacing and anti-tachyarrhythmia shock therapy. In still other instances, therapy delivery circuitry 88 may share some of the pacing and shock therapy components while using other components solely for pacing or shock delivery.

Therapy delivery circuitry 88 may include charging circuitry, one or more charge storage devices, such as one or more capacitors, and switching circuitry that controls when the capacitor(s) are discharged to electrodes 97 and the widths of pulses. Charging of capacitors to a programmed pulse amplitude and discharging of the capacitors for a programmed pulse width may be performed by therapy delivery circuitry 88 according to control signals received from processing circuitry 85, which are provided by processing circuitry 85 according to parameters stored in memory 86. Processing circuitry 85 controls therapy delivery circuitry 88 to deliver the generated therapy to the heart via one or more combinations of electrodes 97, e.g., according to parameters stored in memory 86. Therapy delivery circuitry 88 may include switch circuitry to select which of the available electrodes 97 are used to deliver the therapy, e.g., as controlled by processing circuitry 85.

Communication circuitry 90 includes any suitable hardware, firmware, software or any combination thereof for communicating with another device, such as an external device 11, transceiver 16, or another IMD or sensors, such as sensor circuits 18, as shown in FIG. 1 and FIG. 2. Referring again to FIG. 6, under the control of processing circuitry 85, communication circuitry 90 may receive downlink telemetry from and send uplink telemetry to external device 11 or another device with the aid of an antenna, such as antenna 94, which may be internal and/or external. In some examples, communication circuitry 90 may communicate with a local external device, for example through transceiver 16, and processing circuitry 85 may communicate with a networked computing device via the local external device and a computer network, such as the Medtronic® CareLink® Network developed by Medtronic, plc, of Dublin, Ireland.

As described above, in some examples (i.e., where a single antenna is used) the antenna signal can be switched from the telemetry communication circuitry to the recharge circuit. In other examples the recharge antenna/coil is separate from the communication/telemetry antenna. For example, antenna 94 may be switched between being coupled to communication circuitry 90 and device recharging circuitry 91 by switch 95, wherein switch 95 may be controlled by processing circuitry 85 to determine when antenna 94 is coupled to the communication circuitry 90 and when antenna 94 is to be coupled to the device recharging circuitry 91.

In various examples, processing circuitry 85 is coupled to device recharging circuit 91, and receives information, such as a level of current, that is being induced in antenna 94 or antenna 96 as a result of electrical energy received by the antenna via electromagnetic energy imposed on IMD 15 for the purpose of recharging power source 89. Processing circuitry 85 may provide this and other information, for example charge rate and temperature information associated with the power source 89, in the form of an output signal to communication circuitry 90 for transmission from IMD 15 to one or more external devices, such as transceiver 16. This transmitted information may be used by the external device (s) to control one or more aspects of the recharging process. For example, positioning and/or orientation of a pair of coils located externally to IMD 15 and generating the electromagnetic fields imposed on ID 15 may be controlled using this information transmitted from IMD 15.

The setting of electrical parameters used to energize the coils of a pair of coils generating the electromagnetic fields imposed on IMD 15 for the purpose of recharging the power source 89 may be controlled using this information transmitted from IMD 15. In addition, other information such as temperature and field intensity information transmitted from IMD 15 may be used to control the recharging process, for example by regulating the field strength being generated by the external coils, or for example to shut off the external coils to stop the recharging process.

A clinician or other user may retrieve data from IMD 15 using external device 11 or another local or networked computing device configured to communicate with processing circuitry 85 via communication circuitry 90, for example through a transceiver such as transceiver 16. The clinician may also program parameters of IMD 15 using external device 11 or another local or networked computing devices.

In various examples, processing circuitry 85 is configured to receive signals from sensing circuitry 87, sensors 92, and/or sensor signals provided by sensors external to IMD 15, to process these sensor signals to generate one or more input parameters based either directly on or derived from the sensor signals. The input parameters are associated with current value(s) for one or more physiological parameters associated with a patient, such as patient 12. The physiological parameters associated with the input parameters may include activity counts, respiration rates, breathing rates, movements, postures, and changes in postures associated with a patient. The current values associated with these input parameters can be values measured directly from the input parameters, or derived for these input parameters. For example, a value of a heartrate, measured for example in heartbeats per minute or cardiac cycle length, may be determined as the current value (e.g., the most recent value) for the input parameter associated with the heart rate of the patient measured over some predefined time period. Similarly, a value of a breathing rate, measured for example in breaths per minute or breathing cycle length, may be determined as the current value (e.g., the most recent value) for the input parameter associated with the breathing rate of the patient as measured over some predefined time period.

Similarly, current values can be determined for other input parameters, such as activity count (e.g., based on movement of the patient measured for example in steps taken by the patient per minute), body temperature, and for example a current value for a posture of the patient (e.g., lying down, standing, sitting). A current value of a physiological parameter may be, in some examples, a mean or median of measured values over a period of time. These parameters may be used to monitor the physical condition of a patient, and/or to determine the efficacy of a therapy being applied to the patient, and/or the need to apply a new or different therapy, such as a new or different electrical stimulation therapy, to the patient based on analysis if the sensed parameters and/or instructions received by IMD 15 from one or more external devices.

Figure 7:
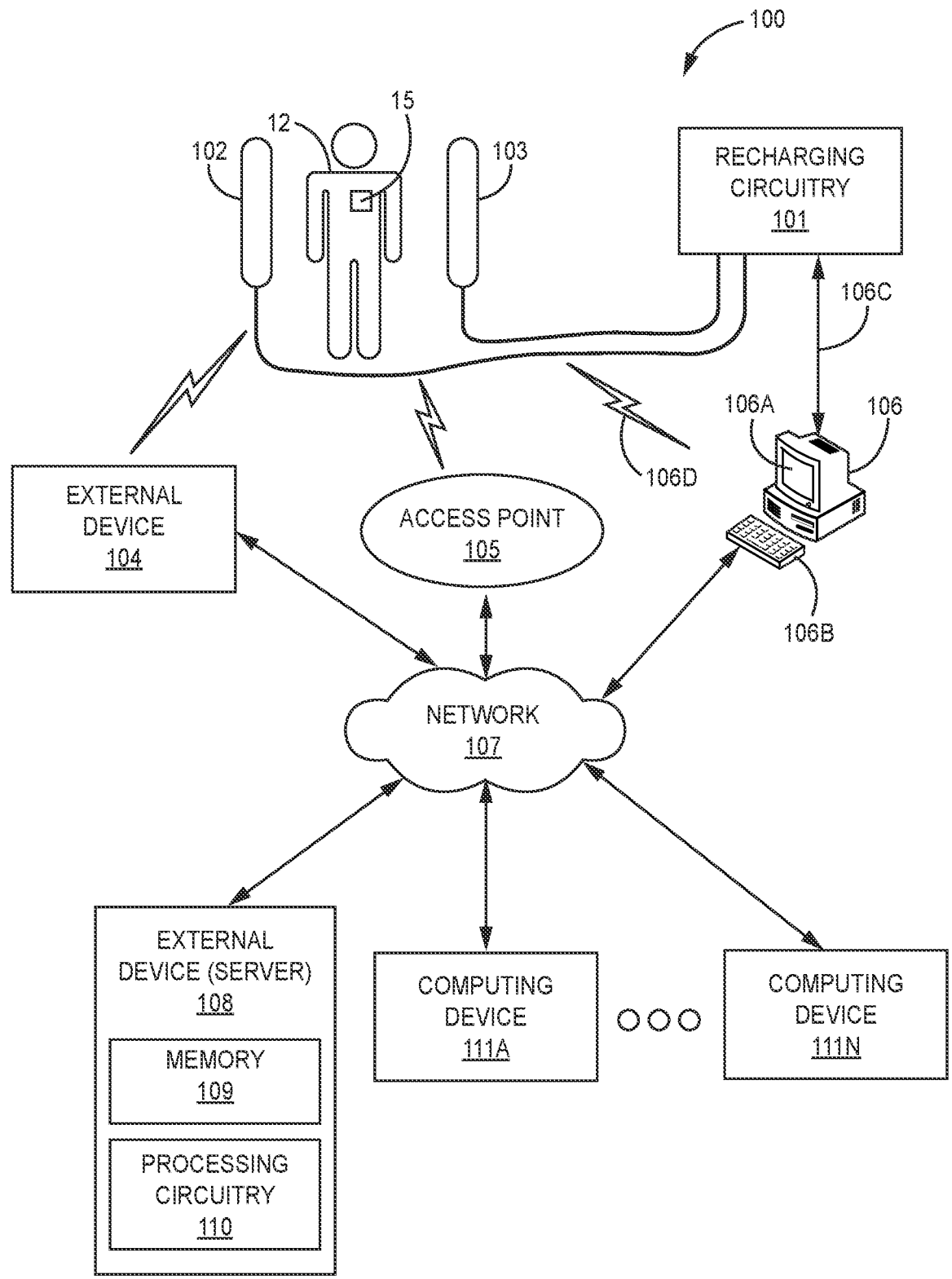
FIG. 7 is a functional block diagram illustrating an example inductive recharging system according to various examples described in this disclosure.

FIG. 7 is a functional block diagram illustrating an example inductive recharging system 100 according to various examples described in this disclosure. System 100 includes recharging circuitry 101 electrically coupled to a pair of coils comprising first coil 102 and second coil 103, located externally to a patient 12, according to various examples described in this disclosure. In some examples, coils 102, 103 are physically arranged as further described below as a pair of coils would be physically arranged in a form similar to a Helmholtz coil. When energized, coils 102 and 103 may be configured to provide a time-varying set of opposing electromagnetic fields that may be imposed on an implanted medical device, such as IMD 15 illustratively represented as being implanted in patient 12, for the purpose of recharging a power source within IMD 15. Recharging circuitry 101 may be coupled to a computing device 106 that includes a display 106A and one or more input devices 106B, such as a keyboard and/or a computer mouse, that allow a user to interact with recharging circuitry 101 through computing device 106. Computing device 106 may be communicatively linked to recharging circuitry 101 by a wired connection 106C, and/or by a wireless connection 106D.

In various examples, computing device 106 is configured to allow a user, such as a physician or a technician (neither shown in FIG. 7), to operate and control recharging circuitry 101 in a manner that apportions the relative intensities of the electromagnetic fields generated by coils 102, 103 in such a way as to steer the direction of the peak magnetic field intensity, thus maximizing the power transfer to a single recharging coil (e.g., a receive antenna) located within IMD 15 that is positioned in the electromagnetic field generated by coils 102, 103. Further, feedback received from IMD 15, for example received by computing device 106, may be used to control and adjust various aspects of recharging circuitry 101, including physically adjusting the positioning and the relative strength of the opposing magnetic fields being generated by each of the electrical coils 102, 103 based on the feedback provided by IMD 15.

For example, the set of electrical coils 102, 103 may be arranged so that the position of the coils can be moved, for example up and down, left or right, and/or tilted or rotated around one or more axes running between coils 102, 103, in order to position the receive antenna of IMP 15 within an estimated optimal charging envelope formed by the electromagnetic fields being generated through the energization of coils 102 and 103. When the receive antenna is positioned within the estimated optimal recharging envelope, a positional angle θ (theta) of rotation of the third coil around a longitudinal axis extending between the pair of recharging coils irrelevant with respect to a coupling efficiency of the level of the electrical current being induced in the third coil by the resultant magnetic field. Further, the individual control over the energization of each of first coil 102 and second coil 103, as provided by recharging circuitry 101, may be used to steer the direction of the resultant magnetic field imposed on the receive coil of the recharging circuitry located within IMD 15, and angle of orientation φ (phi) between the normal axis of the third coil and the longitudinal axis, thus increasing the level of inductive coupling and the power transfer provided to the receive coil by the recharging circuitry.

In some instances, the energization of the coils 102, 103 may be reconfigured so that instead of generating opposing magnetic fields in the volumetric space between the coil, the coils are energized to generate a uniform magnetic field having a same direction throughout the space between the coils and that parallels the direction of a longitudinal axis running between the center points of the coils, as further described below. A determination as to whether to energize coils 102 and 103 to generate opposing magnetic fields or to generate a uniform magnetic field may be made based on the relative orientations of the receive antenna in the device being recharged and the orientation of coils 102 and 103. The decision to use opposing magnetic fields versus a uniform magnetic field having a same direction throughout the space between coils 102 and 103 may be based on the measured level of current being induced into the receive coil by coils 102 and 103 during a recharging procedure performed on the deice to be recharged.

Feedback from IMD 15 in some examples comprises a value for the level of current that is being induced in the receive coil of IMD 15 through the inductive coupling of the energy being provided by coils 102 and 103. Other information provided by IMD 15, such as temperature, rate of charge, and percentage of charge information generated by IMD 15, may be transmitted from IMD 15 to computing device 106 and/or other external devices, and used by recharging circuitry 101 to control the energization of coils 102 and 103, and/or to determine when to terminate the recharging process being performed by recharging circuitry 101 on IMD 15.

System 100 further includes external computing devices, such as a server 108 and one or more other computing devices 111A-111N, that may be communicatively coupled to IMD 15, computing device 106, and/or external device 104 via a network 107. In this example, IMD 15 may use its communication circuitry, at different times and/or in different locations or settings, to communicate with external device 104 via a first wireless connection, and/or to communicate with an access point 105 via a second wireless connection. In the example of FIG. 7, computing device 106, access point 105, external device 104, server 108, and computing devices 111A-111N are interconnected, and able to communicate with each other, at least through network 107.

Access point 105 may comprise a device that connects to network 107 via any of a variety of connections, such as telephone dial-up, digital subscriber line (DSL), or cable modem connections. In other examples, access point 105 may be coupled to network 107 through different forms of connections, including wired or wireless connections. In some examples, access point 105 may be co-located with the patient. Access point 105 may interrogate IMD 15, e.g., periodically or in response to a command from the patient or from network 107, to retrieve physiological measurements and/or other operational or patient data from IMD 15. Access point 105 may provide the retrieved data to server 108 via network 107. In various examples, access point 105 may be any example of transceiver 16 described above. In various examples, access point 105 may be any example of external device 11 described above. In some cases, server 108 may be configured to provide a secure storage site for data that has been collected from IMD 15, from recharging circuitry 101, and/or from external device 104. In some cases, server 108 may assemble data in web pages or other documents for viewing by trained professionals, such as clinicians, via computing devices 111A-111N. The illustrated system 100 of FIG. 7 may be implemented, in some aspects, with general network technology and functionality similar to that provided by the Medtronic® CareLink® Network developed by Medtronic plc, of Dublin, Ireland.

In some examples, one or more of computing device 106, access point 105, server 108, or computing devices 111A-111N may be configured to perform, e.g., may include processing circuitry configured to perform, some or all of the techniques described herein, e.g., with respect to processing circuitry of IMD 15 and external device 104, relating to the recharging of power source located within IMD 15. In the example of system 100 as shown in FIG. 7, server 108 includes a memory 109, which may be configured to store physiological and other data received from IMD 15 and/or external device 104, and processing circuitry 110, which may be configured to provide some or all of the functionality ascribed to processing circuitry of IMD 15 as described herein. For example, processing circuitry 110 may provide programming and/or parameters that are used by recharging circuitry 101 that may be used in the process of providing inductive recharging to a power source located within IMD 15. Configurations for and operational features of coils 102 and 103, and recharging circuitry 101, are further described with respect to FIGS. 8A-8C, FIGS. 9A-9B, FIGS. 10A-10B, and FIGS. 11-16 of this disclosure.

Figure 8A:
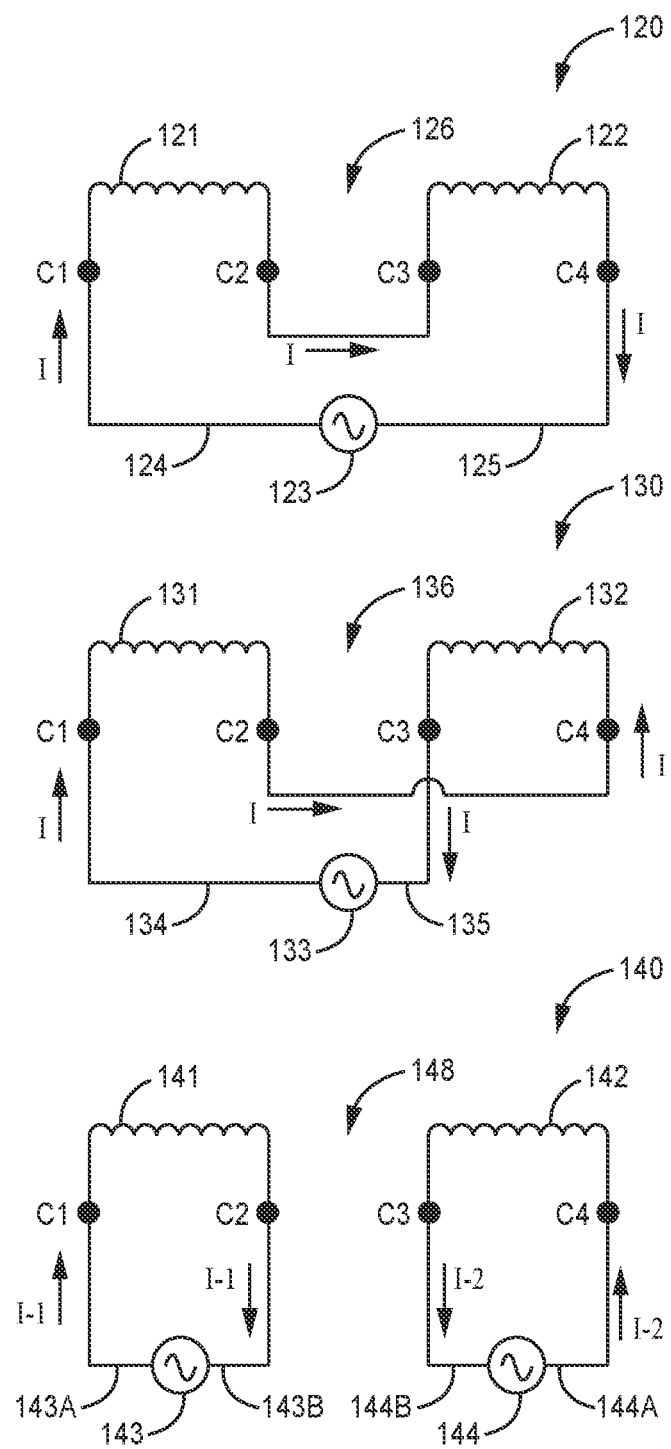
FIG. 8A illustrates example wiring diagrams of pairs of electrical coils according to various examples described in this disclosure.

FIG. 8A illustrates examples of wiring diagrams 120, 130, and 140 for pairs of electrical coils according to various examples as described in this disclosure. As shown in wiring diagram 120, an electrical power source 123 is configured to provide an electrical current that is electrically coupled through electrical conductors, such as wires formed from an electrically conductive material such as a conductive metal, to a first electrical coil 121 and a second electrical coil 122. As illustrated in diagram 120, the first electrical coil 121 has a first connection C1 coupled to a first terminal 124 of the electrical power source 123, and a second connection C2 coupled to a first connection C3 of the second electrical coil 122. The second electrical coil includes a second connection C4 coupled to a second terminal 125 of the electrical power source 123. When coupled as shown in wiring diagram 120, the first electrical coil 121 and the second electrical coil 122 are electrically coupled in series, so that at any given time, an electrical current provided by the electrical power source 123, for example at terminal 124, flows from terminal 124 to connection C1 of the first electrical coil 121, out of the first electrical coil 121 at connection C2, and into the second electrical coil 122 at connection C3, exiting the second electrical coil 122 at connection C4 to return to the electrical power source 123 through second terminal 125. This current flow is illustratively represented by the arrows and associated letter "I" as shown in wiring diagram 120.

It would be understood one of ordinary skill in the art that the current flow illustrated in wiring diagram 120 could also flow in the direction opposite that shown in wiring diagram 120, e.g., from electrical power source 123 to second coil 122, and then to the first electrical coil 121 before returning to the electrical power source 123. In various examples, the amplitude, direction (e.g., polarity), and/or the magnitude (e.g., variations in frequency and/or duty cycle) of the current flow provided by electrical power source 123 to the first electrical coil 121 and the second electrical coil 122 may also be varied in a time dependent matter, for example in the form of an alternating current having a sinusoidal waveform or some other waveform that varies the amplitude, polarity, and/or magnitude of the current in some manner over time.

If the first electrical coil 121 and the second electoral coil 122 in wiring diagram 120 are physically constructed and placed relative to one another in a particular arrangement, such as an arrangement that would approximate a Helmholtz coil, a relatively uniform magnetic field may be induced in area 126 between the coils. When electrical power source 123 is providing a varying current to the first electrical coil 121 and the second electrical coil 122 using the wiring arrangement illustrated by wiring diagram 120, the magnetic field generated in the area 126 between the coils may be in a same direction (parallel direction) relative to a longitudinal axis common to both coils. This magnetic field generated in the area 126 between the coils will be substantially uniform throughout most to the area 126 that lies between the coils, and may be used for example to induce an electrical current in a third coil (not shown in wiring diagram 120) located in the area 126 between the first electrical coil 121 and the second electrical coil 122.

The third electrical coil in some examples may be an antenna and/or recharge coil of an implanted medical device, and the electrical current induced in the third electrical coil may be used to charge a rechargeable power source, such as a battery or a capacitive device (not shown in wiring diagram 120), which is coupled to the third coil, of the implanted medical device (not shown in wiring diagram 120). In examples of the third coil configured to have only a single axis of orientation, such as a flat-planar type antenna, the uniform magnetic field provided in area 126 may or may not be aligned with the axis of orientation of the third coil, and thus may provide no inductive coupling, or a poor or an inefficient level of inductive coupling between the coils 121, 122 and the third coil.

Another wiring arrangement for an electrical power source and a pair of electrical coils is illustrated in wiring diagram 130 of FIG. 8A. As shown in wiring diagram 130, an electrical power source 133 includes a first terminal 134 coupled to a first connection C1 of a first electrical coil 131. The first electrical coil 131 includes a second connection C2 coupled to a second connection C4 of a second electrical coil 132. A first connection C3 of the second electrical coil 132 is coupled to the second terminal 135 of the electrical power source 133.

When coupled as shown in wiring diagram 130, the first electrical coil 131 and the second electrical coil 132 are electrically coupled in series, so that at any given time, an electrical current provided by the electrical power source 133, for example at terminal 134, flows from first terminal 134 to connection C1 of the first electrical coil 121, out of the first electrical coil 131 at connection C2 and into the second electrical coil 132 at connection C4, and exiting the second electrical coil 132 at connection C3 to return to the electrical power source 133 through second terminal 135. This current flow is illustratively represented by the arrows and associated letter "I" as shown in wiring diagram 130. It would be understood one of ordinary skill in the art that the current flow illustrated in wiring diagram 130 could also flow in the direction opposite that shown in wiring diagram 130, e.g., from electrical power source 133 to second coil 132, and then to the first electrical coil 131 before returning to the electrical power source 133. In various examples, the amplitude, direction, and/or the magnitude of the current flow provided by electrical power source 133 to the first electrical coil 131 and the second electrical coil 132 may also be varied in a time dependent matter, for example in the form of an alternating current having a sinusoidal waveform or some other waveform that varies the amplitude, polarity, and/or magnitude of the current in some manner over time.

If the first electrical coil 131 and the second electrical coil 132 are physically constructed and placed relative to one another in a particular arrangement, such as an arrangement that would approximate a Helmholtz coil, a magnetic field may be induced in an area 136 between the coils. When electrical power source 133 is providing a current to the first electrical coil 131 and the second electrical coil 132 using the wiring arrangement illustrated by wiring diagram 130, the magnetic fields generated in the area 136 between the coils may be used to induce an electrical current in a third electrical coil (not shown in wiring diagram 130), placed in the area 136 between the first electrical coil 131 and the second electrical coil 132 to allow recharging of a rechargeable power source or a capacitive device (not shown in wiring diagram 130), coupled to the third electrical coil in a manner similar to that described above with respect to wiring diagram 120.

In contrast to the arrangement as described above with respect to wiring diagram 120, the magnetic fields generated by the first electrical coil 131 and the second electrical coil 132, respectively, when a current is being provided to these coils by the electrical power source 133, will not be in a same direction within the area 136 between the two coils and relative to a longitudinal axis common to both coils. Because of the opposed wiring arrangement of the first electrical coil 131 relative to the wiring arrangement of the second electrical coil 132, the first electrical coil 131 may generate a magnetic field having a direction that is opposite (e.g., opposed to) the magnetic field generated by the second electrical coil 132, while having a magnetic field intensity that is approximately the same as the magnetic field intensity generated by the second electrical coil 132. As described in further detail below, the resultant magnetic field generated by the opposing magnetic fields of the first electrical coil 131 and the second electrical coil 132 may provide areas of resultant magnetic fields located between the first electrical coil 131 and the second electrical coil 132 having an orientation that is perpendicular or substantially perpendicular to the longitudinal axis common to and extending between both coils.

Within these areas of the resultant magnetic field that are generally perpendicular to the longitudinal axis common to both the first and second electrical coils in wiring diagram 130, the positional angle θ (theta) of rotation of a third electrical coil placed within these areas relative to a longitudinal axis extending between the coils 131 and 132 becomes irrelevant with respect to the coupling efficiency for inducing an electrical current into the third electrical coil. Thus, for recharging purposes, the positional angle θ (theta) of rotation of the third electrical coil relative to the longitudinal axis extending between the recharging coils 131 and 132 is removed as a factor with respect to the coupling efficiency achieved between the resultant magnetic field provided by the first and second electrical coils 131, 132 and the third coil. Rendering the positional angle θ (theta) of rotation of the third coil irrelevant reduces the number of positional angles of rotational relative to the longitudinal axis between the coils that need to be taken into account when attempting to position and orient the third electrical coil within the electromagnetic fields that are generated are between the first electrical coil 131 and the second electrical coil 132 for the purpose of providing an efficient level of coupling between the magnetic fields generate by the coils 131, 132 and the third coil.

For example, by positioning the third coil in portions of the area 136 where the resultant magnetic field is perpendicular or substantially perpendicular to the longitudinal axis common to and extending between coils 131, 132, the position of the third coil may be rotated around the longitudinal axis extending between the coils 131, 132 to any angle θ (theta) around the longitudinal axis while maintaining a same angle of orientation φ (phi) between the normal axis of the third coil and the longitudinal axis, and same level of inductive coupling may be achieved regardless of the angle θ (theta) of rotation. The elimination of at the positional angle θ (theta) of rotational orientation of the third coil around the longitudinal axis as described above may allow for a simpler system, such as a recharging system using only a single pair of electrical coils 131, 132, to be utilized to recharge a device coupled to the third antenna while achieving a high or a maximum level of inductive coupling between the coils 131, 132 and the third antenna. The high or maximum level of inductive coupling may be achieved even when the third coil may be part of a deeply implanted medical device, and/or when the third coil for example has only a single axis (e.g., a normal axis) of orientation for inductive coupling with magnetic field(s) imposed on the third coil.

A system that includes a pair of coils such as coils 131, 132 and wired as illustrated in wiring diagram 130, may be used to induce a current into a third coil that is positioned within certain portions of area 136 between the coils that includes a perpendicular or substantially perpendicular resultant magnetic field relative to the longitudinal axis that extends between the coils. When the third coil is positioned within the areas that include the perpendicular or substantially perpendicular resultant magnetic field, the positional angle θ (theta) of rotational orientation of the third coil relative to the longitudinal axis extending between the coils 131, 132 may be rendered irrelevant by the opposing magnetic fields generating the perpendicular resultant magnetic fields. Addition alignment(s) may be made between the pair of coils and the third coil for example by moving/tilting the position of the pair of coils relative to the third coil, and/or moving/tilting the third coil for example by repositioning the patient relative to the pair of coils. These additional alignments may be performed, and in some examples automatically controlled, based on feedback provided by circuitry coupled to the third coil that indicates the level of induced current and/or the level coupling efficiency that is being achieved at the third coil.

The additional alignment described above may allow for better alignment of the relevant axis or axes of orientation of the third coil with the resultant magnetic field being generated by coils 131, 132, to achieve a high level or even a maximum level of inductive coupling between the pair of coils energized to generate the resultant magnetic field and the third coil. Use of a wiring technique as shown in wiring diagram 130 may simplify a recharging system used to recharge an implanted medical device for example by providing a system that requires only a single pair of recharging coils to generate the resultant magnetic field used to recharge the power source of an implanted IMD, while allowing a high level or a maximum level of coupling efficiency, even when the receive antenna (third coil) of the IMD is a uni-directional or planar type coil.

Another wiring arrangement for an electrical power source and a pair of electrical coils is illustrated in wiring diagram 140 of FIG. 8A. As shown in wiring diagram 140, a first electrical power source 143 includes a first terminal 143A coupled to a first connection C1 of the first electrical coil 141. The first electrical coil 141 includes a second connection C2 coupled to a second terminal 143B of electrical power source 143. A second electrical power source 144 includes a first terminal 144B coupled to a first connection C3 of the second electrical coil 142. The second electrical coil 142 includes a second connection C4 coupled to a second terminal 144A of electrical power source 144. When coupled as shown in wiring diagram 140, the first electrical coil 141 and the second electrical coil 142 are electrically isolated from each other with respect to the current being provided to each coil, so that at any given time, an electrical current provided by the electrical power source 143 to the first electrical coil 141 may be illustratively represented by "I-1," and an electrical current provided by electrical power source 144 to the second electrical coil 142 may be illustratively represented by "I-2" in wiring diagram 140.

Because the first power source 143 and the first electrical coil 141 are electrically isolated from the second power source 144 and the second electrical coil 142, the amount of current flowing through the first electrical coil 141, illustratively shown as "I-1" in wiring diagram 140, may be different in amplitude, polarity, and/or magnitude at any given time relative to the current flowing through the second electrical coil 142, which is illustratively shown as "I-2" in wiring diagram 140. While shown in wiring diagram 140 as separated power sources, it would be understood by one of ordinary skill in the art that power source 143 and power source 144 may be separately controllable outputs provided by a single power source or power supply, and need not necessarily be provided by individual or separate power supply devices.

It would be understood one of ordinary skill in the art that these current flows illustrated in wiring diagram 140 could also flow in the direction opposite that shown in wiring diagram 140. For example, current flow "I-1" flowing through first electrical coil 141 may flow from electrical power source 143 to connector C2 of the first electrical coil 141, and return to the first power source 143 through connection C1, and current flow "I-2" flowing through second electrical coil 142 may flow from electrical power source 144 to connector C3 of second electrical coil 142 and return to the second power source 144 through connector C4 of the second coil 142. In various examples, the direction, polarity, and/or the magnitude of the current flow provided by electrical power source 143 to the first electrical coil 141 and the current flow provided by second electrical power source 144 to the second electrical coil 142 may be varied in a time dependent matter, for example in the form of an alternating current having a sinusoidal waveform, or some as other waveform that vary the amplitude, polarity, and/or magnitude of these currents in some manner over time.

If the first electrical coil 141 and the second electrical coil 142 are physically constructed and placed relative to one another in a particular arrangement, such as an arrangement that would approximate a Helmholtz coil, a resultant magnetic field may be induced in the area 148 between the coils. When electrical power source 143 is providing a varying current to the first electrical coil 141 and the second power source 144 is providing a varying current to the second electrical coil 142 using the wiring arrangement illustrated by wiring diagram 140, the resultant magnetic field generated in the area 148 between the coils may be used to induce an electrical current in a third electrical coil (not shown in wiring diagram 140), placed in the area 148 between the first electrical coil 141 and the second electrical coil 142. The induced current may allow recharging of a rechargeable power source or a capacitive device (not shown in wiring diagram 140), coupled to the third electrical coil in a manner similar to that described above with respect to wiring diagram 120.

In contrast to the arrangement as described above with respect to wiring diagram 120, the magnetic fields generated by the first electronic coil 141 and the second electrical coil 142 when currents are being provided to these coils by the electrical power sources 143, 144, respectively, may be opposing one another, e.g., not be in a same direction within the area 148 between the two coils and relative to a longitudinal axis common to and extending between both coil. Because of the opposed wiring arrangement and electrical isolation of the first electrical coil 141 relative to the wiring arrangement of the second electrical coil 142, the first electrical coil 141 may generate a magnetic field having a direction that is opposite (e.g., opposed to) the magnetic field generated the second electrical coil 142.

As described in further detail below, the resultant magnetic field generated by the opposing magnetic fields of the first electrical coil 141 and the second electrical coil 142 may provide areas of resultant magnetic field located between the first electrical coil 141 and the second electrical coil 142 that are perpendicular to the longitudinal axis common to and extending between both coils within some portions of the area 148 located between the coils. Within these areas of the resultant magnetic field, the positional angle θ (theta) of rotation of a third electrical coil relative to the longitudinal axis extending between to the two coils 141 and 142 becomes irrelevant with respect to the coupling efficiency for inducing an electrical current into the third electrical coil. Thus, for recharging purposes, the positional angle θ (theta) of rotation of the third electrical coil relative to the longitudinal axis extending between the recharging coils is removed as a factor with respect to the coupling efficiency between the magnetic fields providing the first electrical coil 141 and the second electrical coil 142. This feature reduces the number of orientations that need to be taken into account when attempting to orient the third electrical coil within the electromagnetic fields that are generated are between the first electrical coil 141 and the second electrical coil 142 for the purpose of providing an efficient level coupling between the first and second electrical coils and the third coil that may be placed within in the area 148.

Further, because coil 141 is controlled and powered by a separate power supply (e.g., first power source 143) relative to the second electrical coil 142 (e.g., powered by second power source 144), the electromagnetic fields generated in the area 148 between first electrical coil 141 and second electrical coil 142 may be further controlled so that the opposing magnetic fields within area 148 may be "bent" or "steered" in a direction such that that the resultant magnetic field in portions of area 148 have angles of direction that are not perpendicular to the longitudinal axis extending between the first and second electrical coils. For example, by providing a larger current, or a current having a higher amplitude to one of coils 141, 142 compared to the level of current provided to the other coil of coils 141, 142, the resultant magnetic field within portions of area 148 may be further steered, e.g., bent in a particular direction to produce a resultant magnetic field having an angle of direction that is not perpendicular to the longitudinal axis common to both coils. The bending or steering may allow the resultant magnetic field to be generated at an angle of direction that is more aligned with a particular axis of orientation of a third coil that has been placed within area 148 for the purpose of recharging a power source of an implanted medical device (not shown in wiring diagram 140), that is coupled to the third coil.

In some examples, the steering of the opposing magnetic fields generated by the first electrical coil 141 and the second electrical coil 142 within portions of area 148 may be adjusted and controlled to create an angle corresponding to a direction for the resultant magnetic field that aligns with an angle of orientation φ (phi) between the normal axis of the third coil and the longitudinal axis extending between coils 141 and 142. By doing so, the angle of direction of the resultant magnetic field provided in one or more portions of area 148 between the first and second coils 141, 142 may be arranged so that the direction of the resultant magnetic field generated between the first and second electrical coils 141, 142 better aligns with the axis of orientation of normal axis of the third coil placed within area 148.

Using the arrangements of a pair of coils electrically coupled for example as illustrated by wiring diagrams 130 or by wiring diagram 140, and energizing the pair of coils to generate opposing magnetic fields within areas between the pair of coils, a resultant magnetic field may be generated within portions of the area between the pair of coils that may be used to inductively couple electrical power to a third coil placed in the area between the pair of coils, wherein the resultant magnetic field renders the positional angle θ (theta) of rotational orientation of a third electrical coil relative to the longitudinal axis extending between the two coils irrelevant with respect to the level of inductive coupling efficiency that may be achieved between the two recharging coils and the third coil.

The areas between the coils used to generate the resultant magnetic fields that provide these features may be referred to as the "estimated optimal recharging envelope," or simply the "recharging envelope," as further described below. In addition, by providing separately controllable power sources, or a single power source with separately controllable power outputs coupled individually to the coils 141, 142, the resultant magnetic field generated in portion of the area 148 between the coils may be bent or steered to align with the resultant magnetic field with an angle of orientation φ (phi) between the normal axis of the third coil and the longitudinal axis, the third coil being coupled to a power source of an IMD that is to be recharged via the energy transferred to the third coil from the resultant magnetic field.

Use of a wiring technique as shown in wiring diagrams 130 and 140 may simplify a recharging system used to recharge an implanted medical device for example by providing a system that requires only a single pair of recharging coils used to generate the resultant magnetic field used recharge the power source of an implanted IMD, while allowing a high level or a maximum level of coupling efficiency, even when the receive antenna (third coil) of the IMD is a uni-direction or planar type coil. The added capability to bend or steer the resultant magnetic field gendered between the recharging coils 141, 142 for example as shown in wiring diagram 140 may further simply the system by reducing or eliminating the need to reposition, e.g., rotate or tilt, the recharging coils in order to align the resultant magnetic field with the normal axis of orientation of the receive antenna (third coil) used to provide the induced electrical current for recharging the power source of the implanted IMD.

Figure 8B:
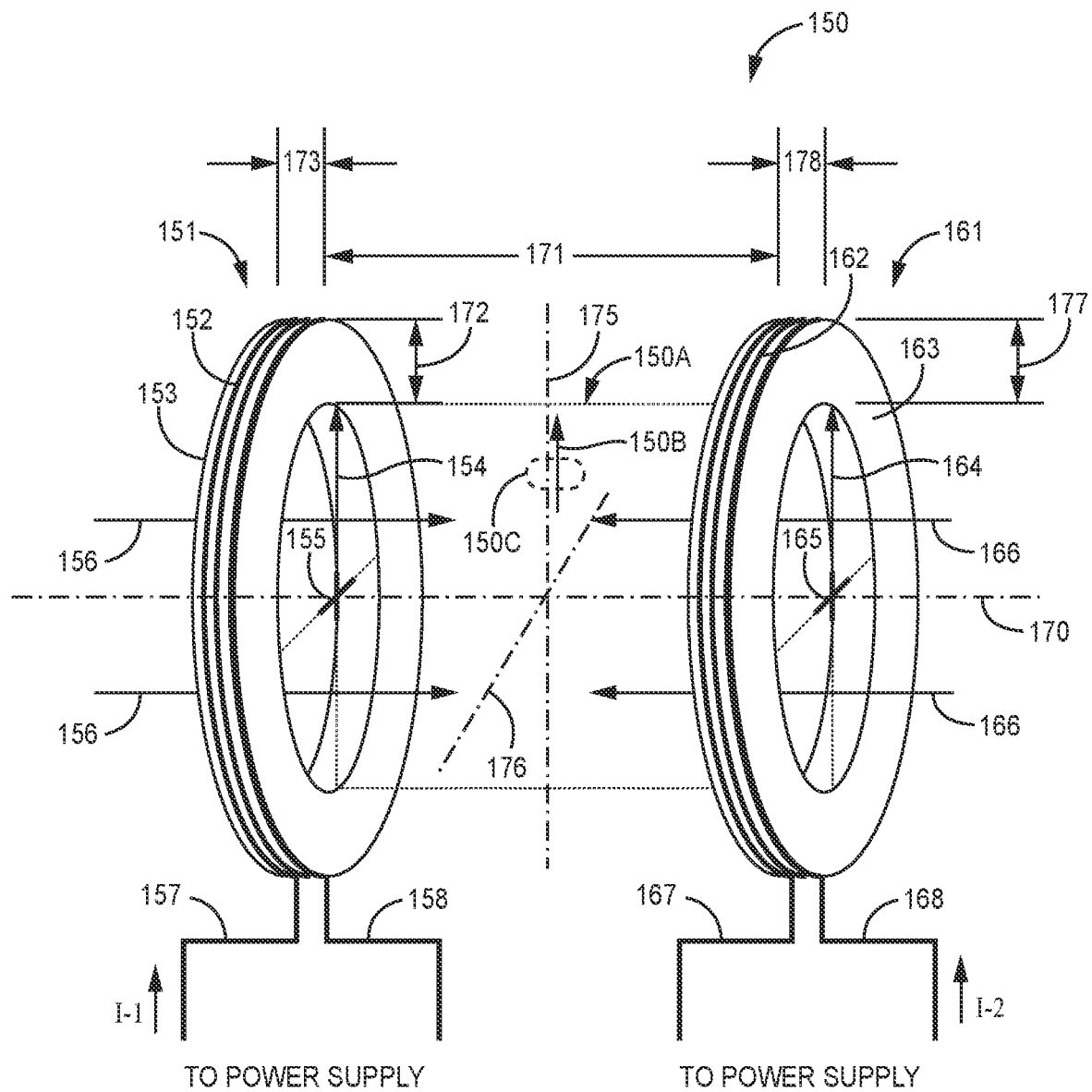
FIG. 8B illustrates a portion of a recharging system comprising an example pair of electrical coils according to various examples described in this disclosure.

FIG. 8B illustrates a portion of a recharging system 150 comprising an example pair of electrical coils 151 and 161 in accordance with example implementations and techniques described in this disclosure. In some examples of system 150, first electrical coil 151 and second electrical coil 161 are physically configured and positioned in a same or similar manner used to form a Helmholtz coil, although examples of coils 151 and 161 are not limited to being physically configured to specifically form a Helmholtz coil arrangement. For example, as shown in FIG. 8B, coils 151 and 161 are illustrated as symmetrical coils, each having a circular shaped winding that is wound around center points 155 and 165, respectively, and each winding spaced apart from one another at a distance 171 along a longitudinal axis 170 common to both coils. Distance 171 in some examples is equal to a radial dimension of each coil, such as radius 154 of coil 151 and radius 164 of coil 161. Distance 171 may also be referred to as a separation distance between coils 151 and 161. Such physical arrangement for a pair of electrical coils is commonly associated with a Helmholtz coil.

The example of coils 151, 161 as illustrated and described with respect to FIG. 8B is intended to be a non-limiting example of an arrangement of a pair of coils that may comprise a portion of a recharging system according to the devices, systems and techniques described in this disclosure. Variations of the examples of a pair of coils that may be utilized as part of a recharging system configured to perform the techniques described in this disclosure are not limited to a Helmholtz coil, or to the example as illustrated in FIG. 8B. For example, the shape of coils 151, 161 is not limited to circular shaped windings, and may be other shapes such as square, rectangular, or elliptical shaped windings, as well as coils that are "bent" over a saddle curve, or otherwise non-flat curve with a plane that is perpendicular to and intersects the axis 170.

In addition, the spacing between the coils is not limited any particular dimensional value that need be a same dimension or a dimension that is proportional in a particular manner to the spacing dimension. For example, a distance between the coils measured along a line intersecting the windings of both coils and that is parallel to the axis 170 may have a different value at different positions around the circumference or the perimeters of the coils. In these instances, the cross-sectional dimensions of the recharging envelope formed between the coils may vary as the recharging envelope extends around the axis 170. For example, some portion of the recharging envelope may be "wider" e.g., have a larger dimensional value for the axis) at some portions of the envelope comparted to other portions of the envelope. In addition, the coils 151, 161 do not necessary have to be symmetrical relative to the size and/or shape dimensions of one coil relative to the other coil. Other possible variations related to the construction, dimensions, and relative physical positioning and/or configuration of the coils forming a pair of coils for use in a recharging system are described and illustrated throughout this disclosure, for example with respect to FIGS. 7, 8A, 8C, 9, 10A, 10B, and 11-13.

As illustrated in FIG. 8B, the first electrical coil 151 includes a winding 152 comprising a length of an electrical conductor, which may be wound onto a winding support structure 153. The winding 152 may be formed generally in the shape of a toroid. Support structure 153 supports the winding 152 so that each of the windings of the electrical conductor, or conductors such as multi-strand conductors (e.g., Litz wire), forming winding 152 are formed in a substantially circular-shaped configuration located around and encircling a center point 155 of the support structure 153, wherein the winding 152 is located at a minimum distance away from and encircling the center point 155 at a radius 154, or within a first distance and a second distance (e.g., a range of distances determining a thickness 172 of the winding 152 relative center point 155) substantially within a small variation of the distance around the radius 154.

In some examples, any section of the winding 152 when cut in cross-section by a plane that contains longitudinal axis 170 may include a shape, such as a square, rectangular, circular or elliptical shape, that extends along the winding in a direction that encircles the center point 155 of the first electrical coil 151. Each individual circular winding of the electrical conductor included in winding 152 of the first electrical coil 151 may lie in one or more planes that are perpendicular to longitudinal axis 170, forming a width 173 for winding 151, and having each winding lying at least at a minimum distance 171 from the windings of the second electrical coil 161 in a direction corresponding to the direction of longitudinal axis 170. As shown in FIG. 8B, longitudinal axis 170 comprises a line intersecting both the center point 155 of the first electrical coil 151 and a center point 165 of the second electrical coil 161.

As shown in FIG. 8B, the second electrical coil 161 includes a winding 162 comprising a length of an electrical conductor, which may be wound onto a winding support structure 163. The winding 162 may be formed generally in the shape of a toroid. Support structure 163 supports the winding 162 so that each of the windings of the electrical conductor are formed in a substantially circular-shaped configuration located around a center point 165 of the support structure 163, wherein the winding 162 is located at a minimum distance away from and encircling the center point 165 at a radius 164, or within a first distance and a second distance (e.g., a range of distances determining a thickness 177 of the winding 162 relative to center point 165), substantially within a small variation of the distance around the radius 164. In some examples, any section of the winding 162 when cut in cross-section by a plane that contains longitudinal axis 170 may include a shape, such as a square, rectangular, circular or elliptical shape, that extends along the winding in a direction that encircles the center point 165 of the second electrical coil 161. Each individual circular winding of the electrical conductor (or multi-strand conductor) included in winding 162 of the second electrical coil 161 may lie in one or more planes that are perpendicular to longitudinal axis 170, forming a width 178 for winding 161, and each winding lying at least at a minimum distance 171 from the windings of the first electrical coil 151 in a direction corresponding to the direction of longitudinal axis 170.

Examples of the shape of each of the windings 152 and 162 are not limited to any particular shape surrounding center points 155, 165, respectively. For example, instead of being circular in shape, the shapes of windings 152 and 162 may in some examples be a square or rectangular shape that surrounds the respective center point of the winding. In general, the windings 151 and 161 are separated from one another by a distance 171, wherein in some examples a value for distance 171 is equal to the value as each of radii 154 and 164. The winding 152 of the first electrical coil 151 may be spaced away by a distance from an origin formed at the intersection of a vertical axis 175 and a horizontal axis 176 that are each perpendicular to the longitudinal axis 170 and perpendicular to each other, The winding 162 of the second electrical coil 162 may be spaced away by a distance from the same origin where the longitudinal axis 170, the vertical axis 175, and the horizontal axis 176 intersect, wherein a value for distance between the origin and coil 151 is equal to a value for the distance between the origin and coil 161. In various examples, the shape and dimensions of the first electrical coil 151 are the same as and are symmetrical to the shape and the dimensions of the second electrical coil 161. Additional examples and details regarding the windings 152 and 162 that may be used to form the first and second electrical coils 151, 161, respectively, are illustrated and described with respect to FIG. 8C.

As shown in FIG. 8B, the first electrical coil 151 may be coupled to an electrical power supply (not shown in FIG. 8B, but for example power source 133 or power source 143 as shown in FIG. 8A). As shown in FIG. 8B, the electrical power supply may be coupled to a terminal 157 that is electrically coupled to a first end of winding 152, and to a terminal 158 that is electrically coupled to a second end of winding 152 opposite the first end, and configured to deliver a current flow "I-1" to the conductive winding 152 of the first electrical coil 151. The second electrical coil 161 may be coupled to an electrical power supply (not shown in FIG. 8B, but for example power source 133 or power source 144 as shown in FIG. 8A), the electrical power supply configured deliver a current flow I-2 to the conductive winding 162 of the second electrical coil 161. In some examples, a same power supply is coupled to the first electrical coil 151 and the second electrical coil 161, and in these examples, the level of current provided to the first electrical coil 151 as current "I-1" would be the same level of current provided to the second electrical coil 161 as current "I-2."

In other examples, separate power supplies, or at least separately controllable outputs from a common power supply, are coupled to provide the current "I-1" to the first electrical coil 151 and the current "I-2" to the second electrical coil 161. In examples using separate power supplies or separately controllable outputs from a same power supply coupled to the first and second electrical coils, the current "I-1" supplied to the first electrical coil 151 may have a different level, e.g., a different amplitude or a difference with respect to some other electrical parameter, such as duty cycle or magnitude, relative to the current supplied to the second electrical coil 161 as current "I-2."

Regardless of whether the first and second electrical coils are provided current by a same or different power supplies, when energized, the first electrical coil 151 may be configured to generate a first magnetic field having a direction generally indicated by arrows 156 in the area encircled by the first electrical coil and surrounding center point 155, the first magnetic field extending along longitudinal axis 170 in a direction toward the second electrical coil 161. Further, when energized, the second electrical coil 161 may be configured to generate a second magnetic field having a direction generally indicated by arrows 166 in the area encircled by the second electrical coil and surrounding center point 165, the second magnetic field extending along longitudinal axis 170 in a direction toward the first electrical coil 151. As such, when both the first electrical coil 151 and the second electrical coil 161 are energized to generate the opposing first magnetic fields 156 and the second magnetic fields 166, a resultant magnetic field may be generated in one or more portions within area 150A lying between the first and second electrical coils. The resultant magnetic field 150B may have a direction and field strength based on the resultant vector having a direction and a magnitude dictated by the superposition principle resulting from the interaction of the first magnetic field 156 and the second magnetic field 166.

In some examples where the level of current I-1 provided to the first electrical coil 151 is equal to the level of current I-2 provided to the second electrical coil 161, the resultant magnetic field 150B may have a direction that is perpendicular to the longitudinal axis 170 in one or more portions of area 150A. These portions of area 150A where the resultant magnetic fields may be perpendicular or substantially perpendicular to the longitudinal axis 170 may include portions of area 150A that are near the vertical axis 175 and are also a minimum distance away from the intersection of the longitudinal axis 170 and horizontal axis 176 as these axes are illustrated in FIG. 8B. An illustrative device 150C, which may be an implantable medical device that includes a receive antenna (e.g., in the form of a third coil), and configured to have a current inductively coupled to the antenna through the magnetic fields generated within area 150A, may be positioned between the first electrical coil 151 and the second electrical coil 161 as illustrated in FIG. 8B. In some examples, the resultant magnetic field 150B that may be generated by the first electrical coil 151 and the second electoral coil 161 in the area 150A between the coils where device 150C is positioned may be substantially perpendicular to the longitudinal axis 170, as illustratively shown by arrow 150B in FIG. 8B. Thus, when energized by the flow of currents "I-1 and "I-2," coils 151 and 161, respectively, may be configured to generate opposing magnetic fields 156, 166 that interact to form the resultant magnetic field (150B) in one or more portions of area 150A, the resultant magnetic field having an angle of direction that is substantially perpendicular to longitudinal axis 170 within certain portions of area 150A.

The resultant magnetic field (150B) may be used to provide energy to an implanted medical device, such as device 150C, when the device is located within the portions of areas 150A providing the resultant magnetic field. In addition, the positional angle θ (theta) of rotational orientation of the receive antenna, (e.g., the third coil of the implanted medical device placed within the resultant magnetic field 150B) relative to a longitudinal axis 170 extending between coils 151 and 61, may be rendered irrelevant with respect to the level of inductive coupling efficiency achieved between the electrical power of the resultant magnetic fields being provided by the first and second electrical coils 151, 161 and the receive antenna (third coil) of the device 150C when device is located within portions of area 150A that provide the resultant magnetic field 150B that is generally perpendicular to longitudinal axis 170.

In addition, as further described below the resultant magnetic field 150B may be further steered by controlling the relative strengths of the magnetic fields 156, 166 so that the resultant magnetic field 150B may be bent in a direction having an angle that is not perpendicular to the longitudinal axis 170. This bending may be used to further maximize the coupling efficiency between the electrical power begin provided by the first and second electrical coils 151, 161 and the electrical power induced in receive antenna of device 150C by further alignment of the resultant magnetic field 150B with an angle of orientation φ (phi) between the normal axis of the receive antenna of device 150C and the longitudinal axis 170. An alignment of the resultant magnetic field 150B with the normal axis of orientation of the receive antenna of device 150C provides a better level of coupling efficiency for inducing current into the receive antenna for a given level of energy being provided the resultant magnetic field 150B in the area of the device 150C.

This remaining (third) axis of orientation for the receive antenna of device 150C relative to the orientation of the magnetic fields being generated by the energization of the first and second electrical coils 151, 161 may be addressed by physical positioning of the first and second electrical coils 151, 161, including rotational positioning of the first and second electrical coils, relative to a third axis of orientation of the receive antenna of the device 150C. As such, each axis of orientation of a third coil being used to receive electrical power induced into the coil by the magnetic fields provided by the energization of the first and second electrical coils 151, 161 may be addressed using only one pair (a single pair) of coils energized to provide an opposing magnetic field, and by locating the third coil within certain portions of the resultant magnetic field generated in an area 150A between the single pair of coils. By adjusting the relative strengths of the opposing magnetic fields being generated by the energization of each of the first and second (recharging) coils, an effective level of coupling between the resultant magnetic field and the axis of orientation of a uni-directional antenna, such as a planar antenna of the medical device, may be achieved.

In various examples, each coil used to form one of the first electrical coil 151 or the second electrical coil 161 in the recharging systems of the examples described herein may be provided as a circular-shaped winding having a radius (such as radius 154, 164 as shown in FIG. 8B) in a range of 10 to 30 inches (25.4 to 76.2 centimeters), and a spacing between the coils (distance 171) equal to the radius, thus in a range of 10 to 30 inches 25.4 to 76.2 centimeters). In various examples, the radii 154, 164 may be approximately 15.4 inches (i.e., 39.0 centimeters). In various examples, the winding forming each of coils 151, 161 provide a DC resistance in a range of 100 to 5,000 mΩ, or a self-resonant frequency of 500 to 3,000 kHz. In various examples, the electrical energy provided by an electrical power source used to energize coils 151, 161 comprises a time modulated signal that can be a sine/cosine, square wave, sawtooth or another waveform. In various examples, an oscillator providing the time-modulated signal is coupled to a power amplifier, the output of the power amplifier is routed through a matching network to the first and second electrical coils 151, 161.

In various examples, the power supply, the power supplies, or the individually controllable power supply outputs that are coupled to coils 151, 161 may be coupled to the coils through one or more matching networks. The matching network(s) may be configured to maximizes the power transfer to the transmit coil by minimizing voltage/current reflection. The power delivered to the load (e.g., first electrical coil 151 and second electrical coil 161) may be between 100 and 400 W. The corresponding peak current in some examples is between 5 and 15 amperes. The peak voltage across the coils can be as high as 40 kV. The voltage wave in some examples is largely out of phase with the current wave. In various examples, the electrical energy provided to the coils 151, 161 is determined in conjunction with the electrical parameter associated with the coils to provide a resultant magnetic field intensity in portions of area 150A in a range of 50 to 1,000 A/m, and not to exceed a predetermined value, for example not to exceed a value of 1,500 A/m, for the safety of the patient.

Figure 8C:
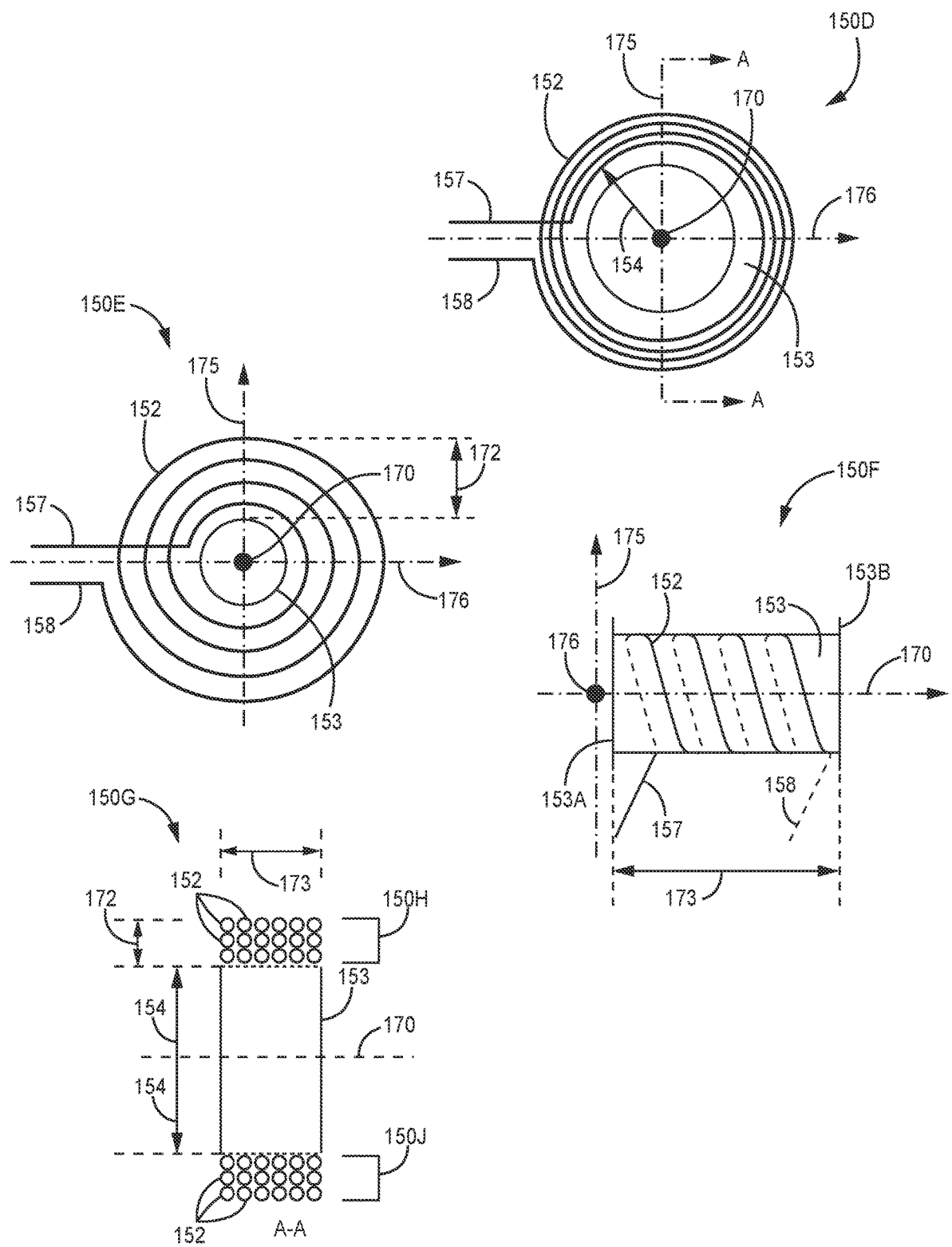
FIG. 8C illustrates various examples of winding techniques for the electrical coils that may be used in a recharging system according to various examples described in this disclosure.

FIG. 8C includes diagrams showing various examples of winding techniques that may be used to construct one or more of the electrical coils for use in the recharging systems described in this disclosure. The illustrations provided in FIG. 8C are not necessarily drawn to scale, are intended to illustrate winding techniques for electrical coils, and do not necessary illustrate relative sizes, dimensions, and/or scales of the devices illustrated. The first electrical coil 151 is illustrated in the diagrams of FIG. 8C for illustrative purposes. In diagram 150D as shown in FIG. 8C, coil 151 is illustrated as viewed from a direction having the longitudinal axis 170 of coil 151 turned so that longitudinal axis 170 as viewed in FIG. 8C is orientated directly into the plane of the drawing sheet, perpendicular to both the vertical axis 175 and the horizontal axis 176 that are substantially co-planar with the winding 152 of coil 151, and perpendicular to each other. Winding 152 may be formed form from a length of an electrical conductor, such as a wire, formed around support structure 153 by a plurality of windings encircling the longitudinal axis 170 at a distance of radius 154, and having a thickness 172. A cutaway view A-A of the windings 152 of coil 151 is further illustrated and described with respect to diagram 150G. Details shown in diagrams 150E, 150F, and 150G will be described below using the axes shown in diagram 150D of the first electrical coil 151 for orientation purposes relative to the views illustrated in these further diagrams as shown in FIG. 8C.

Diagram 150E is an illustrative example of the winding 152 formed from the electrical conductors of coil 151 being "flat spiral-wound" around the perimeter of support structure 153 to form coil 151. As shown in diagram 150E, coil 151 is illustrated as viewed from a direction having the longitudinal axis 170 of coil 151 turned so that longitudinal axis 170 is orientated directly into the plane of the drawing sheet, perpendicular to both the vertical axis 175 and the horizontal axis 176 that are substantially co-planar with the winding 152 of coil 151, and perpendicular to each other. As shown in diagram 150E, each layer of the winding 152 of coil 151 is wound so that all windings are coplanar relative to one another, and starting at the first input lead 157 having an initial winding closest to longitudinal axis 170, and spaced away from longitudinal axis 170 by a distance of radius 154. The additional winding of winding 152 are formed around and surrounding the initial winding closest to first input lead 157, and form a spiral shape surrounding the longitudinal axis 170 at an increasingly larger distance from the longitudinal axis 170 as each winding is added to coil 151, extending to a second input lead 158. As shown in diagram 150E, the layers of windings surrounding support 153 and extending between the first input lead 157 and the second input lead 158 have a thickness 172 that surrounds the longitudinal axis around an outside perimeter of the support structure 153.

Diagram 150F in FIG. 8C is an example illustrating the electrical conductor of winding 152 being spiral wound to form a solenoid type winding around support structure 153. Coil 151 is illustrated in diagram 150F as viewed from a direction having the longitudinal axis 170 orientated horizontally across the diagram, and horizontal axis 176 turned so that horizontal axis 176 is orientated directly into the plane of the drawing sheet, perpendicular to both the vertical axis 175 and the longitudinal axis 170. As shown in diagram 150F, first input lead 157 of winding 152 is wound near one end 153A of the support structure 153, and consecutive windings are formed along support structure 153 in a direction along longitudinal axis 170 toward a second end 153B of support structure 153 to a second input lead 158, so that winding of winding 152 as formed between first input lead 157 and second input lead 158 are substantially a same distance away from longitudinal axis 170. The windings of winding 152 thus extend along support structure 153 for a distance forming a width 173 of the winding.

In some examples, a combination of the winding techniques of diagram 150E and 150F may be used. For example, a first layer of electrical conductor forming winding 152 may be formed as a solenoid type winding as shown in diagram 150F, and then another layer of windings formed above the first layer of windings, in a manner similar to that shown in diagram 150E, forming layers of windings, but wherein each layer includes a plurality of windings of the electrical conductor that are wound in a solenoid type winding. In various examples, the total number of these layers of solenoid type windings formed as one set of windings surrounding another set of windings is not limited to any particular number of layers of windings, and may include a plurality of layers forming coil 151.

Diagram 150G in FIG. 8C is a cut-away view A-A illustrative of an example of the winding 152 formed from the electrical conductors of coil 151 comprising windings using a combination of the spiral windings illustrated in diagram 150F, layered with additional layers of winding as illustrated in diagram 150E. Coil 151 is illustrated in diagram 150G as viewed in cutaway and from a direction having the longitudinal axis 170 orientated horizontally across the diagram, and horizontal axis 176 turned so that horizontal axis 176 is orientated directly into the plane of the drawing sheet, perpendicular to both the vertical axis 175 and the longitudinal axis 170. As shown in diagram 150G, portion 150H of winding 152 is located above longitudinal axis 170 and away from the longitudinal axis by a distance of at least radius 154. The winding 152 having a thickness 172 extending in a directing perpendicular to the longitudinal axis 170, and a width 173 extending in a direction parallel to the longitudinal axis 170. The cross-sectional shape of winding 152 within portion 150H may be defined by a two-dimensional shape such as a square or a rectangle having the thickness 172 and the width 173 dimensions. The shape of the winding 152 in cross-section illustrated in portion 150H is not limited to any particular shape, and may include shapes other than square or rectangular shape, such as a circular or elliptical shape in cross section.

Similarly, a portion 150J of winding 152 may be located below longitudinal axis 170 and away from the longitudinal axis by a distance of at least radius 154. The winding 152 in portion 150J may be a same shape as the shape of portion 150H, and having a same thickness 172 extending in a directing perpendicular to the longitudinal axis 170, and a same width 173 extending in a direction parallel to the longitudinal axis 170. The cross-sectional shape of winding 152 within portion 150J may be defined by a two-dimensional shape such as a square or a rectangle device by the thickness 172 and the width 173 dimensions. The shape of the winding 152 in cross section illustrate in portion 150J is not limited to any particular shape, and may include a same shape other than square or rectangular shape, such as a circular or elliptical shape in cross section that corresponds to the shape of the winding 152 provided in cross-section by portion 150H.

In various examples, the electrical conductor used to wind coil 151 is Litz wire, for example a single or multiple stranded wire, wherein the electrical conductor used to form each winding 152 is insulated along the outer surface of the electrical conductor, for example using a coating, such as enamel, to reduce the skin effect of the electrical conductor. Skin effect is the characteristic of electrical current flowing through an electrical conductor that causes the flow of current in the electrical conductor to travel though the outer portion, e.g., the "skin" of the conductor, and not through the inner portion of the electrical conductor. The skin effect is more pronounced at higher frequencies. The use of Litz wire helps reduce the skin effect in the electrical conductor at higher frequencies. In addition, the inter-turn capacitance of the respective windings/turns is reduced by increasing inter-turn distances, thus increasing the self-resonant frequency of the assembly and enabling higher modulation frequency to be applied to the coil.

Details related to first electrical coil 151 are equally applicable to examples of the winding techniques that may be used to construct a second electrical coil such as second electrical coil 161 shown in FIG. 8B, and that may be paired with and arranged to generate a resultant magnetic field using opposing magnetic fields as described throughout this disclosure, and any equivalents thereof. Any of the windings illustrated in diagrams 150D, 150E, 150F, and 150G, and other winding techniques as would be understood by one of ordinary skill in the art, are contemplated for use in forming coils 151, 161 and may be used in forming any other examples of coils described throughout this disclosure described as being utilized as recharging coils in a charging system.

Figure 9A:
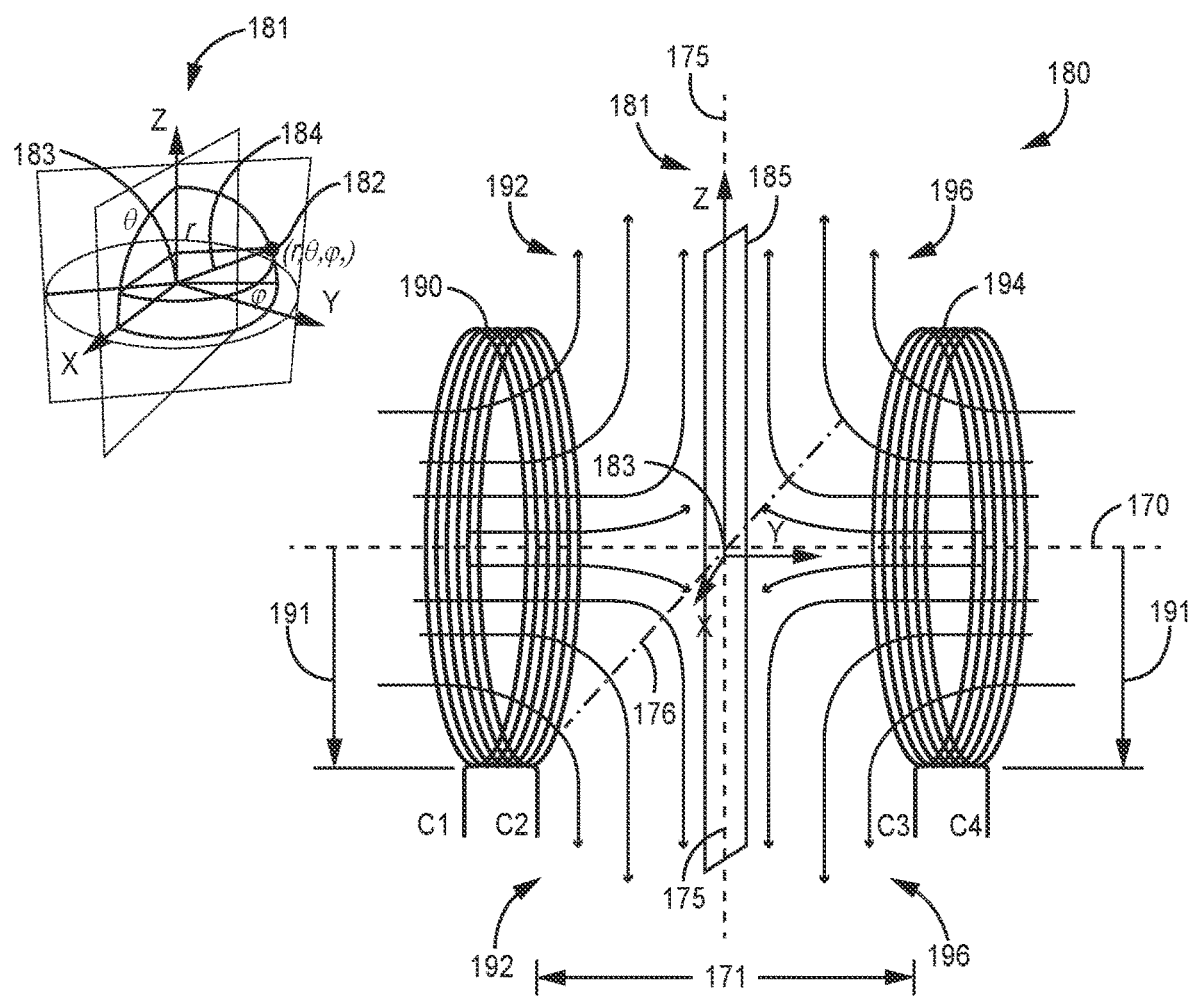
FIG. 9A is a conceptual drawing illustrating a pair of coils and electromagnetic fields generated by energization of the pair of coils according to various examples described in this disclosure.

FIG. 9A illustrates a conceptual diagram of a portion of a recharging system 180 including an example pair of electrical coils 190, 194, according to various examples described in this disclosure. In various examples, the pair of electrical coils 190, 194 correspond to the pair of coils 102, 103 illustrated and described with respect to recharging system 100 and FIG. 7, wherein coils 190, 194 may be configured to perform any of the functions and to provide any of the features ascribed to coils 102 and 103 as part of a charging system such as recharging system 100. Coils 190 and 194 may be electrically coupled to a single power source, for example as illustrated and described with respect to wiring diagram 130 and FIG. 8A, or may be electrically coupled to different power sources, or to separately adjustable outputs of a power supply, as illustrated and described with respect to wiring diagram 140 and FIG. 8A. Coils 190 and 194 as illustrated in FIG. 9A may correspond to any of the examples of coils 151 and 161 as illustrated and describe with respect to FIGS. 8B and 8C.

FIG. 9A includes an illustrative three-dimensional coordinate diagram 181 comprising X, Y, and Z axes intersecting at origin 183, and having each of the X, Y, and Z axes, respectively, perpendicular to the each of the other two axes. For illustrative purposes, a point 182 is shown in FIG. 9A that is located at a position within the three-dimensional coordinate diagram 181. Point 182 is located away from the origin 183 along line segment 184, wherein point 182 does not lie within any of the planes defined by a plane in which any two of the X, Y, and Z axes both lie. As shown in diagram 181, a value for r represents a radial segment 184 having a distance value for the radial segment extending between point 182 and the origin 183. A value for the angle θ represents an angular measurement formed by the radial segment 184 extending from the origin 183 to point 182 and forming an angle between the plane formed by the X and Y axes and the position of point 182 above the X/Y plane. A value for (p represents an angular measurement formed by the radial segment 184 extending from the origin 183 to point 182, the angle representative of the amount of angular rotation of the position of point 182 relative to a plane that includes both the Y and the Z axes.

As shown in FIG. 9A, the three-dimensional coordinate diagram 181 is also placed in position between the first electrical coil 190 and the second electrical coil 194. As shown in FIG. 9A, coils 190 and 194 each have a cylindrical shaped winding having a substantially circular shape formed around a hollow or through opening running through the center portion of each coil, respectively. For each of coils 190, 194, the coil itself may be formed of an electrical conductor, such as a wire, that is wound so that the windings of the electrical conductor are formed at a distance or fall at least a minimum distance away from and surrounding a longitudinal axis 170 extending through the center portion of the cylindrical shaped winding so that the windings are in substantially a same distance, or falls within a range of distances radially surrounding the longitudinal axis 170. The windings of each coil are formed so that the distance or a range of distances radially surrounding the longitudinal axis 170 includes a distance having a value defined by radius dimension 191 as shown in FIG. 9A. The windings for first electrical coil 190 comprise circular shaped windings, each circular shaped winding lying substantially in one of a plurality of planes that are coplanar to the X/Z plane 185, and the windings of the second electrical coil 194 comprise circular-shaped windings, each circular-shaped winding lying substantially in one of a plurality of planes that are also coplanar to the X/Z plane 185, and are on the opposite side of the X/Z plane 185 relative to the windings of the first electrical coil 190. In various examples, at least the portion of the windings of coil 190 closest to the windings of coil 194 relative to the direction of the longitudinal axis 170 are separated from on another by a distance 171. In some examples, a value for distance 171 is equal to a value for radius 191 of each of coils 190, 194.

As shown in FIG. 9A, coils 190 and 194 may be coupled to one or more electrical power sources (not shown in FIG. 9A, but for example electrical power source 133 or electrical power sources 143, 144 as shown in FIG. 8A). As shown in FIG. 9A, coil 190 may be energized to generate a magnetic field having a direction generally indicated by arrows 192, and coil 194 may be energized to generate a magnetic field having a direction generally indicated by arrows 196. When coils 190 and 194 are wired and energized in a way such that the coils provide magnetic fields having opposite directions, e.g., opposing magnetic fields, and having the strength of the electrical energy used to energize each of the coils 190, 194 arranged to be substantially equal, the resultant magnetic field generated in portions of the area between the coils may be directed in a radial direction relative to the origin 183 so that the direction of the resultant magnetic field lies in planes that are coplanar to the X/Z-plane 185 illustrated in FIG. 9A, and surrounding and extending in all directions away from the longitudinal axis 170. For example, the direction of the magnetic field 192 provided by coil 190 may be collinear with the longitudinal axis 170 (and Y-axis of diagram 181) in the area partially enclosed by coil 190. As the magnetic field 192 extends toward plane 185, the interaction between the magnetic field 192 generated by coil 190 and the magnetic field 196 generated by the second electrical coil 194 may cause the orientation of the magnetic field 192 to bend away from the longitudinal axis 170 (Y-axis of coordinate system 181) in all directions, eventually having an orientation that is substantially perpendicular to the Y-axis and lying in planes that are co-planer to plane 185.

In a similar but opposite manner, the direction of the magnetic field 196 provided by the second electrical coil 194 may be colinear with the longitudinal axis 170 (and the Y-axis of diagram 181) in the area partially enclosed by coil 194. As the second magnetic field 196 extends toward plane 185, the interaction with the first magnetic field 192 generated by the first electrical coil 190 may cause the orientation of the second magnetic field 196 to bend away from the Y-axis in all directions, eventually having an orientation that is substantially perpendicular to and surrounding the longitudinal axis 170, and lying in planes that are co-planer to plane 185. As a result of this bending of the opposing magnetic fields generated by coils 190 and 194, the resultant magnetic field in some portions of the area between coils 190 and 194 and at some distance away from the longitudinal axis 170 may be in a direction perpendicular to and surrounding the longitudinal axis 170 in a series of planes coplanar with plane 185.

In general, for a single coil when energized, the magnetic field generated can be represented as a vector "H" having a magnitude and a direction. The general expression for the magnetic field intensity for a single coil in cylindrical coordinates (typically denoted as the H-field or H) may be given as:

$$H_r = \frac{I}{2\pi} \frac{x}{r\sqrt{(a+r)^2 + x^2}} \left[ -K(k) + \frac{a^2 + r^2 + x^2}{(a-r)^2 + x^2} E(k) \right] \quad \text{Eq 1)}$$

$$H_x = \frac{I}{2\pi} \frac{1}{r\sqrt{(a+r)^2 + x^2}} \left[ K(k) + \frac{a^2 - r^2 - x^2}{(a-r)^2 + x^2} E(k) \right], \quad \text{Eq 2)}$$

where I is the current flowing through the single coil, a is the coil radius, x and r are the distances from the coil center along the coil's axial and radial axes, respectively. K(k) is a complete elliptic integral of the first kind and E(k) is a complete elliptic integral of the second kind. Little k is given by $k^2 = 4ar/[(a+r)^2 + x^2]$. Elliptic integrals are functions—much like sine and cosine—their values are typically given in lookup tables. (Tang, "A Low-Operating-Voltage Wireless Intermediate-Range Scheme for Energy and Signal Transmission by Magnetic Coupling for Implantable Devices," IEEE Journal of Emerging and Selected Topics in Power Electronics, Vol. 3, No. 1, March 2015, pp. 242-251). The individual magnetic fields obey the superposition principle, and therefore the solution of the magnetic field intensity for single coils can be summed vectorially to provide the solution of the magnetic field intensity when multiple coils are present.

The resultant magnetic field formed by the interaction of the magnetic field 192 generated by the energization of coil 190 and the energization of coil 196 may be provided in portions of the area between the coils 190 and 194 referred to as areas of an estimated optimal recharging envelope, or simply the recharging envelope. In some examples, these areas correspond to portions of the area between coil 190 and 194 that render a positional angle θ (theta) of rotation of the antenna of the implanted device around a longitudinal axis extending between the pair of recharging coils irrelevant with respect to the coupling of electrical power from the resultant magnetic fields to the third coil located within these areas. Further description and illustration of the positional angle θ (theta) and the angle of orientation φ (phi) between the normal axis of the third coil and the longitudinal axis extending between the recharging coils is provided below with respect to FIG. 9B. The areas that may be included in the recharging envelope for use in inducing an electrical current in a third coil introduced into the resultant magnetic field in these areas is further illustrated and described below with respect to FIGS. 10A, and 10B.

Figure 9B:
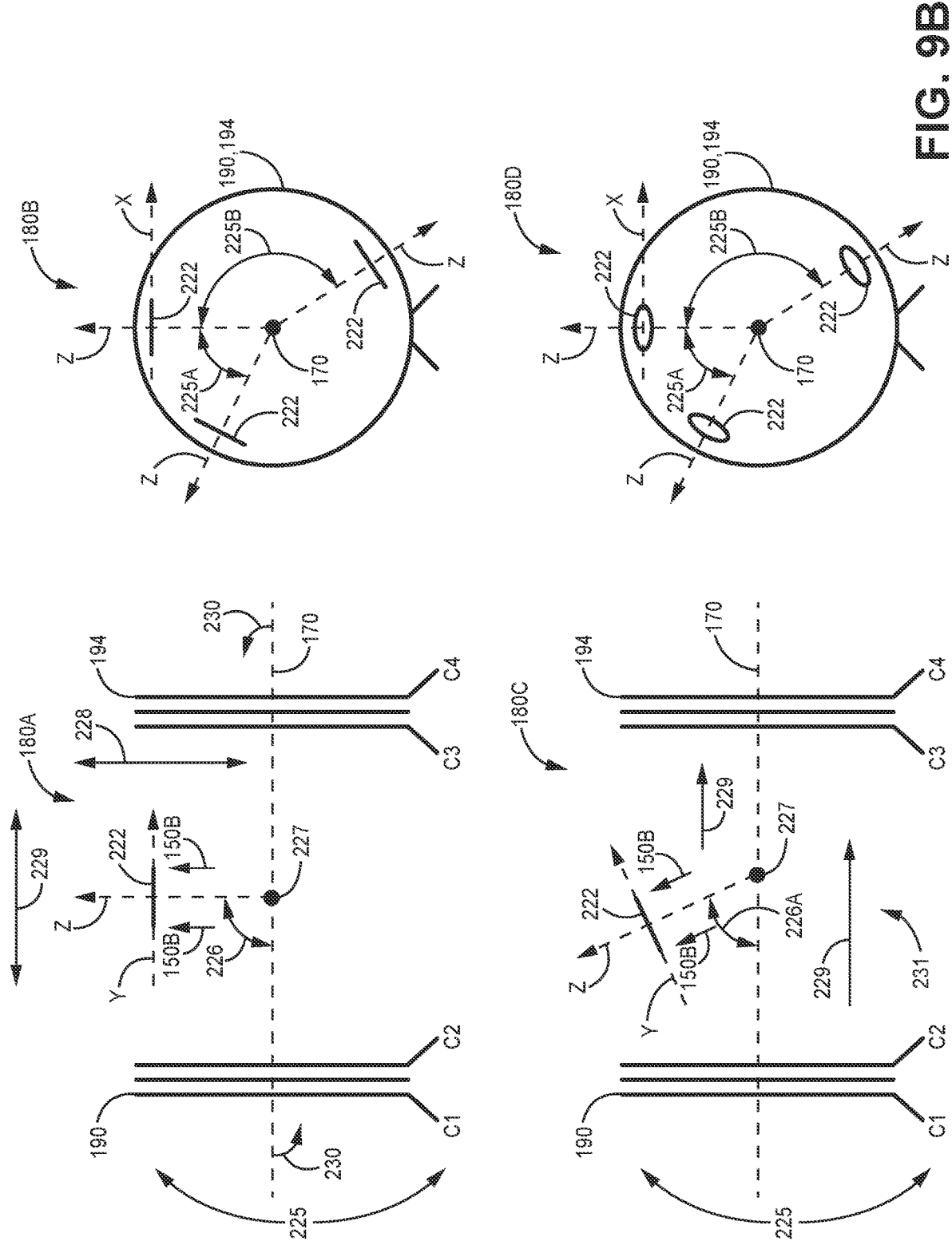
FIG. 9B is set of conceptual diagrams that illustrate various aspects relate to the positional angle θ (theta) and the angle of orientation φ (phi) as described throughout this disclosure.

FIG. 9B is set of conceptual diagrams 180A-180D that illustrate various aspects relate to the positional angle θ (theta) and the angle of orientation φ (phi) as described throughout this disclosure. Diagram 180A illustrates a simplified version of coils 190 and 194 as shown in FIG. 9A. As illustrated in diagram 180A of FIG. 9B, longitudinal axis 170 extends between the center points of the windings of coils 190 and 194. Third coil 222 is also illustrated in diagram 180A as positioned in the area between coils 190 and 194. Third coil 222 may be illustrative of a planar or another type of a receive antenna located in an implantable medical device (not shown in FIG. 9B) that may have a power source (not shown in FIG. 9B) coupled to third antenna 222, and that may be recharged using magnetic fields generated by coils 190 and 194 to induce electrical current into the third coil. Third coil 222 may be a type of coil that is uni-directional with respect to inductively inducing current into the third coil, wherein the Z-axis of the third coil 222 as illustrated in diagram 180A represents the normal axis for the third coil. In general, a magnetic field having a magnetic field direction that aligns with the Z-axis of third coil 222, (e.g., is a same direction as the orientation of the Z-axis of the third coil), should provide a maximum level of inductive coupling efficiently between the resultant magnetic field and the third coil for a given level of magnetic field intensity imposed on the third coil by the resultant magnetic field.

As illustrated in diagram 180A, third coil 222 is oriented such that the Z-axis of the third coil intersects longitudinal axis 170 at approximately the center point 227 along longitudinal axis 170 between coils 190 and 194. Third coil 222 lies in or is coplanar with a X-Y plane that is perpendicular to the Z-axis. The Y-axis of the X-Y plane as shown in diagram 180A is parallel to longitudinal axis 170, having a same orientation as longitudinal axis 170. An angle 226, also referred to as the angle of orientation φ (phi), is formed between the Z-axis of third coil 222 and longitudinal axis 170 in diagram 180A. In diagram 180A, the angle of orientation φ (phi) between the Z-axis and the Y-axis forms a ninety-degree angle. The X-axis of the X-Y plane of third coil 222 is orthogonal and perpendicular to both the Z-axis and the Y-axis of third coil 222, and in diagram 180A would extend directly into and extend directly out of the drawing sheet in diagram 180A. The X-axis and Y-axis of third coil 222 may define a plane (or a set of coplanar planes) in which the windings of the electrical conductor forming third coil 222 lie. The normal axis or Z-axis of third coil 222 intersects and is perpendicular this X-Y plane or set of coplanar planes where the windings forming third coil 222 lie.

In diagram 180A, a resultant magnetic field 150B that may be generated in the area of the third coil 222 by energizing coils 190 and 194 may be generated using opposing magnetic fields. The direction of the resultant magnetic field 150B in the area were third coil 222 is positioned extends in a perpendicular direction away from longitudinal axis 170 in all directions surrounding the longitudinal axis 170 at the mid-point (point 227) of longitudinal axis 170 between coils 190 and 194. In addition, the direction of the resultant magnetic field 150B in the area were third coil 222 is located has a direction that is the same as the orientation of the Z-axis of third coil 222. As such, the relative orientation of the resultant magnetic field 150B and the Z-axis (normal axis) of third coil 222 should provide a maximum level of inductive coupling efficiency for a given magnetic field intensity of the resultant magnetic field 150B for purposes of inducing current into third coil 222.

Further, the resultant magnetic field 150B has a same magnetic field direction as illustrated by the arrows in diagram 180A for all angles of rotation surrounding the longitudinal axis 170 at point 227 between coils 190 and 194. As such, regardless the positional angle θ (theta) of rotation of third coil 222 when rotating the Z-axis of third coil 222 around longitudinal axis 170 using point 227 as the center point of the rotation of the Z-axis and without any changes in the relative orientation of the X-Y plane relative to longitudinal axis 170, the resultant relative orientation of the resultant magnetic field 150B to the orientation of the Z-axis of third coil 222 will remain unchanged. As such, the level of the inductive coupling efficiency obtainable for a given level of magnetic field intensity represented by resultant magnetic field 150B with third coil 222 will remain unchanged irrespective of the positional angle θ (theta) of rotation of third coil 222 relative to longitudinal axis 170. In other words, when a pair of recharging coils, such as coils 190 and 194, are configured and energized to generate an opposing electromagnetic field between the coils, a positional angle θ (theta) of rotation of the third coil positioned within certain portions of the area between the coils, referred to as the estimated optical recharging envelope, around a longitudinal axis extending between the pair of recharging coils is rendered irrelevant as a factor in determining the efficiency of the inductively coupled power. This positional angle θ (theta) of rotation of third coil 222 is represented in diagram 180A as double-headed arrow 225 and is referred to as the positional angle θ (theta) of rotation of a receive coil, such as third coil 222, around a longitudinal axis extending between the pair of recharging coils, such as coils 190 and 194, as described through this disclosure.

As shown in diagram 180A, the relative distance along the Z-axis between point 227 and the X-Y plane where third coil 222 resides may vary in an up or down direction as represented by double-headed arrow 228. As also shown in diagram 180A the relative distances between the third coil 222 and each of coils 190 and 194 may vary in a left or right direction (i.e., parallel to the orientation of longitudinal axis 170), as represented by double-headed arrow 229. Regardless of the variations in position of third coil 222 in the up/down or left/right directions as illustrated in diagram 180A, a same level of inductive coupling efficiency between coil 190, 194 and third coil 222 will be maintained for any positional angle θ (theta) of rotation of the third coil relative to the longitudinal axis 170 as long as the positioning of third coil 222 remains within the estimated optical recharging envelop. The estimated optical recharging envelop (or simply the "recharging envelope") in some examples comprises a toroid-shaped volumetric area surrounding the longitudinal axis at approximately point 227, and including the areas in diagram 180A where third coil 22 is positioned, along with any position third coil 222 would be positioned at when rotation the Z-axis of third coil 222 around the longitudinal axis 170 using point 227 as the center of rotation.

The actual shape and dimensions of an estimated optical recharging envelop that may be generated by opposing magnetic fields is dependent on factors including the shape, size, relative orientation of the recharging coils being used to generate the opposing magnetic fields, and strengths of the opposing magnetic fields generated by the pair of recharging coils, such as coils 190, 194. Additional illustration and description of examples of an estimated optimal recharging envelop that may be generated by a pair of recharging coils such as coils 190, 194 is illustrated and described below with respect to FIGS. 10A and 10B.

Diagram 180B of FIG. 9B illustrates a side view of the arrangement of coils 190, 194 and third coil 222 as illustrated and describe with respect to diagram 180A. In diagram 180B, longtail axis 170 is oriented so that the longitudinal axis extends directly into and out of the drawing sheet of FIG. 9B. The different example positional angles θ (theta) of rotation of third coil 222 are illustrated in diagram 180A. A first positional angle θ (theta) of rotation shows the Z-Axis of third coil 222 extending in a vertical orientation from point 227 and longitudinal axis 170. A second positional angle θ (theta) of rotation shows the Z-axis of third coil 222 extending at an angle of rotation 225A relative to the first position. A third positional angle θ (theta) of rotation shows the Z-axis of third coil 222 extending at an angle of rotation 225B relative to the first position. For each of the first, second, and third positions of rotation for third coil 222, the positional angle θ (theta) of rotation (represented by the vertical position of the Z-axis, and angles 225A, 225B) of the third coil around a longitudinal axis is irrelevant to the level of inductive coupling efficiency being achieved by resultant magnetic field 150B being imposed on third coil 222. Each of the first, second, and third positions, and any positional angle θ (theta) of rotation of third coil 222 for three-hundred and sixty degrees around point 227 and longitudinal axis 170 will not change the level of inductive coupling efficiency being achieved between coils 190, 194 and third coil 222. As such, the positional angle θ (theta) of rotation of the third coil around longitudinal axis 170 extending between the pair of recharging coils 190, 194 remains rendered irrelevant as a factor in determining the level of inductive coupling efficiency between the recharging coils 190, 194 and third coil 222 as long as third coil 222 is maintained within the estimated optical recharging envelop being generated by the opposing magnetic fields being generated by coils 190 and 194.

Diagram 180C in FIG. 9B illustrates a variation of the arrangement of coils 190, 194, and third coil 222 presented in diagram 180A. As shown in diagram 180C, third coil 222 is positioned between coils 190, and 194, and is assumed to be within the estimated optimal recharging envelope being generated by coils 190 and 194. Third coil 222 is spaced at some distance from point 227 and longitudinal axis 170. In contrast to diagram 180A where the Z-axis of third coil 222 is perpendicular to longitudinal axis 170, in diagram 180C the orientation of the Z-axis of third coil 222 is rotated around the X-axis of the X-Y plane so that the angle 226A formed between the Z-axis of third coil 222 and the longitudinal axis 170 is less than ninety-degrees, (i.e., is non-perpendicular to the longitudinal axis). As a result, the orientation of the Y-axis of third coil 222 is no longer parallel to the longitudinal axis 222, and if the Y-axis were extended in diagram 180C would intersect the longitudinal axis 170 at some point. As further described below (see e.g., description associated with FIG. 12), the relative strengths of the individual magnetic fields being generated by coils 190 and 191 may be varied in order to "steer" the direction of the resultant magnetic field 150B generated in the area between the coils. As shown in diagram 180C, the resultant magnetic field 150B has be altered relative to the direction of the resultant magnetic field 150B, as illustrated in diagram 180C, so that resultant magnetic field 150B in diagram 180C aligns with a same orientation as the Z-axis of third coil 222.

As such, the different orientation of the Z-axis at angle 226A as illustrated in diagram 180C has been compensated for by steering the resultant magnetic field 150B so that the resultant magnetic field 150B realigns with the new orientation of the Z-axis of third coil 222. As such, a high or maximum level of inductive coupling efficiency, similar to the level achieved using the arrangement illustrated in diagram 180A, may be achieve in the arrangement illustrated in diagram 180C, despite the change in angle 226 to angle 226A, by applying steering to the resultant magnetic field 150B through the control of the relative strengths of the individual magnetic fields being generated by each of coils 190 and 191, respectively. This same high or maximum level or inductive coupling efficiency is maintained for the arrangement of coils 190, 191, and third coil 222 despite the positional angle θ (theta) of rotation of third coil 222 around a longitudinal axis 170 extending between the pair of recharging coils, as further illustrated in diagram 180D. This feature holds true despite the change in the value of the angle of orientation φ (phi) from vertical (angle 226) in diagram 180A and 180B to the new angle 226A illustrated in diagram 180C and 180D.

Diagram 180D of FIG. 9B illustrates a side view of the arrangement of coils 190, 194 and third coil 222 as illustrated and described with respect to diagram 180C. In diagram 180D, longitudinal axis 170 is oriented to extend directly into and out of the drawing sheet of FIG. 9B. The different example positional angles θ (theta) of rotation of the third coil 222 are illustrated in diagram 180D. A first positional angle θ (theta) of rotation shows the Z-axis of third coil 222 extending in a vertical orientation from point 227 and longitudinal axis 170, with the Y-axis of third coil 222 tilted to angle 226A. A second positional angle θ (theta) of rotation shows the Z-axis of third coil 222 extending at an angle 225A relative to the first position, with the Y-axis of third coil 222 tilted to angle 226A. A third positional angle θ (theta) of rotation shows the Z-axis of third coil 222 extending at an angle 225B relative to the first position, with the Y-axis of third coil 222 tilted to angle 226A. For each of the first, second, and third positions of third coil 222 in diagram 180D, the positional angle θ (theta) of rotation (represented by the vertical position of the Z-axis and the Z-axis rotated to angles 225A, 225B) of the third coil 222 around a longitudinal axis 170 extending between the pair of recharging coils is irrelevant to the level of inductive coupling efficiency being achieved by resultant magnetic field 150B being imposed on third coil 222. Each of the first, second, and third position, and any angle of rotation for three-hundred and sixty degrees around point 227 and longitudinal axis 170, will not change the level of inductive coupling efficiency being achieved between coils 190, 194 and third coil 222. As such, the positional angle θ (theta) of rotation of the antenna of the implanted device around a longitudinal axis extending between the pair of recharging coils is rendered irrelevant as a factor in determining the efficiency of the inductively coupled power as long as third coil 222 is maintained within the estimated optical recharging envelope being provided by the opposing magnetic fields generated by the recharging coils 190 and 194, and within some variations of the orientation of the angle of orientation φ (phi) between the Z-axis and at least one other axis of orientation of the third coil that is perpendicular to the Z-axis (normal axis) of third coil 222.

The angle of orientation between the Z-axis (normal axis) of third coil 222 and the longitudinal axis 170 extending between coil 190 and 194 is referred to as the angle of orientation φ (phi) through this disclosure. As shown in diagram 180C, at least some amount of variation in the angle of orientation φ (phi) can be compensated by "steering" the resultant magnetic field being imposed on the third coil 222. In each of diagrams 180A, 180B, 180C, and 180D, a third axis of orientation of third coil 222, the X-axis, remained in a same orientation regardless of the variations in the positional angle θ (theta) of rotation and the changes in the variations in angle of orientation φ (phi). However, variations in the angle of orientation of the X-axis relative to the longitudinal axis 170 may also occur, and would be represented for example by tilting of the Z-axis to point more into or to point more out of the drawing sheet in diagrams 180A and 180C, for example by rotation of the Z-axis around the Y-axis of the X-Y plane using the intersection of the X-axis and the Y-axis as the center of the rotation. At least some angular amount of change in the orientation of the X-axis may be compensated for by rotation of the coils 190, 194 and the orientation of the longitudinal axis 170 around point 227 as illustratively represented by double-headed arrow 230. In other words, and by way of example, longitudinal axis 170 may be rotated around point 227 so that coil 190 rotates in a direction extending out of the drawing sheet, and coil 194 rotates in a direction into the drawing sheet. The maximum amount of rotation of coils 190 and 194 around point 227 that may need to compensate for changed in the relative angles or orientation between the X-axis of third coil 222 and longitudinal axis 170 is ninety degrees of rotation.

As described above, steering of the resultant magnetic field 150B to compensate for variations in the angle of orientation φ (phi) of the Y-axis relative to the longitudinal axis 170 may be limited to some minimum value for angle 226A. For example, as angle 226A decreases in value, thus decreasing the angle of orientation between the Z-axis and longitudinal axis 170, more steering in the form of a lager difference in the relative strengths of the individual magnetic fields being generated by coils 190 and 194 may be required to align the resultant magnetic field 150B to the smaller angle of orientation φ (phi). In addition, as the angle of orientation φ (phi) becomes smaller, the angle of orientation of the Z-axis becomes more similar, e.g., more closely aligned with the orientation of longitudinal axis 170. At some point where angle of orientation φ (phi) becomes small enough, a more efficient level of inductive coupling between the recharging coils 190, 194 and the third coil 222 may be achieved by reconfiguring the recharging coils to provide magnetic fields that have a same direction, respectively, instead of providing the opposing magnetic fields. In configuring the coils 190, 194 to provide magnetic fields having a same direction, the coils may in configured to operate like a Helmholtz coil, and provide a substantially uniform magnetic field having a direction extending from one of the recharging coils to toward the other recharging coil, for example as illustrated by arrows 229 in diagram 180C.

When operating the recharging coils 190, 194 to generate the uniform magnetic field having the direction 229 as shown in diagram 180C, the position of the third coil 222 relative to longitudinal axis 170 may no long be relevant as along as third coil 222 remains within the area between the coils 190, 194 generally indicated by area 231. The magnetic field intensity and direction of the resultant magnetic field being provided by coils 190 and 194 when configured to provide magnetic fields having a same direction may be a substantially uniform magnetic field having a same resultant magnetic field intensity and magnetic field direction, (e.g., as indicated by the direction of arrows 229 in diagram 180C, or a direction 180-degrees opposite the direction of arrows 229), throughout area 231 between the coils 190 and 194. As the angle 226A in diagram 180C becomes smaller, the X-Y plane of the third coil 222 gains an orientation that is more parallel to the coils 190 and 194, and more perpendicular to the orientation of longitudinal axis 170. As such, the relative angle between the resultant magnetic field 129 that can be provided by coils 190, 194 when operating to provide a magnetic field having a same direction becomes more similarly aligned with the orientation of the Z-axis of the third coil, and may result in a high level, or at least an adequate level of inductive coupling efficient for performing inductively coupled recharging of the devices of an implantable device coupled to third coil 222.

However, when operating recharging coils 190 and 194 to generate magnetic fields having a same direction, the option to "steer" that actual direction of the resultant magnetic field using adjustments to the relative strengths of the magnetic fields being generated by the individual coils 190, 194. The resultant magnetic field when operating the coils 190, 194 to generate magnetic fields having a same direction will generally extend in a direction that is parallel to the longitudinal axis 170 throughout the area between coils 190 and 194, as illustrated in diagram 180C.

A determination of whether to operate coils 190, 194 so as to generate opposing magnetic fields (with or without steering of the resultant magnetic field), or to operate coils 190, 194 to generate magnetic fields having a same direction is not limited to any particular value for the angle of orientation φ (phi) (angle 226A in diagram 180C), and in some examples may be determined empirically using feedback provide by the device receiving a level of current being induced into the third coil 222 during a recharging session using recharging coils 190 and 194 to induce a current into the third coil.

Figure 10A:
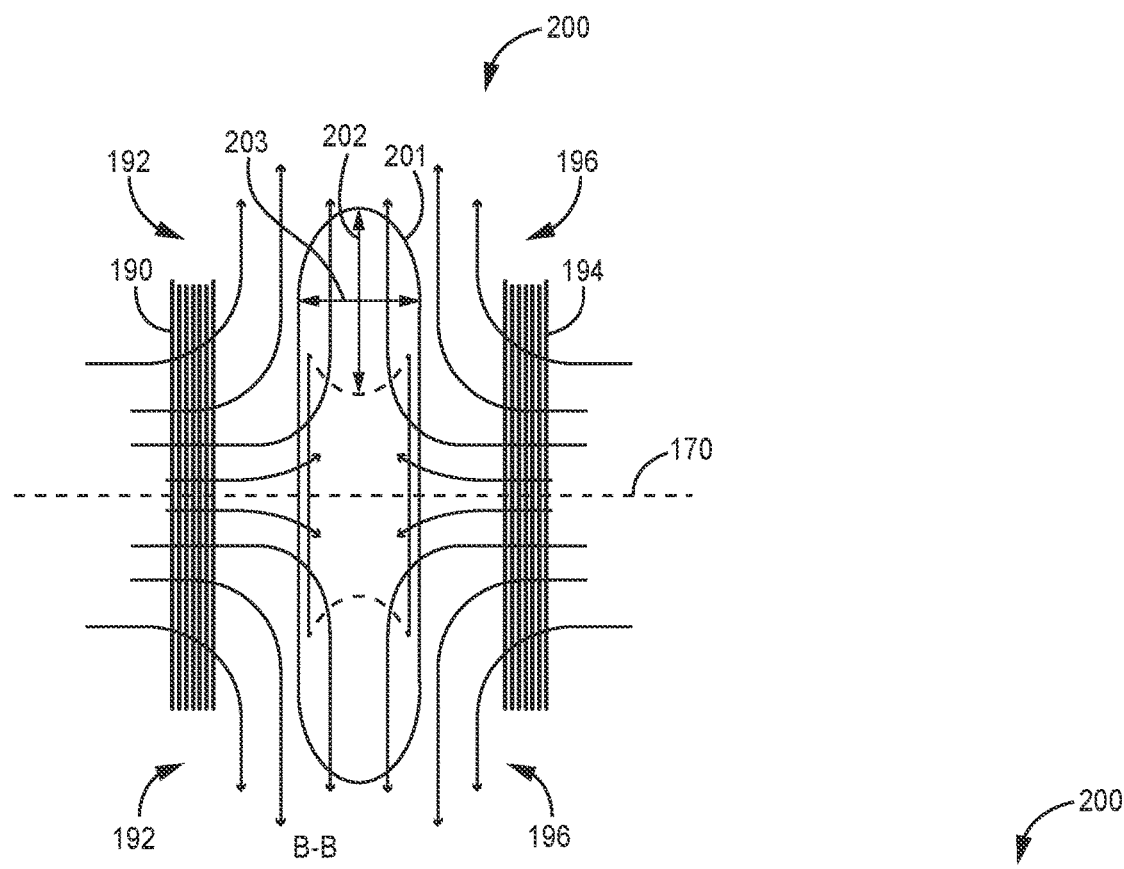
FIGS. 10A-10B are additional conceptual drawings illustrating a pair of coils and a recharging envelope generated by energization of the pair of coils according to various examples described in this disclosure.

FIG. 10A is a conceptual diagram 200 illustrating an estimated optimal recharging envelope (recharging envelope) 201 in according with the example techniques described herein. As shown in FIG. 10A, coil 190 and 194 are positioned relative to a longitudinal axis 170 and to each other in a manner illustrated and described above with respect to the first electrical coil 190 and the second electrical coil 194 as illustrated and described with respect to FIGS. 9A and 9B. As shown in FIG. 10A, when energized coil 190 may produce the magnetic fields generally indicated by arrows 192. When energized in a manner so that coil 194 provides a magnetic field opposing the magnetic field generated by the energization of coil 190, coil 194 may produce the opposing magnetic field generally indicated by arrows 196. The resultant magnetic field generated by the interaction of opposing magnetic fields 192 and 196 may, in some portions of the area between coils 190 and 194, extend in a radial direction that angles away from the longitudinal axis 170 in a direction that is perpendicular to the longitudinal axis beginning at some distance away from the longitudinal axis, and that surround the longitudinal axis 170. The portions of the area between coils 190 and 194 including the resultant magnetic field having a direction perpendicular to the longitudinal axis 170 may lie within the recharging envelope 201.

Figure 10B:
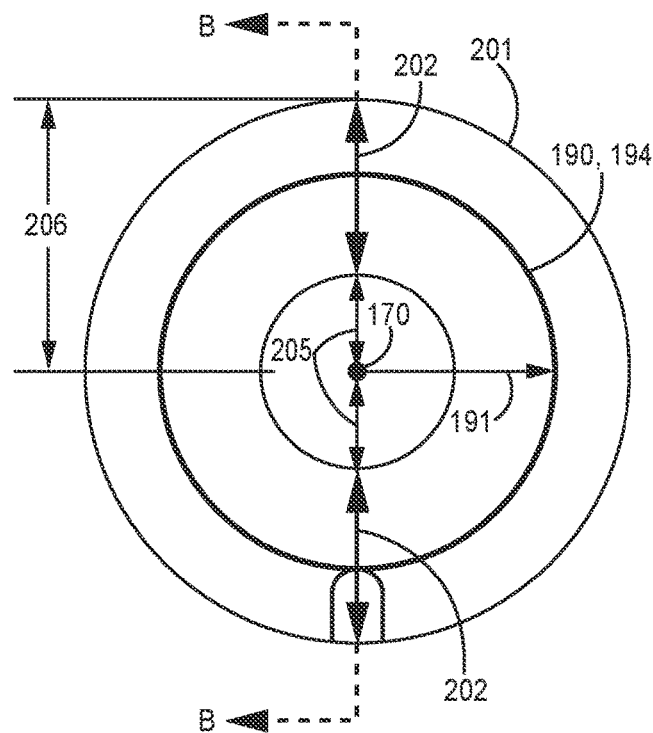

In FIG. 10A, the recharging envelope 201 is shown viewing the portion of envelope 201 from a direction that is perpendicular to longitudinal axis 170 and in cross-section B-B as taken from FIG. 10B. The area included within envelope 201 may be referred to as the estimated optimal recharging envelope or simply the recharging envelope. Within this area included within recharging envelope 201, the resultant magnetic field may exist where an optimal level of inductive coupling may be achieved between the resultant magnetic field being provided by the energization of coils 190, 194, and a third coil (not shown in FIG. 10A) that is placed within the envelope 201 relative to other areas between coils 190 and 194. In various examples, the recharging envelope 201 has a toroid shape, including an opening or through-hole surrounding the longitudinal axis 170, and having an elliptical or circular shape in cross-section in any cutting plane that includes the longitudinal axis 170 extending through the recharging envelope.

As shown in FIG. 10A, recharging envelope 201 in some examples includes first dimension 202 extending perpendicular to the longitudinal axis 170 in portions of recharging envelope, and a second dimension 203 extending perpendicular to the first axis 202 and parallel to the longitudinal axis 170 in all portions of the recharging envelope. In some examples, the length of the first axis 202 is larger than the length of the second axis 203, thus providing an elliptical shape to recharging envelope 201 in cross-section. As shown in FIG. 10A, recharging envelope 201 may be symmetrically positioned between the coils 190, 194, and symmetrical with respect to the shape of the envelope 201 in any cross-sectional plane that includes longitudinal axis 170 around the entirety of the recharging envelope. In some examples, portions of the recharging envelope may extend away from longitudinal axis 170 to a distance beyond the distance that the outermost portions of the windings of coils 190, 194 extend away from the longitudinal axis. Finally, the shape of the envelope may be controlled via dis-similar currents in the coils 190, 194, FIG. 11 as described earlier.

FIG. 10B is a side view of the estimated optimal recharging envelope 201 shown in FIG. 10A. As shown in FIG. 10B, recharging envelope 201 begins at a first radial distance 205 extending perpendicular in all directions from longitudinal axis 170, and extends to a second radial distance 206 extending perpendicular in all directions from longitudinal axis 170, having a cross-sectional dimension 202 extending between the first radial distance 205 and the second radial distance 206. As shown in FIG. 10B. the first radial distance 205 in some examples may be less than a radial distance 191 between longitudinal axis 170 and the windings forming coils 190 and 194, and the second radial distance 206 may be a distance that is greater than radial distance 191.

Figure 11:
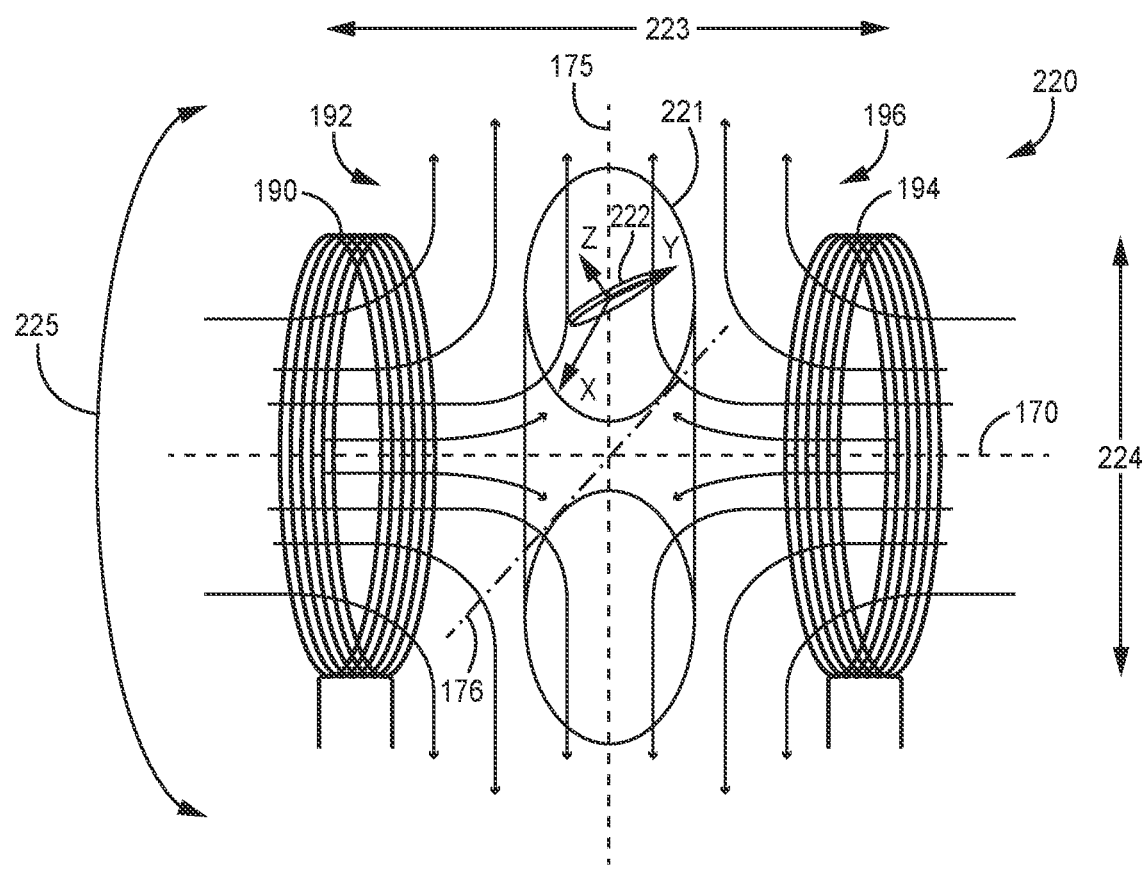
FIG. 11 is a conceptual diagram illustrating a pair of coils and a third coil placed in the electromagnetic fields generated by energization of the pair of coils according to various examples described in this disclosure.

FIG. 11 is a conceptual diagram 220 illustrating the pair of coils 190, 194 and the third coil 222 placed in the electromagnetic fields generated by energization of the pair of coils according to various examples described in this disclosure. Diagram 220 as illustrated in FIG. 11 includes a first electrical coil 190 and a second electrical coil 194, arranged for example as illustrated and described with respect to system 180 and FIG. 9A, and configured to generate the magnetic fields indicated as magnetic field 192 and magnetic field 196 when the first and second electrical coils are energized in a manner as described above with respect to system 180 and FIG. 9A. When energized, the resultant magnetic field generated by the interaction of the first magnetic field 192 and the second magnetic field 196 may include portions of the resultant magnetic field having an angle of direction that is perpendicular or substantially perpendicular to the direction of longitudinal axis 170 in any direction surrounding and at between some range of distances away from the longitudinal axis 170. These portions of the resultant magnetic field may be included within the recharging envelope 221 shown in FIG. 11. The area included within recharging envelope 221 may comprise an estimated optimal recharging envelop, such as the estimated optimal recharging envelope 201 as illustrated and described with respect to FIGS. 10A and 10B.

Referring again to FIG. 11, a third coil 222 may be positioned within the recharging envelope 221. Third coil 222 may be a receive antenna incorporated within an implantable medical device, such as any of IMDs 15 illustrate and described in this disclosure, or any other IMD that includes an antenna configured to have electrical power induced in the antenna for the purpose of providing electrical power to a device coupled to the antenna. Third coil 222 may be coupled to a power supply and/or electronic circuitry of the IMD, and may be arranged to inductively receive electrical power that is inductively coupled from the resultant magnetic field generated by the first electrical coil 190 and the second electrical coil 194. The electrical power received by the third coil 222 may be used to recharge a power source, such as a battery or other capacitive device, which is coupled to the third coil, and/or may be used to power the operation of the electronic circuitry included in the IMD or device having the third coil 222 as the power is being induced into the third coil 222.

As shown in FIG. 11, the third coil 222 may be positioned so that the third coil is within the recharging envelope 221, and thus is contained in its entirety within the estimated optimal recharging envelope generated by the first magnetic field 192 interacting with the second magnetic field 196. Third coil 222 includes an X-axis and a Y-axis perpendicular to the X-axis, and that lie in a plane that is coplanar with the plane or planes that include the windings forming the third coil 222. A Z-axis of orientation of the third coil 222 is perpendicular to both the X-axis and Y-axis, and is also perpendicular to the plane or planes that include the windings forming the third coil 222. The Z-axis may be referred to as the "normal vector" for third coil 222. A maximum level of magnetic flux may be induced to the third coil 222 when the third coil 222 is positioned within the estimated optimal recharging envelope and the direction of the resultant magnetic field imposed on the third coil 222 aligns with, e.g., has a same direction as, the orientation of the Z-axis (normal vector) of the third coil 222.

In some examples, the first and second electrical coils 190, 194 and/or the third coil 222 may be moved in the directions indicated by arrow 223, e.g., to the left or right in FIG. 11, to position the third coil 222 relative to the vertical axis 175 so that the third coil 222 is positioned within the recharging envelope 221. In addition, the first and second electrical coils 190, 194 and/or the third coil 222 may be moved the directions indicated arrow 224, e.g., up or down in FIG. 11, to position the third coil 222 within a range of distances away from the longitudinal axis 170, for example in the direction of vertical axis 175, so that the third coil is positioned with the recharging envelope 221 with respect to the distance from the third coil 222 to the longitudinal axis 170. In various examples, the first and second electrical coils 190, 194 may be moved, for example tilted, to change the angle of longitudinal axis 170 relative to the axes of orientation of the third coil 222 (e.g., rotated around the horizontal axis 176), as indicated by arrow 225, while maintaining a same positional relationship between coils 190 and 194, and between coils 190 and 194 and the positioning of the third coil 222 relative to maintaining the position of coil 222 within recharging envelope 221. The tilting of coils 190, 194 may be performed to align the orientation of the resultant magnetic field being imposed on the third coil 222, e.g., have a same direction as, the Z-axis (normal vector) of the third coil 222, thus maximizing the level of magnetic flux being imposed on the third coil, and thus maximizing the coupling efficiency between the resultant magnetic field being generated by the coils 190, 194 and the electrical energy being induced in the third coil 222.

Feedback provided by an IMD coupled to the third coil 222 may include information indicative of the level of current being induced into the third coil 222 at any given time, and for a given position of the coils 190, 194 when the coils 190, 194 are energized. Based on this feedback information, adjustments to the position of the coils 190, 194 and/or third coil 222, and the relative orientation of the coils 190, 194 and/or the third coil 222, may be made in order to increase the level of coupling efficiency being achieved between the coils 190, 194 and the third coil 222. These adjustments may be made as part of a recharging process being performed to recharge an electrically rechargeable device, such as a battery that is coupled to the third coil 222, and/or when the energy being induced into the third coil 222 is being used to power the operation of an IMD that is implanted within a patient.

When positioned within the estimated optimal recharging envelope 221, the third coil 222 may have a planar orientation relative to the X, Y, and Z axes of the third coil as illustrated in FIG. 11. When the third coil 222 has a planar orientation as illustrated in FIG. 11, only certain orientations of the axes of the third coil will result in high level of energy being inductively coupled to the third coil by the resultant magnetic fields being imposed upon the third coil. One advantage of arranging coils 190 and 194 to provide the opposing magnetic field 192, 196 as illustrated in FIG. 11 is that a positional angle θ (theta) of rotation of the antenna of the implanted device around a longitudinal axis extending between the pair of recharging coils is rendered irrelevant as a factor in determining the efficiency of the inductively coupled power.

For example, as shown in FIG. 11 the third coil 222 is positioned within the estimated optimal recharging envelope 221, and having an X, Y, and Z axes that are tilted, e.g., do not align with the horizontal axis 176, the longitudinal axis 170, or the vertical axis 175, respectively, of the coils 190, 194. In other words, the orientation of the normal axis of third coil 222 may be random relative to the orientations of the longitudinal axis 170, the vertical axis 175, and the horizontal axis 176 of the pair of coils formed by coils 190 and 194. When positioned as shown in FIG. 11, a positional angle θ (theta) of rotation of the antenna of the implanted device around a longitudinal axis extending between the pair of recharging coils is rendered irrelevant as a factor in determining the efficiency of the inductively coupled power. Any change in the value of the positional angle θ (theta) of rotation of the antenna of the implanted device around a longitudinal axis coil will not cause an increase or a decrease in the level of the coupling efficiency of the electrical power induced in the third coil by the redundant magnetic field occurring within the envelope 221. Further, any rotational repositioning of coils 190 and 194 around the longitudinal axis 170, e.g., rotation of the coils in a plane that comprises the vertical axis 175 and the horizontal axis 176 around the longitudinal axis 170 that maintains a same physical relationship and spacing between the coils 190 and 194 will not cause an increase or a decrease in the level of the coupling efficiency of the electrical power induced in the third coil by the redundant magnetic field occurring within the envelope 221.

In addition, the first and second electrical coils 190, 194 may be configured to be rotated and/or tilted in physical position relative to the third coil 222, as generally indicated by arrow 225, and for example around the horizontal axis 176 while maintaining a same relative orientation and physical positioning of the first electrical coil 190 relative to the second electrical coil 194. By rotating and/or tilting the position of the first and second electrical coils 190, 194, the direction of the resultant magnetic field within recharging envelope 221 may be changed relative to the orientation of the axes of the third coil, and thus altering the alignment of the resultant magnetic field with respect to the orientation of the Z-axis (normal vector) of the third coil 222. The amount and direction of the tilting of the resultant magnetic field resulting from the tilting of the first and second electrical coils 190 and 194 may be provided in a manner that aligns the direction of the resultant magnetic field to have a same direction/orientation as the direction of the Z-axis (normal vector) of the third coil 222. When the orientation of the resulting magnetic field aligns with a same direction as the orientation of the Z-axis of the third coil 222, a maximum level of coupling efficient may be achieved with respect to the amount of electrical energy that is induced into the third coil 222, for any given level of energy provided by the resultant magnetic fields being imposed on the third coil.

For example, when alignment of the resultant magnetic field and the Z-axis of the third coil 222 is achieved as described above, the direction of the resultant magnetic field within recharging envelope 221 may be perpendicular to the direction of both the X-axis and the Y-axis of the third coil 222, and thus perpendicular to the plane or planes that include the windings of the third coil 222. This orientation may provide the maximum level of coupling efficiency for coupling electrical power between coils 190, 194 and the third electrical coil 222. By positioning the third coil 222 within the estimated optimal recharging envelope 221, and in some instances by further tiling the orientation of the first and second electrical coils 190, 194 to align the resultant magnetic field generated by the first and second electrical coils within the recharging envelope 221 with a third axis of orientation for the third coil 222, the maximum level of coupling efficiency may be achieved for power being induced into the third coil using only a single pair of electrical coils configured to generate the resultant magnetic field imposed on the third coil.

Control of the positioning and/or the tilting of coils 190, 194 may be based on feedback from the IMD coupled to the third coil 222, the feedback indicative of one or more parameters, such as the current level being induced into the third coil, that is indicative of the level of coupling efficiency being achieved between coils 190, 194 and the third coil 222. Control of the positioning and/or tilting of the coils 190, 194 may be performed manually by a user, such as a technician or physician, or may be performed automatically by a coil positioning system configured to reposition the coils 190, 194 and/or the patient having the IMD comprising the third coil 222.

Thus, by using the first and second electrical coils 190, 194 arranged to provide opposing magnetic fields, and thus generate portions of the area between the coils to include an estimated optimal recharging envelope as described above, a simple recharging system including only a single pair of electrical coils may be utilized to provide the electrical power that may be induced to a third coil 222 of an implanted medical device using the most efficient coupling between the coils used to generate the opposing magnetic fields and a third coil having a random and/or unknown orientation of the third coil. This efficient level of coupling may be achieved for devices that are deeply implanted within a patient and/or for devices wherein the exact orientation of the receiving coil into which the electrical power is being induced is not known, or is not known precisely.

Figure 12:
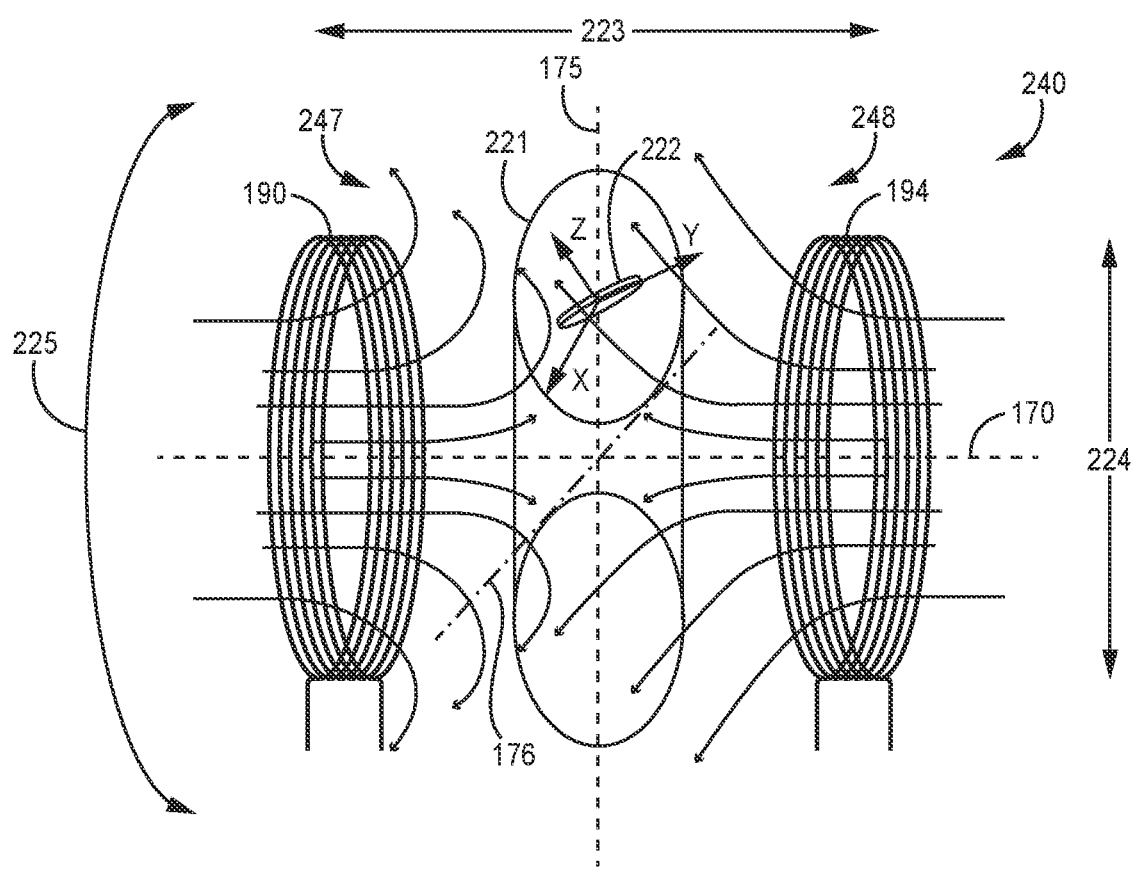
FIG. 12 is another conceptual diagram illustrating a pair of coils and a third coil placed in the electromagnetic fields generated by energization of the pair of coils according to various examples described in this disclosure.

FIG. 12 is another conceptual diagram 240 illustrating a pair of coils 190, 194 and a third coil 222 placed in the electromagnetic fields generated by energization of the pair of coils according to various examples described in this disclosure. Diagram 240 as illustrated in FIG. 12 includes first electrical coil 190 and second electrical coil 194 physically arranged and positioned for example as illustrated and described above with respect to system 180 and FIG. 9A. Referring again to FIG. 12, the coils 190, 194 may be configured to generate the opposing magnetic fields indicated as first magnetic field 247 and a second magnetic field 248, respectively, when the first and second electrical coils are energized. When energized, the resultant magnetic field generated by the interaction of the first magnetic field 247 and the second magnetic field 248 may include portions of the resultant magnetic field having a direction that is not parallel to longitudinal axis 170, and that is not perpendicular or substantially perpendicular to the direction of longitudinal axis 170, but instead extends at some non-perpendicular angle relative to each of the longitudinal axis 170, the vertical axis 175, and the horizontal axis 176, while surrounding the longitudinal axis 170. These portions of the resultant magnetic field may be included within the recharging envelope 221 shown in FIG. 12, wherein the area included within recharging envelope 221 may comprise an estimated optimal recharging envelope as illustrated and described with respect to FIGS. 10A and 10B.

Referring again to FIG. 12, third coil 222 may be positioned within the recharging envelope 221. The third coil 222 may be a receive antenna incorporated within an implantable medical device, such as any of IMDs 15 illustrate and described in this disclosure, or any other IMD that includes an antenna configured to have electrical power induced in the antenna for the purpose of providing electrical power to a device coupled to the antenna. Third coil 222 may be coupled to a rechargeable power source and/or electronic circuitry of the IMD, and may be arranged to inductively receive electrical power that is inductively coupled from the resultant magnetic field generated by the first electrical coil 190 and the second electrical coil 194. The electrical power received by the third coil 222 may be used to recharge a power source, such as a battery or other capacitive device that is coupled to the third coil, and/or may be used to power the operation of the electronic circuitry included in the IMD or device comprising the third coil 222 as the power is being induced into the third coil 222.

As shown in FIG. 12, the third coil 222 may be positioned so that the third coil is within the recharging envelope 221, and thus may be contained in its entirety with the estimated optimal recharging envelope generated by the first magnetic field 247 interacting with the second magnetic field 248. In some examples, the first and second electrical coils 190, 194 and/or the third coil 222 may be moved in the directions indicated by arrow 223, e.g., to the left or right in FIG. 12, to position the third coil 222 relative to the vertical axis 175 so that the third coil 222 is positioned with the recharging envelope 221. In addition, the first and second electrical coils 190, 194 and/or the third coil 222 may be moved the directions indicated by arrow 224, e.g., up or down in FIG. 12, to position the third coil 222 within a range of distances away from the longitudinal axis 170, for example along the direction of vertical axis 175, so that the third coil 222 is positioned within the recharging envelope 221.

As described above with respect to diagram 220 illustrated in FIG. 11, the resultant magnetic field generated within the recharging envelope 221 generated by the energization of coils 190 and 194 may be perpendicular to the longitudinal axis 170, and physical movement, e.g., tilting of the first and second electrical coils 190, 194 may be performed to align the resultant magnetic field with the Z-axis of the third coil 222. In comparison, and referring to diagram 240 as illustrated in FIG. 12, the adjustment of the direction of the portion of the resultant magnetic field generated within recharging envelope 221 by the energization of coils 190 and 194 may be "bent" or "steered" to some non-perpendicular direction by controlling the relative intensities of the opposing first magnetic field 247 and second magnetic field 248.

As illustratively shown in FIG. 12, the intensity of the second magnetic field 248 generated by the energization of the second electrical coil 194 is provided at a relative intensity level that is greater than the intensity level of the of the first magnetic field 247 generated by the first electrical coil 190. As a result of the interaction of these magnetic fields, a direction of the first magnetic field 247 generated by the energization of the first electrical coil 190 initially extends in a direction toward the second electrical coil 194 and parallel to the longitudinal axis 170 in the area proximate to the first electrical coil 190. As the first magnetic field 247 further extends away from the first electrical coil 190 and toward the second electrical coil 194, the first magnetic field 247 is bent or steered to directions that are initially perpendicular to the longitudinal axis, and then further bent or steered in directions forming angles that are not perpendicular to the longitudinal axis 170, and extends away from the vertical axis 175 and the horizontal axis 176 at some non-perpendicular and non-parallel angles that extends back toward the first electrical coil 190 and away for each of the longitudinal axis 170, the vertical axis 175, and the horizontal axis 176 and surrounding the longitudinal axis 170.

As a further result of the interactions of the magnetic fields, a direction of the second magnetic field 248 generated by the energization of the second electrical coil 194 initially extends in a direction toward the first electrical coil 190 and parallel to the longitudinal axis 170 in the area proximate to the second electrical coil 194. As the second magnetic field 248 further away from the second electrical coil 194 toward the first electrical coil 190, the second magnetic field 248 is bent or steered to directions forming angles that are not perpendicular to the longitudinal axis 170, that surround the longitudinal axis 170, and that extend toward from the vertical axis 175 and the horizontal axis 176 at non-perpendicular and non-parallel angles relative to these axes.

The amount of steering of the second magnetic field 248 is such that the direction of the angles of second magnetic field 248 in the area included within recharging envelope 221 is at angles that are less than ninety-degrees relative the longitudinal axis 170, never reaching a point where the direction of the second magnetic field 248 extends to be perpendicular to the longitudinal axis 170, but instead extends past the origin point beyond vertical axis 175 and horizontal axis 176 toward the first electrical coil 190. As a result, the direction of the second magnetic field 248 crosses both the vertical axis 175 and the horizontal axis 176 at an angle having a value of less than ninety-degrees relative to the longitudinal axis 170, and surrounding the longitudinal axis 170. The angle of the direction of the second magnetic field 248 may correspond, e.g. be a same or similar angle and have a same or similar set of direction for the angles of the first magnetic field 247 within portions of the resultant magnetic field that are included within envelope 221, and thus are congruent with the directions of the angles of the magnetic fields 247 within envelope 221.

Due to the interaction between the first magnetic field 247 generated by the first electrical coil 190 an the second magnetic field 248 generated by the second electrical coil

194, the resultant magnetic field conforms to the superposition principle, and at least within the envelope 221, has a direction that forms angles that are non-perpendicular and non-parallel to the longitudinal axis 170, and is also non-perpendicular and non-parallel to both the vertical axis 175 and the horizontal axis 176, and surrounds and extends away from the longitudinal axis 170 in all radial directions around the longitudinal axis. As shown in FIG. 12, the direction of the resultant magnetic field generated within envelope 221 may extend in directions that angle away from the second electrical coil 194 and toward the first electrical coil 190. The direction of the resultant magnetic field may be controlled by the relative strength of the first magnetic field 247 and second magnetic field 248, which in turn may be controlled by controlling the relative levels of energy, e.g., the level of current, that is being provided to the first and second electrical coils 190, 194, respectively. Control of the amount of "steering" provided by coils 190 and 194 may result in a resultant magnetic field generated within the recharging envelope 221 having a same angle of orientation as the angle of orientation φ (phi) between the normal axis of the third coil and the longitudinal axis. As such, the level of inductive coupling between the resultant magnetic field and the third coil 222 may be maximized for any given level of magnetic field intensity imposed on third coil 222. In addition, the level of coupling between the resultant magnetic field and the third coil is independent of the positional angle θ (theta) of rotation of the third coil 222 around a longitudinal axis 170 as long as the position of third coil 222 also remains within the recharging envelope 221.

For example, as shown in FIG. 12 the levels of current provided to the second electrical coil 194, and thus the intensity level of the second magnetic field 248, may be greater than the levels of current, and thus the intensity level of the first magnetic field 247. In this example, the greater level of energy provided to the second electrical coil 194 results in the second magnetic field 248 generated by the second electrical coil 194 being stronger than the first magnetic field 247 as generated by the first electrical coil 190. By virtue of the superposition principle, the interaction of the opposing magnetic fields results in the stronger second magnetic field 248 steering the weaker first magnetic field 247 so that the resultant magnetic fields formed within envelope 221 may be bent back toward the first electrical coil 190 as some angle that is non-perpendicular and non-parallel to both vertical axis 175 and horizontal axis 176 and surrounds the longitudinal axis 170.

The amount of the angle of steering of the resultant magnetic field may be a function of the relative strengths of the magnetic fields provided by the first and second magnetic fields, and thus can be varied and controlled by controlling the relative levels of energy (e.g., relative levels of current) being provided to the first and second electrical coils 190, 194. In another example, the level of energy provided to the first electrical coil 190 may be greater than the level of energy provided to the second electrical coil 194, and the first magnetic field 247 may extend past the origin at the intersection of the vertical axis 175 and the horizontal axis 176 so that the second magnetic field 248 is instead bent back toward the second electrical coil 194 in the area included within envelope 221.

By controlling the relative levels of energy being provided to the first and second electrical coils 190, 194, the angle and the direction of the resultant magnetic field within envelope 221, may be controlled. In various examples, the direction of the resultant magnetic field may be adjusted so that the direction of the resultant magnetic field within the recharging envelope 221 and where third coil 222 is positioned aligns with the orientation of an axis, such as the Z-axis, of the third coil 222 positioned within envelope 221. By control the direction of the resultant magnetic field being provided within the recharging envelope 221, alignment of the resultant magnetic field with a third axis of orientation of the third coil 222 positioned within the recharging envelope 221 may be achieve without the need to tilt or otherwise physically reposition the first and second electrical coils 190, 194 once the third coil 222 has been positioned within the recharging envelope.

Controlling the relative levels of energy being provide to each of the first and second electrical coils 190, and 194, and thus controlling the direction of the resultant magnetic field being generated within recharging envelope 221, may be accomplished in some examples by wiring the first electrical coil 190 and the second electrical coil 194 to separate power sources, for example as shown in wiring diagram 140 and described with respect to FIG. 8A. In some examples, the power sources as coupled to the first electrical coil 190 and the second electrical coil 194 as shown in FIG. 12 may be a same power source, but having separately controllable outputs that are coupled to and are configured to allow individual control of the level of energy being provide to each of the first electrical coil 190 and the second electrical coil 194. Control of the relative levels of energy provided to coils 190, 194 may be based on feedback from the IMD coupled to the third coil 222, the feedback indicative of one or more parameters, such as the current level being induced into the third coil, that is indicative of the level of coupling efficiency being achieved between coils 190, 194 and the third coil 222. Adjustment and control of the relative levels of energy provided to coils 190, 194 may be performed manually by a user, such as a technician or physician, or may be performed automatically by a coil positioning system configured to reposition the coils 190, 194 and/or the patient having the IMD comprising the third coil 222.

By providing opposing magnetic fields that may be steered to generated a particular angle of a resultant magnetic field with the area of an estimated optimal recharging envelope such as recharging envelope 221 position between a pair of electrical coils such as coils 190 and 194, the orientation of at least one axis of a the coils 190, 194 relative to the normal vector of coil 222 when the third coil 222 is positioned with area of recharging envelope 221 a positional angle θ (theta) of rotation of the third coil around a longitudinal axis extending between the pair of recharging coils can be rendered irrelevant, and the angle of orientation φ (phi) an be compensated for to alignment of the direction of the resultant magnetic field with normal axis of the third coil, thus further maximizing the level of efficiency of the inductive coupling formed between the resultant magnetic field provide within the recharging envelope 221 and the electrical energy induced in the third coil. This maximum level of coupling efficiency may be achieved in some instances without the need to physically reposition, for example by tilting, the pair of electrical coils arranged to produce the resultant magnetic field once the third coil has been positioned within the area included in recharging envelope 221 between the pair of electrical coils, and without the need to use additional pairs of coils to generate addition magnetic fields to be imposed on the third coil. Additional compensation for a third coil (e.g., and X-axis coil) of the third coil in some examples may also be compensated for by rotation of the coils 190, 194 and the longitudinal axis 170 no more than ninety-degrees around a point of intersection of the normal axis (Z-axis) of the third coil 222 and the longitudinal axis 170, as illustrated and described above for example with respect to diagrams 180A-180D and FIG. 9B.

Figure 13:
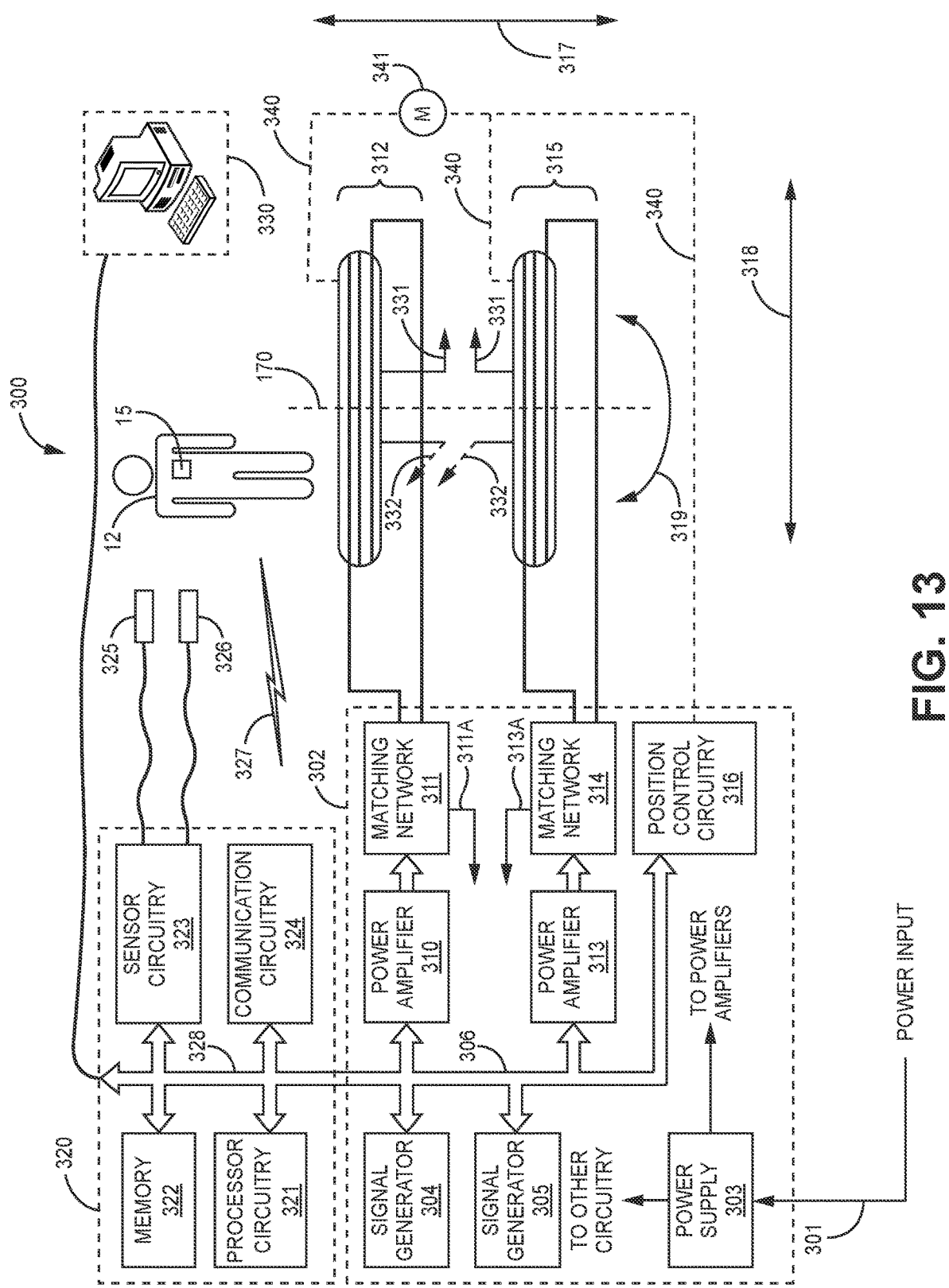
FIG. 13 is a conceptual block diagram illustrating a recharging system for recharging one or more implantable medical devices implanted in a patient according to various examples described in this disclosure.

FIG. 13 is a conceptual block diagram illustrating an example recharging system 300 for recharging one or more implantable medical devices 15 implanted in a patient 12 according to various examples described in this disclosure. As illustrated in FIG. 13, system 300 may be configured to provide inductive recharging of one or more implantable medical devices, illustratively represented as IMD 15, that may be implanted in a patient, illustratively represented as patient 12. System 300 includes recharging circuitry 302 that is coupled to a pair of coils 312, 315. The arrangement of coils 312 and 315 relative to patient 12 as shown in FIG. 13 is not necessarily intended to be illustrative of the actual arrangement, for example with respect to positioning and/or scale of the pair of coils 312, 315 and patient 12 during a period of time when recharging of IMD 15 is occurring, and is intended to be illustrative of various features of system 300. The actual arrangements of coils 312, 315 relative to each other and relative to patient 12 and IMD 15 may be as illustrated and described with respect to coils 102 and 103 as illustrated in FIG. 7, as illustrated and described with respect to coils 151, 161 and FIG. 8B, and/or with respect to coils 190 and 194 as illustrated and described with respect to FIGS. 9A-9B, 10A-10B, 11, and 12.

As illustrated in FIG. 13, system 300 includes control circuitry 320 coupled to recharging circuitry 302, and includes processor circuitry 321, a memory 322 coupled to processor circuitry 321, for example by bus/connections 328 (herein after "bus 328"). Memory 322 may store program instructions that, when retrieve and executed by processor circuitry 321, provides programming steps that allow processor circuitry 321 to control recharging circuitry 302 to perform the recharging processes associated with inductively recharging a power source or power sources located within an IMD 15 implanted in patient 2. In addition, memory 322 may also store values, for example charging values, charging times, patient history associated specifically with patient 12, communication protocols, and any other information that may be required or that may be helpful to allow processor circuitry 321 to control the inductive recharging process being used to recharge the power source or sources included in IMD 15 when implanted within patient 12 according to any of the techniques described in this disclosure, and any equivalents thereof.

Control circuitry 320 may include communication circuitry 324. Communication circuitry 324 may be used to receive and process signals from the IMD 15 implanted in patient 12 for use by processor circuitry 321 in controlling the inductive recharging processes including, but not limited to a battery management system that monitors and optimizes the recharge process. Communication circuitry 324 may also provide wireless communications with devices located externally to system 300, for example external device 104, or for example external computing devices 111A-111N, and/or external server 108 as described and illustrated with respect to FIG. 7. In FIG. 13, communication circuitry 324 as may also be used to download information, such as programing information, to control circuitry 320 that may then be stored in memory 322, and accessed by processor circuitry 321. In addition, memory 322 may be used to store information related to the recharging process performed by system 300, such as the levels of energy provided during a recharging process to coils 312 and 315, any fault conditions that have occurred during the recharging process, and any other information deemed necessary or helpful that may be related to the recharging processes performed by system 300. This information as stored in memory 322 may be provided to computing device 330, and/or uploaded and transmitted through communication circuitry 324 to some other external device or devices, as described above. Control circuitry 320 as illustrated in FIG. 13 may also include sensor circuitry 323 configured to be coupled one more different sensors 325, 326, and to receive signals from the sensors that may be further processed by sensor circuitry 323 and/or by processor circuitry 321, to provide and/or derive information that may be further used to control and regulate the inductive recharging processes being performed by system 300.

In various examples, one or more of the circuits illustrated as comprising control circuitry 320 may instead be provided by computing device 330. In various examples, computing device 330 includes a display and one or more input devices, such as a keyboard and/or a computer mouse, that allow a user, such as a physician or a clinician, to interact with the system 300. This interaction may include interaction to control the recharging processes to be performed or being performed by system 300. In some examples, computing device 330 is computing device 106 as illustrated and described with respect to FIG. 7, and is configured to provide some combination of or all of the features provided by computing device 106, and to perform some combination or all of the functions ascribed to computing device 106. In some examples, control circuitry 320 and recharging circuitry 302 comprise some or all of recharging circuitry 101 as illustrated and described with respect to FIG. 7, and may provide any of the features and be configured to perform any of the function ascribed to recharging circuitry 101.

As shown in FIG. 13, recharging circuitry 302 includes a power supply 303, a signal generator 304 (which may be comprised of an oscillator and signal generation circuitry), a plurality of power amplifiers 310 and 313, and a corresponding plurality of matching network circuitry 311, 314. The circuits of recharging circuitry 302 may be coupled by a bus/connection 306. Bus 306 may be a same bus as bus 328, or communicatively coupled to bus 328. Recharging circuitry 302 includes a first power amplifier 310 coupled to signal generator 304 and configured to receive a signal from the signal generator 304. First power amplifier 310 is also coupled to matching network circuitry 311, and configured to provide an output signal to the matching network circuitry 311 based on the signal received from the signal generator 304. Matching network circuitry 311 may be configured to provide impedance matching between power amplifier 310 and coil 312, and to provide outputs that may be coupled to coil 312 to energize coil 312. Recharging circuitry 302 in some examples includes a second power amplifier 313 coupled to signal generator 304, and configured to receive a signal provided by signal generator 304. Second power amplifier 313 is also coupled to matching network circuitry 314, and configured to provide an output signal to the matching network circuitry 314 based on the signal received from the signal generator 304. Matching network circuitry 314 is configured to provide impedance matching between power amplifier 313 and coil 315, and to provide outputs that may be coupled to coil 315 to energize coil 315. In some examples, recharging circuitry 302 may include a second signal generator 305 that is coupled to the second power amplifier 313, wherein the second signal generator 305 provides the input signal that is amplified by power amplifier 313 and provided through matching network 314 to energize coil 315. When the second signal generator 305 is utilized as part of system 300, the second signal generator 305 may be configured to generate an output signal that is phase locked to the output signal generated by the first signal generator 304 so the output signals provided by the first signal generator 304 and the second signal generator 305 are a same frequency signal and are in-phase with one another.

Power amplifiers 310 and 313 in some examples receive a signal including a waveform generated by signal generator 304, and provide power amplification of the received signal that is then applied through matching network circuitry 311, 314, respectively, to energize coils 312, and 315. Matching network circuitry 311 and 314 provides impedance matching between the output stage of the respective power amplifier that the matching network circuitry is coupled to and the coil that is being energized by that power amplifier. In various examples, a typical range of impedance provided as an output from one or more of power amplifiers 310, 313 may be in a range of 1 to 100 ohms, in some examples 50 ohms, wherein the real part of the input impedance of the coils 312, 315 would be in a range of 0.1 to 20 ohms, in some examples 0.5 ohms. The imaginary part of a complex impedance of the coils may be in a range of 60 to several hundred ohms, depending on the frequency of the signal or signal applied to the coils. In order to provide maximum power transfer between the power amplifier outputs and the respective coils these outputs are coupled to, the matching network circuitry 311, 314 are configured to match the impedance of the output of the power amplifier to the coils each power amplifier is coupled to through the respective matching network circuitry.

In some examples, matching network circuitry 311, 314 comprise an impedance matching transformer configured to match an output impedance of a power amplifier to an input impedance of a coil coupled to the output of the impedance matching circuitry. In some examples, matching network circuitry 311, and 314 comprises a transformer and/or a capacitor rated for peak voltage of the assembly and of a capacitance value that the inductive nature of the coil is accommodated. In one implementation, an adjustable vacuum ceramic capacitor is placed in series with a 50Ω to 1Ω transformer. Other configurations and devices may be used to perform the impedance matching function of matching network circuitry 311 and 314, and are contemplated for using in providing the matching network circuitry 311 and 314 as described in this disclosure.

In various examples of system 300, since it is more difficult to dynamically tune the quality factor of the receive coil within an implanted medical device such as IMD 15, or rather, change the frequency at which the quality factor is a maximum, it may significantly improve the maximum power delivered to IMD 15 by fixing the frequency of the system based on the characteristics of the receive coil and using a tunable vacuum capacitor located between the power amplifier (and after a following transformer) and a coil pair, such as coil 312 and 315, in order to match the output of the power amplifiers to the impedance presented by the coils without changing the oscillation frequency, as is practiced in other rechargeable wireless power transfer systems such as the RESTORE ULTRA® device from Medtronic plc, of Dublin, Ireland. A frequency-based maximization configuration may result in a non-optimal power transfer if the secondary/receive coil of IMD 15 are tuned to a frequency different than that found to maximize power transfer to the primary/transmit coils providing the inductive energy provide by system 300. Therefore, examples of the systems and methods described herein comprise tuning the impedance of the system at a fixed frequency, as opposed to varying the frequency of the system, in order to maximize the power delivered to a receive coil in the implanted device being recharged by the system.

As shown in FIG. 13, power supply 303 is coupled to a power input 301, and is configured to receive electrical power from input 301. Power input 301 may be any source of electrical power, such as commercially available electrical power supply by an electrical utility, for example electrical power having 110-120 volts RMS single-phase power at frequency of 50-60 Hz, as is commonly available in the United States. In other examples, input 301 may provide power in other arrangements, such as but not limited to 480V three-phase in an ungrounded delta configuration at 50-60 Hz, or 208 three-phase "Y" configuration at 50-60 Hz. Other voltages, frequencies, configurations, and numbers of phases are contemplated for use as input power to system 300, as would be understood by one of ordinary skill in the art. Power supply 303 is configured to receive electrical power at input 301, and may perform various operations on the received electrical power, including conditioning, filtering, and conversion of the input power voltage to one or more different voltages, including both different voltages provided as alternating current (AC) voltage supplies and direct current (DC) power supplies as outputs from power supply 403. The outputs are generally represented by the "TO OTHER CIRCUITRY" output arrow illustratively provided as an output from power supply 303, and may include any electrical power outputs required to power the circuitry for operation of the devices included in and powered from system 300.

In some examples, power supply 303 is also configured to provide one or more separate outputs, illustratively represented by the "TO POWER AMPLIFIERS" output arrow from power supply 303. These outputs from power supply 303 may be coupled to power amplifiers 310 and 313 provided as part of recharging circuitry 302, and wherein the "TO POWER AMPLIFIERS" output is configured to provide the electrical energy used to energize the coils 312 and 315 under the control of the power amplifiers 310 and 313, respectively.

In FIG. 13, signal generator 304 is coupled to bus 306, wherein signal generator 304 may be configured to generate one or more output signals that are used to control the waveforms of the electrical power used to energize coils 312 and 315. For example, signal generator 304 may generate a signal having sinusoidal voltage waveform and a particular frequency. This signal is provided to the power amplifiers and matching network circuitry of recharging circuitry 302. In some examples, the sinusoidal waveform is converted to the square waveform, the frequency of the square wave having a same frequency of the sinusoidal waveform generated by signal generator 304, or in other examples signal generator 304 may change the frequency of the square wave signal. In some examples, the duty cycle of the square wave may be the same as provided with the sinusoidal waveform (e.g., a 50% duty cycle), and in other examples, signal generator 304 may alter the duty cycle to a duty cycle other than a 50% duty cycle.

In some examples, signal generator 304 amplifies the signal for example to alter the voltage level of the signal. In some examples, signal generator 304 is configured to process the signal to retain the processed signal as a sinusoidal waveform, but for example acts as a buffer or driver to amplify and/or drive the output signal from the signal generator 304 to the power amplifiers 310 and 313, and for example to prevent the power amplifiers from loading down or otherwise distorting the signal being provided from the signal generator 304. In some examples, one or more of the power amplifiers comprise a Class D amplifier. In some examples, one or more of the power amplifiers comprise a Class E amplifier. In some examples, the signal generator 304 may provide recharge frequency tuning (closed loop or open loop), to optimize the wireless power transfer between coils 312, 315 and the receive antenna of IMD 15. This tuning may or may not be integrated and coordinated with the battery management system and telemetry/communication systems.

Once processed by signal generator 304, the signal generator 304 is coupled to power amplifier 310 that is configured to control the output of electrical energy provided by matching network circuitry 311 to coil 312 using the signal processed by signal generator 304, which may be provided by a coupling the power amplifier 310 to the "TO POWER AMPLIFIER" output of power supply 303. The output from power amplifier 310 is then provided as an output to matching network circuitry 311 to energize coil 312. Matching network circuitry 311 may also include a feedback 311A loop that provides a feedback signal, such as a varying voltage level, that is indicative of the level of energy, for example a current flow, being provided to coil 312 by matching network circuitry 311. This feedback signal may be processed by one or more devices included in system 300, for example processor circuitry 321 or computing device 330, or other battery management systems, to provide information that may be used to control and regulate the output of electrical energy being provided to energize coil 312. This information may also be used to apportion power to the appropriate coil of coil pair 312, 315, to steer the resultant magnetic field being imposed on IMD 15 to maximize power delivered to the receive circuit of the implanted device being recharged.

In a similar manner, signal generator 304 may also provide a signal to power amplifier 313, which receives power from the "TO POWER AMPLIFIERS" output from power supply 303, and to provide an output to matching network circuitry 314 to electrically energize coil 315. Power amplifier 313 and matching network circuitry 314 may be configured to operate and to provide any of the features and functions described above with respect to power amplifier 310 and matching network circuitry 311, respectively, in providing the electrical energy used to energize coil 315. In addition, matching network circuitry 314 includes a feedback signal 313A, that may be used in same or similar matter as described above with respect to feedback signal 311A, but for use in controlling and regulation of power amplifier 313 and the matching network circuitry 314 with respect to providing the electrical energy used to energize coil 315. This information may also be used to apportion power to the appropriate coils of the coil pair 312 and 315, to steer the resultant magnetic field being imposed on IMD 15 to maximize power delivered to the receive circuit of the implanted device being recharged.

In various examples, the same signal is provided by signal generator 304 to both power amplifier 310 and power amplifier 313. The power amplifiers 310, 313 may then process the signal and control matching network circuitry 311 and 314, respectively, so that a same level of electrical energy is provided to both sets of coils 312 and 315 at any given time when coils 312 and 315 are energized. The polarity of the electrical power provided to coils 312 and 315 may be arranged such that the coils generate opposing magnetic fields in the area between the coils, having a resultant magnetic field that is some portion to the area between the coils is perpendicular and surrounds in all directions the longitudinal axis common to both coils. In other examples, a different signal is provided by signal generator 304 to power amplifier 310 and to power amplifier 313, which may result in a different level of electrical energy being provided to energize coil 312 as is being provided to coil 315 at any given time.

For example, a signal having a higher voltage level but a same frequency may be provided as an output by one of power amplifiers 310 or 313 relative to the voltage level provided as an output by the other respective power amplifier. The difference in the voltage levels may provide different levels of electrical energy to energize the coils 312 and 315, respectively, and thus steer the resultant magnetic field illustratively shown as field 332 in FIG. 13. The relative difference in the level of the voltages being provided by the power amplifiers 310 and 313 may be controlled by information received as a feedback signal from IMD 15 that indicated the level of coupling efficiency and/or the overall level of energy being induced into the receive antenna of IMD 15 by the resultant magnetic field generated by coils 312, 315. In other examples, signal generator 304 and/or power amplifiers 310 and 313 may vary the relative duty cycles of the signals being provided to coils 312, 315 respectively, in order to vary the level of electrical energy being provided to energize the coils 312, 315, and thus to steer the angle of orientation of the resultant magnetic field 332 being provided by coils 312 and 315.

In some examples, a same signal is provided by signal generator 304 to both signal power amplifiers 310 and 313, but power amplifiers 310 and 313 process this same signal differently to provide different outputs to matching network circuitry 311 and 314 respectively, resulting in a different level of energy being provided to coil 312 as compared to coil 315 at any given time when the coils are energized. The capability of signal generator 304 to provide different signals to power amplifiers 310 and 313, and/or the ability of power amplifiers 310 and 313 to provide a different level of energy to each of coils 312 and 315 at any given time allow system 300 to steer the resultant magnetic field being generated between the coils 312 and 315 to maximize the coupling efficiency between the coils 312, 315 and a receive antenna of an IMD 15 undergoing recharge or being powered by the resultant magnetic field generated by the recharging coils 312, 315.

In addition, in some examples of system 300, a position control circuitry 316 is coupled to bus 306. The position control circuitry 316 is coupled to a structure 340 including one or more mechanical actuators, illustratively represented as motor 341. Structure 340 and motor 341 may be physically coupled to coils 312, 315, and in some examples to a structure (not shown in FIG. 13), such as a table where patient 12 may lay or sit when positioned between coils 312, 315. Position control circuitry may be configured to drive the motor 341 in order to control movements of structure 340, and thus the positioning of coils 312, 315, and/or a structure (not shown in FIG. 13) where the patient 12 is positioned, e.g., lying or sitting. Position control circuitry 316 may receive instructions, for example from processing circuitry 321, and control motor 341 in order to reposition coils 312, 315 and/or patient 12 having IMD 15 while keeping the relative positioning of coils 312, 315 the same relative to one another. Position control circuitry 316 may for example be configured to operate motor 341 to move coils 312, 315 and/or patient 12 and IMD 15 in an up or down direction as indicated by arrow 317, and/or in a left or right direction as indicated by arrow 318 in FIG. 13. The actuators controlled by position control circuitry 316 are not limited to any particular type of actuator device or devices, and may be a combination of two or more different types of actuator devices working in conjunction to position coils 312, 315. Actuator devices may include electrical actuators such as motors, including but not limited to stepper or servo motors, pneumatic or hydraulic actuators such as pneumatic or hydraulic motors, and/or pneumatic or hydraulic cylinders, and mechanical actuators that may include gears, rails, pulleys or other mechanical devices conjured to provide mechanical movement. Actuator devices may include linear actuator devices configured to provide movements in a linear direction, and rotary actuators configured to provide rotary movements.

In addition, position control circuitry 316 may also be configured to tilt or rotate the position of coils 312, 315 for example relative to the direction of longitudinal axis 170, as represented by arrow 319 in FIG. 13. As described above, movement and repositioning of the coils 312, 315 and/or patient 12 and IMD 15 may be based on one or more feedback signals provided from the IMD that are indicate of the level of electrical energy being induced into the receive antenna of the IMD. Position control circuitry 316 may be configured to receive this feedback information, or instructions generated for example by processing circuitry 321 based on the feedback information, and to move coils 312, 315 and/or patient 12 and IMD 15 to a position providing the most efficient coupling of the magnetic field being provided by coils 312 and 315 to the antenna of IMD 15 based on the feedback being provided.

In operation, a patient 12 with at least one IMD 15 that requires recharging of the power source located within the at least one IMD 15 is positioned so that the IMD 15 is located within the area of the resultant magnetic fields that will be generated by coils 312 and 315 when the coils are energized. Based on control provided by processor circuitry 321 and/or by instructions received from computing device 330, signal generator circuit 304 generates one or more signals that are provided to the power amplifiers 310 and 313. The power amplifiers, based at least in part on the received signal, and in some examples based on instructions received from processor circuitry 321, provide power outputs to energize coils 312 and 315. When energized, the coils being utilized generate opposing magnetic fields that generate a resultant magnetic field region that imposes the resultant magnetic field, such as resultant magnetic field 331, onto the receive antenna of IMD(s) 15, which begins to provide inductive charging to the power source located in IMD 15.

Signals either provided by IMD 15 to communication circuitry 324 and/or signals provided as feedback signals 311A, and 313A, are processed, for example by processor circuitry 321 and/or by position control circuitry 316, and may be used to reposition coils 312, 315 and/or a device where patient 12 is sitting or lying, as described above, if deemed necessary, in order to provide better coupling efficiency between the magnetic field provided by coils 312, 315 and the receive antenna of the IMD 15 being recharged. In some examples, positioning of the coils 312, 315 and/or the IMD 15 may include moving the coils and/or the patient/IMD up or down (as indicated by arrow 317), and/or left or right (as indicated by arrow 318) to position the receive antenna of the IMD 15 within the estimated optimal recharging envelope generated by the resultant magnetic field 331 provided in the area between the coils 312, 315.

In various examples, the relative level of power being provided to each of coils 312, 315 is altered in a manner to bend or steer the resultant magnetic field to form the non-perpendicular resultant magnetic field 332 in the area between the coils 312, 315 that aligns with a relevant axis of orientation, e.g., the normal vector, of the receive antenna of IMD 15. As described above, control of the positioning of coils 312, 315 and/or the receive antenna of IMD 15 to position the receive antenna in the estimated optimal recharging envelope being generated by the resultant magnetic fields in the area between coils 312, 315 may be made based on a feedback signal or signals receive from IMD 15 that is/are indicative of the strength or level of energy being induced into the receive antenna at any given time.

In some examples, control of the relative levels of electrical energy being provided to coils 312, 315 in order to steer the resultant magnetic field 332 being provided in the area between the coils may also be provided based on the feedback signal receive from IMD 15 that is indicative of the strength and/or level of energy being induced into the receive antenna at any given time. The feedback signal or instructor generated based on the feedback signal, for example generated by processor circuitry 321, may be provided to position control circuitry 316, to cause position control circuitry 316 to reposition coils 312, 315 and/or to reposition patient 12 to locate the receive antenna of IMD 15 within the estimated optimal recharging envelope of the resultant magnetic field generated between coils 312 and 315. The feedback signal or the instructions generated based on the feedback signal may also be provided signal generator 304 and/or power amplifiers 310 and 313, to cause recharging circuitry 302 to control the relative level of electrical energy being provided by the circuitry to each of coils 312 and 315 in order to steer the resultant magnetic field (e.g., resultant magnetic field 332 as shown in FIG. 13), to maximize the coupling efficiency being achieved between the resultant magnetic field and the receive antenna of IMD 15.

During the process of inductively recharging the power source located in IMD 15, various sensors 325, 326, may be monitored, and the information received from or derived from the sensors may be used to further control the recharging process. For example, temperature sensors located at the coils may provide signals indicative of the temperatures of coils 312, 315, and may be monitored during the recharging process to determine if one or more of the coils may be overheating. In some examples, one or more of sensors 325, 326 may sense a magnetic field strength and/or direction of the resultant magnetic field at one or more locations in the area between coils 312 and 315. The information from the one or more sensors 325, 326 may be revived at sensor circuitry 323, and may be further processed, for example by processing circuitry 321, to further control the recharging process being performed by system 300. For example, the level of the intensity of the magnetic field being generated by coils 312 and 315 as sensed by the one or more sensor 325, 326 may be monitored to assure that a safe level of exposure to the electromagnetic fields provided to the patient are maintained.

In some examples, a temperature of the patient 12 or of IMD 15 may be monitored during the recharging process. These sensed temperatures of patient 12 and/or of IMD 15 may be used to control the recharging process for example by lowering (reducing) the level of energy being provided to the coils if the temperature of the patient 12 or of IMD 15 is rising, and for example shutting off the energy being provided to the coils if the temperature of the patient or of IMD 15 exceeds a temperature considered to be safe for the patient. Further, the strength of the magnetic field being generated and imposed on IMD 15 may be monitored during the recharging process, and the sensed strength of the magnetic fields may be processed and used to further regulate the process, for example to raise or lower the level of electrical energy being provided to the coils. Monitoring of the strength of the magnetic field imposes on the patient may be required to assure that the level of the strength of the magnetic field does not exceed a predetermined level, or a predetermined level for more than a predetermined time period. The monitoring may include a reduction, including lower the energy level or shutting off the electrical energy provided to the coils for safety reasons if the strength of the magnetic field exceeds some predetermined value or values, either instantaneous and/or over some predetermined time period.

In various examples, processor circuitry 321 regulates various functions related to the recharging process. Processor circuitry 321 may include a timer function for controlling and limiting the duration of time the patient 12 may be exposed to the magnetic fields being generated coils 312, 315 during the recharging process. Timing functions may be provided by one or more timers included in processor circuitry 321, and may timeout based on one or more timer values stored in memory 322. Processor circuitry 321 may also regulate a profile of the levels of electrical energy provided to the coils over the duration of the recharging process, so that the levels of electrical energy provided to each of the coils 312 and 315 may be set and/or varied over the duration of the recharging process based on a profile that may be stored in memory 322 and retrieved and executed by processor circuitry 321. In some examples, IMD 15 may provide a signal (e.g., wireless signal 327) to communication circuitry 324 that indicates the level of recharge that has been provided to the power source within IMD 15. Processor circuitry 321 may further regulate and/or terminate the recharging process of IMD 15 based on this information. For example, a wireless signal 327 provided by IMD 15 may indicate that the power source located within IMD 15 is fully recharged, and further exposure to the magnetic fields by both patient 12 and IMD 15 will provide no further charging of the power source. In such instances, processor circuitry 321 may terminate the recharging process in order to minimize the amount of exposure of patient 12 to the magnetic fields generated by system 300, regardless of whether or not a timer has indicated that the time for recharging the power source of IMD 15 has expired.

Figure 14:
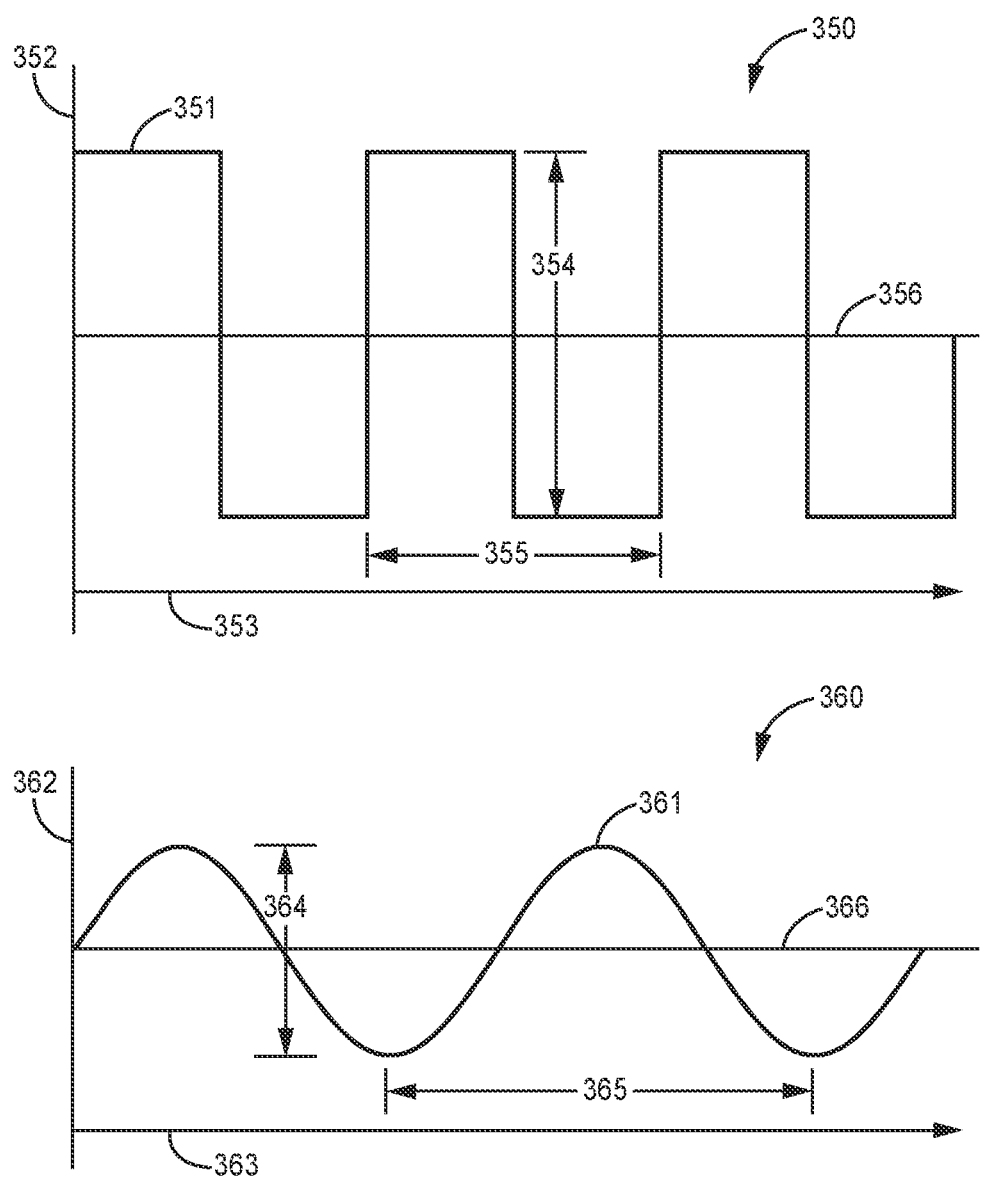
FIG. 14 illustrates graphs of representative waveforms that may be generated by a signal generator and applied to the recharging coils of a recharging circuitry according to various examples described in this disclosure.

FIG. 14 illustrates examples graphs 350, 360 of representative waveforms that may be generated by a signal generator, such as signal generator 304 and/or signal generator 305 as illustrated and described with respect to FIG. 13, and applied to the coils coupled to recharging circuitry according to various examples described in this disclosure. Graph 350 illustrates an example waveform 351 of a square wave having an amplitude value plotted against the vertical axis 352 over time, time represented by horizontal axis 353. Waveform 351 comprises a peak-to-peak amplitude 354, and a cycle period 355. In various examples, the peak-to-peak amplitude 354 of waveform 351 may comprise a voltage range of 10 mV to 100 volts, in some examples, 5 volts. The peak-to-peak amplitude in some examples is dependent on the power amplifier selected that the waveform 351 is being provided to in order to generate the output used to energize one or both of a pair of electrical coils arranged as recharging coils. In some examples, the power amplifier being driven by the waveform 351 is a fixed amplification power amplifier, capable of providing a 400 Watt output signal based on a variable input signal having a peak-to-peak amplitude 10-200 mV. In some examples, a reference voltage level 356 may comprise a zero-volt reference voltage, wherein a portion of waveform 351 is provided at voltage level that is a higher voltage than the reference voltage 356, and a portion of waveform 351 is provided at a voltage level that is less than the reference voltage level 356. In various examples, the duty cycle of waveform 351 over period 355 provides a fifty-percent duty cycle. In various examples, the duty cycle of waveform 351 over the period 355 provides a duty cycle other than a fifty-percent duty cycle. In various examples the time period 355 of waveform 351 is in a range of 100 microseconds to 10 nanoseconds, representative of a frequency range of 10 kHz to 100 MHz for waveform 351.

In some examples, an electrical current having a waveform corresponding to waveform 351 is applied to a pair of electrical coils that are electrically coupled in series with one another, such as electrical coils 131 and 132 as illustrated and described with respect to wiring diagram 130 and FIG. 8A. When waveform 351 as shown in FIG. 14 is applied to such a pair of series wired coils, and coupled so that the pair of coils generate opposing magnetic fields interacting with each other within an area between the coils, portions of the resultant magnetic field may have a direction that is perpendicular to the longitudinal axis common to both coils, for example as illustrated and described with respect to FIGS. 9A, 10A-10B, and 11. This portion of the resultant magnetic field can be used to induce an electrical current into a third coil positioned within the portions of the resultant magnetic field that include the perpendicular direction. In addition, the pair of electrical coils being energized by the application of electrical current in the form of waveform 351 may also be tilted so that the direction of the resultant magnetic field aligns with a third axis of orientation of the third coil in order to maximize the level of coupling efficiency occurring between the resultant magnetic field and the current being induced into the third coil. As a result, a maximum level of coupling efficiency between the electrical power being provided to the pair of electrical coils via waveform 351 and the level of current being induced into the third coil may be achieved using only a single pair of electrical coils to generate the resultant magnetic field.

In some examples, different versions of electrical current may be applied to the coils of a pair of electrical coils, but versions of the electrical current corresponding to waveform 351, but with one or more electrical parameters of the waveform applied to the coils—e.g., a first version of waveform 351 having a first value for amplitude 354 of waveform 351 is applied to a first electrical coil, such as coil 312, and a second version of waveform 351 having a second value for amplitude 354 that is different from, e.g., having a larger or smaller value for amplitude 354, is applied to energize the second electrical coil, such as electrical coil 315. By providing waveform 351 having a different value for amplitude 354 to each of the electrical coils, the resultant magnetic fields generated between the coil using opposing magnetic fields may be steered so that a direction associated with the resultant magnetic fields generated within the optimal recharging envelope can be directed to some non-perpendicular angle relative to the longitudinal axis common to both of the electrical coils.

Other and/or different combinations of differences between the electrical parameters of waveform 351 applied to the first electrical coil and at a same time to the second electrical coil is not limited to variation of the amplitude 354 of the waveforms, and may include other variation, such as differences in the duty cycle of the waveforms applied for example to the first coil compared to a duty cycle of the waveform that is applied to the second electrical coil.

Graph 360 illustrates an example waveform 361 of a sinusoidal waveform generated from the signal generator 304, and having a varying amplitude value plotted against the vertical axis 362 over time, time represented by horizontal axis 363. Waveform 361 comprises a peak-to-peak amplitude 364, and having a period 365. In various examples, the peak-to-peak amplitude 364 may comprise a voltage range of 10 mV to 100 volts, in some examples, 5 volts peak-to-peak depending on the desired peak magnetic field intensity and the capacity of the power amplifier employed. In some examples, the power amplifier is a fixed 400 Watt power amplifier, in other example the power amplifier comprises a variable output between 2 Watt and 1 kW. In some examples, a reference voltage level 366 may comprise a zero-volt reference voltage, wherein a portion of waveform 361 provides a voltage level above the reference voltage level 366, and another portion of each cycle of waveform 361 comprises voltage value that is below the reference voltage level 366. In various examples, the duty cycle of waveform 361 over period 365 provides a fifty-percent duty cycle. In various examples the time period 365 of waveform 361 is in a range of 100 microseconds to 10 nanoseconds, representative of a frequency range of 10 kHz to 100 MHz for waveform 361.

In some examples, an electrical current having a waveform corresponding to waveform 361 is applied to a pair of electrical coils that are electrically coupled in series with one another, such as electrical coils 131 and 132 as illustrated and described with respect to wiring diagram 130 and FIG. 8A. When waveform 361 as shown in FIG. 14 is applied to such a pair of series wired coils, and coupled so that the pair of coils generate opposing magnetic fields interacting with each other within an area between the coils, portions of the resultant magnetic field may have a direction that is perpendicular to the longitudinal axis common to both coils, for example as illustrated and described with respect to FIGS. 9A, 10A-10B, and 11. This portion of the resultant magnetic field can be used to induce an electrical current into a third coil positioned within the portions of the resultant magnetic field that include the perpendicular direction. In addition, the pair of electrical coils being energized by the application of electrical current in the form of waveform 361 may also be tilted so that the direction of the resultant magnetic field aligns with a third axis of orientation of the third coil in order to maximize the level of coupling efficiency occurring between the resultant magnetic field and the current being induced into the third coil. As a result, a maximum level of coupling efficiency between the electrical power being provided to the pair of electrical coils via waveform 351 and the level of current being induced into the third coil may be achieved using only a single pair of electrical coils to generate the resultant magnetic field.

In some examples, different versions of electrical current may be applied to the coils of a pair of electrical coils, but versions of the electrical current corresponding to waveform 361, but with one or more electrical parameters of the waveform applied to the coils—e.g., a first version of waveform 361 having a first value for amplitude 364 of waveform 361 is applied to a first electrical coil, such as coil 312, and a second version of waveform 361 having a second value for amplitude 364 that is different from, e.g., having a larger or smaller value for amplitude 364, is applied to energize the second electrical coil, such as electrical coil 315. By providing waveform 361 having a different value for amplitude 364 to each of the electrical coils, the resultant magnetic fields generated between the coil using opposing magnetic fields may be steered so that a direction associated with the resultant magnetic fields generated within the optimal recharging envelope can be directed to some non-perpendicular angle relative to the longitudinal axis common to both of the electrical coils.

Other and/or different combinations of differences between the electrical parameters of waveform 361 applied to the first electrical coil and at a same time to the second electrical coil is not limited to variation of the amplitude 364 of the waveforms, and may include other variation, such as differences in the phases of the waveforms applied for example to the first coil compared to a duty cycle of the waveform that is applied to the second electrical coil.

Figure 15:
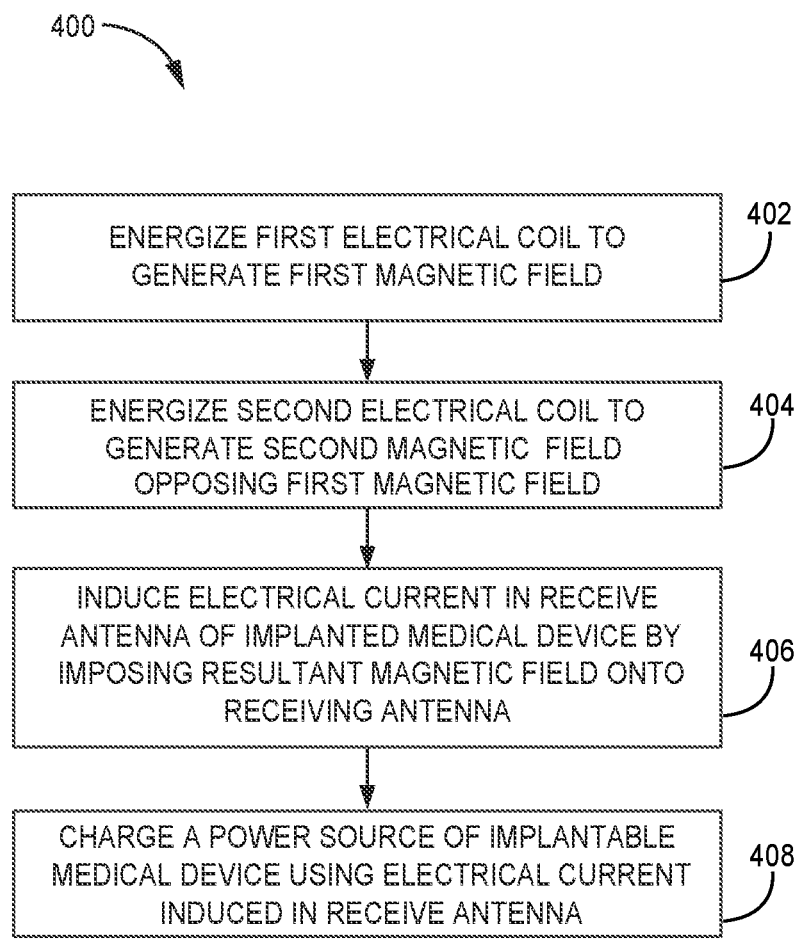
FIG. 15 is a flowchart illustrating a method 400 according to various examples described in this disclosure.

FIG. 15 illustrates a flowchart illustrating a method 400 according to various examples described in this disclosure. Although method 400 is described with respect to the devices and systems illustrated with respect to system 300 of FIG. 13, method 400 is not limited to being performed by system 300, and may be performed, in whole or in part, by any of the example devices and/or systems described in this disclosure, and the equivalents thereof. Method 400 includes a method for recharging a power source located in an implanted medical device 15 implanted in a patient 12.

Method 400 includes energizing, by an electrical power source, a first electrical coil 312 to generate a first magnetic field (block 402). In various examples, the first electrical coil comprises a circular shaped winding encircling a center point and having each of the windings of the first electrical coil formed at a distance of a least a value for a radius of the circular shaped winding. The electrical power source may include a power amplifier 310 coupled to receive a signal from a signal generator 304, the power amplifier configured to amplify the received signal and to provide an output signal through an impedance matching network 311 to energize the first electrical coil 312.

Method 400 includes energizing, by an electrical power source, a second electrical coil 315 to generate a second magnetic field opposing the first magnetic field in an area between first electrical coils and the second electrical coil (block 402). The second electrical coil may comprise a circular shaped winding encircling a center point and having each of the windings of the first electrical coil formed at a distance of a least a value for a radius of the circular shaped winding. The circular shape winding of the second electrical coil may have a same set of dimensions as the circular shape winding of the first electrical coil, and having a common longitudinal axis that includes the center point of both the first and second electrical coils. As distance between the first electrical coil and the second electrical coil may have a value equal to the radii of the circular shaped winding of both the first electrical coil and the second electrical coil The electrical power source coupled to the second electrical coil 315 may include a power amplifier 313 coupled to receive a signal from a signal generator 304, the power amplifier 313 configured to amplify the received signal and to provide an output signal through an impedance matching network 314 to energize the second electrical coil 315.

Method 400 includes inducing an electrical current in a receive antenna (third coil) of an implanted medical device placed between the first electrical coil and the second electrical coil by imposing a resultant magnetic field generated by the interaction of the opposing first magnetic field and the second magnetic field onto the receive antenna (block 406). Imposing the resultant magnetic field generated by the interaction of the opposing first magnetic field and the second magnetic field may comprise positioning the receive antenna with an estimated optimal recharging envelope (recharging envelope) formed in the area between the first electrical coil and the second electrical coil. Positioning of the receive antenna within the estimated optimal recharging field renders a positional angle θ (theta) of rotation of the third coil around a longitudinal axis extending between the pair of recharging coils irrelevant with respect to a coupling efficiency of the level of the electrical current being induced in the third coil by the resultant magnetic field.

Method 400 includes charging a power source of the implanted medical device using electrical current induced in the receive antenna (block 408). Charging the power source of the implanted medical device may include providing a feedback signal indicative of the level of electrical energy being induced into the receive antenna of the implanted medical device. In some examples, movement of the first and second coils 312, 315 relative to the position of the receive antenna (third coil) may be performed by position control circuitry controlling a positioning device, such as a motor or other type of actuator devices, such as pneumatic or hydraulic cylinders, arranged to position coils 312, 315 based on the feedback signal provided by IMD 15. In some examples, movement of the coils 312, 315 comprises movement of the coils in an up or down direction and/or in a left or right direction relative to the position of the third coil in order to position the location of the third coil within the recharging envelope generated in an area between the coils 312, 315, while maintaining a same relative spacing and positioning between coils 312 and 315. In some examples, movement of the coils 312, 315 includes tilting of the coils 312, 315 relative to the orientation of the longitudinal axis 170 common to both coils to align the resultant magnetic field generated between the coils 312, 315 to a normal vector of the receive antenna (third coil) of the implantable medical device 15.

The feedback signal received (for example by communication circuitry 324) from IMD 15 may include information and/or data that is indicative of the level of electrical energy that is being induced into the receive antenna of the IMD during a recharging process being performed on IMD 15 by system 300. Movement of coils 312, 315 based on the feedback signal provided by IMD 15 may be controlled manually by a user, such as a physician or clinician, for example by providing inputs to computing device 330. In some examples, movement of coils 312, 315 based on the feedback signal provided by IMD 15 may be automatically controlled, for example by instructions generated by processor circuitry 321, and provided to positioning control circuitry 316. Movement of coils 312, 315 may be performed in order locate the receive antenna of IMD 15 within the recharging envelope including the resultant magnetic field generated in the area between coils 312, 315, and/or to further increase the level of coupling efficiency being achieved between the resultant magnetic field and the receive antenna once the received antenna has been positioned within the resultant magnetic field.

Imposing the resultant magnetic field generated by coils 312, 315 onto the receive antenna (third coil) of IMD 15 may include adjusting the relative intensities of the first magnetic field generated by coil 312 and the second magnetic field generated by the second electrical coil 315 based on the feedback signal provided by IMD 15. Adjustment of the relative intensities of the first magnetic field and the second magnetic field may be performed to steer or bend the resultant magnetic field to better align with a normal vector, e.g. a third axis of orientation, of the receive antenna of IMD 15. Steering the resultant magnetic field may be used to compensate for an angle of orientation φ (phi) between the normal axis of the third coil and the longitudinal axis to achieve a better level of inductive coupling efficiency between the recharging coils 312, 315 and the receive antenna of the IMD 15.

The level of adjustment may be controlled based on the feedback signal provided by the IMD 15 that is indicative of the level of coupling efficiency and/or the level of electrical energy being induced into the receive antenna by the resultant magnetic field being generated by coil 312, 315. Adjustment of the relative intensities of the first magnetic field and the second magnetic field may be controlled manually by a user, such as a physician or clinician, for example by providing inputs to computing device 330. In some examples, adjustment of the relative intensities of the first magnetic field and the second magnetic field based on the feedback signal provided by IMD 15 may be automatically controlled, for example by instructions generated by processor circuitry 321, and to signal generator 304 and/or power amplifier 310 and 313 to control one or more electrical parameters of the electrical power being provide through these devices to energize coils 312, 315.

The techniques of this disclosure may be implemented in a wide variety of computing devices, medical devices, or any combination thereof. Any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may be implemented, at least in part, in hardware, software, firmware or any combination thereof. For example, various aspects of the techniques may be implemented within one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, stimulators, or other devices. The terms "processor," "processing circuitry," "controller" or "control module" may generally refer to any of the foregoing logic circuitry, alone or in combination with other logic circuitry, or any other equivalent circuitry, and alone or in combination with other digital or analog circuitry.

For aspects implemented in software, at least some of the functionality ascribed to the systems and devices described in this disclosure may be embodied as instructions on a computer-readable storage medium such as random-access memory (RAM), read-only memory (ROM), non-volatile random access memory (NVRAM), electrically erasable programmable read-only memory (EEPROM), FLASH memory, magnetic media, optical media, or the like that is tangible. The computer-readable storage media may be referred to as non-transitory. A server, client computing device, or any other computing device may also contain a more portable removable memory type to enable easy data transfer or offline data analysis. The instructions may be executed to support one or more aspects of the functionality described in this disclosure.

In some examples, a computer-readable storage medium comprises non-transitory medium. The term "non-transitory" may indicate that the storage medium is not embodied in a carrier wave or a propagated signal. In certain examples, a non-transitory storage medium may store data that can, over time, change (e.g., in RAM or cache).

Various aspects of this disclosure have been described. These and other aspects are within the scope of the following claims.

What is claimed is:

1. A method for recharging a power source located in an implantable medical device configured for implantation within a patient, the method comprising:

energizing, by recharging circuitry, a first electrical coil to generate a first magnetic field having a first magnetic field direction;

energizing, by the recharging circuitry, a second electrical coil to generate a second magnetic field having a second magnetic field direction opposing the first magnetic field direction relative to a longitudinal axis extending between the first electrical coil and the second electrical coil, wherein an interaction between the first magnetic field and the second magnetic field generates a resultant magnetic field within a recharging envelope located in an area between the first electrical coil and the second electrical coil when the first electrical coil and the second electrical coil are electrically energized;

inducing, by the resultant magnetic field, an electrical current in a third coil within the implantable medical device by imposing the resultant magnetic field onto the third coil when the third coil is located within the recharging envelope and the first electrical coil and the second electrical coil are electrically energized, wherein the resultant magnetic field generated within the recharging envelope comprises a resultant magnetic field direction that renders irrelevant a positional angle θ (theta) of rotation of the third coil around the longitudinal axis extending between the first electrical coil and the second electrical coil with respect to a coupling efficiency of the level of the electrical current being induced in the third coil by the resultant magnetic field; and charging, by the electrical current induced in the third coil, the power source in the implantable medical device.

2. The method of claim 1, wherein the first electrical coil and the second electrical coil comprise separate circular-shaped windings that are separated from each other by a separation distance such that at least a portion of the implantable medical device may be disposed in the resultant magnetic field generated in the area between the first electrical coil and the second electrical coil.

3. The method of claim 1, wherein energizing the first electrical coil and the second electrical coil further comprises:

coupling, by the recharging circuitry, a same level of electrical energy to energize both the first electrical coil and the second electrical coil to generate the resultant magnetic field within the recharging envelope, the resultant magnetic field having a direction within the recharging envelope that is perpendicular to the longitudinal axis common to both the first electrical coil and the second electrical coil, and that surrounds the longitudinal axis.

4. The method of claim 1, wherein energizing the first electrical coil and the second electrical coils further comprises:

coupling, by recharging circuitry, a first level of electrical energy to energize the first electrical coil and a second level of electrical energy to the second electrical coil, the first level of electrical energy different from the second level of electrical energy; and steering, by the recharging circuitry, the resultant magnetic field direction of the resultant magnetic field generated within the recharging envelope by controlling a relative difference between the first level of electrical energy and the second level of electrical energy to align a direction of the resultant magnetic field to an angle of orientation φ (phi) between a normal axis of the third coil and the longitudinal axis extending between the first electrical coil and the second electrical coil.

5. The method of claim 4, wherein the resultant magnetic field direction forms an angle that is non-perpendicular and non-parallel relative to the longitudinal axis common to both the first electrical coil and the second electrical coil, and that surrounds the longitudinal axis.

6. The method of claim 1, further comprising:

receiving, by communication circuitry, a feedback signal transmitted by the implantable medical device, the feedback signal indicating a level of the coupling efficiency being achieved between the resultant magnetic field and the third coil within the implantable medical device;

determining, by processing circuitry coupled to the communication circuitry, an initial position of the first electrical coil and the second electrical coil relative to the third coil based at least in part on the feedback signal, wherein the initial position places the third coil within the recharging envelope generated between the first electrical coil and the second electrical coil when the first electrical coil and the second electrical coil are energized; and controlling, by the position control circuitry, one or more movements to position the first electrical coil and the second electrical coil at the initial position to locate the third coil within the recharging envelope.

7. The method of claim 6, further comprising:

receiving, by communication circuitry, the feedback signal indicating a level of the coupling efficiency being achieved between the resultant magnetic field and the third coil within the implantable medical device once the third coil within the implantable medical device is located within the recharging envelope;

determining, by the processing circuitry coupled to the communication circuitry, a final position of the first electrical coil and the second electrical coil second relative to the third coil that tilts the resultant magnetic field that is perpendicular to the longitudinal axis so that the resultant magnetic field direction generated within the recharging envelope aligns with a normal vector of the third coil; and controlling, by the position control circuitry, the one or more movements to position the first electrical coil and the second electrical coil at the final position to align the resultant magnetic field direction imposed on the third coil with the normal vector of the third coil.

8. The method of claim 6, wherein the third coil comprises a uni-directional planar antenna.

9. The method of claim 1, wherein the third coil within the implantable medical device is configured for implantation within a chamber of a heart of the patient.

10. The method of claim 1, wherein the implantable medical device comprises a device including the third coil implanted within a pulmonary artery of the patient.

* * * * *